US011932625B2

(12) United States Patent
Gray et al.

(10) Patent No.: US 11,932,625 B2
(45) Date of Patent: Mar. 19, 2024

(54) INHIBITORS OF CYCLIN-DEPENDENT KINASE 12 (CDK12) AND USES THEREOF

(71) Applicant: Dana-Farber Cancer Institute, Inc., Boston, MA (US)

(72) Inventors: Nathanael S. Gray, Stanford, CA (US); Tinghu Zhang, Brookline, MA (US); Baishan Jiang, Brookline, MA (US); Nicholas Paul Kwiatkowski, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 17/688,822

(22) Filed: Mar. 7, 2022

(65) Prior Publication Data

US 2022/0213067 A1 Jul. 7, 2022
US 2023/0227433 A9 Jul. 20, 2023

Related U.S. Application Data

(63) Continuation of application No. 16/462,892, filed as application No. PCT/US2017/063132 on Nov. 22, 2017, now Pat. No. 11,306,070.

(60) Provisional application No. 62/425,519, filed on Nov. 22, 2016.

(51) Int. Cl.
C07D 403/04 (2006.01)
C07D 401/14 (2006.01)

(52) U.S. Cl.
CPC ......... *C07D 403/04* (2013.01); *C07D 401/14* (2013.01)

(58) Field of Classification Search
CPC ............................ C07D 403/04; C07D 401/14
See application file for complete search history.

(56) References Cited

U.S. PATENT DOCUMENTS

| | | | |
|---|---|---|---|
| 6,143,764 A | 11/2000 | Kubo et al. |
| 6,329,380 B1 | 12/2001 | Goulet et al. |
| 10,047,070 B2 | 8/2018 | Gray et al. |
| 10,906,889 B2 | 2/2021 | Bradley et al. |
| 10,969,394 B2 | 4/2021 | Marto et al. |
| 11,040,957 B2 | 6/2021 | Ciblat et al. |
| 11,306,070 B2 | 4/2022 | Gray et al. |
| 11,325,910 B2 | 5/2022 | Gray et al. |
| 2009/0054392 A1 | 2/2009 | Pelletier et al. |
| 2009/0111985 A1 | 4/2009 | Ashwell et al. |
| 2009/0136499 A1 | 5/2009 | Lapierre et al. |
| 2011/0039873 A1 | 2/2011 | Gaeta et al. |
| 2012/0165309 A1 | 6/2012 | Takahashi et al. |
| 2016/0264551 A1 | 9/2016 | Ciblat et al. |
| 2016/0264552 A1 | 9/2016 | Bradley et al. |

(Continued)

FOREIGN PATENT DOCUMENTS

| | | |
|---|---|---|
| JP | 2003-503351 | 1/2003 |
| JP | 2003-503351 A | 1/2003 |

(Continued)

OTHER PUBLICATIONS

International Search Report and Written Opinion for PCT/US2014/061206, dated Feb. 9, 2015.

(Continued)

*Primary Examiner* — Daniel R Carcanague
(74) *Attorney, Agent, or Firm* — Wolf, Greenfield & Sacks, P.C.

(57) ABSTRACT

The present invention provides novel compounds of Formulae (I') and (II), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating and/or preventing proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, ovarian cancer, neuroblastoma, lung cancer, colorectal cancer), benign neoplasms, diseases associated with angiogenesis, inflammatory diseases, autoinflammatory diseases, and autoimmune diseases) in a subject. Treatment of a subject with a proliferative disease using a compound or composition of the invention may inhibit the aberrant activity of a kinase, such as a cyclin-dependent kinase (CDK) (e.g., CDK12), and therefore, induce cellular apoptosis and/or inhibit transcription in the subject.

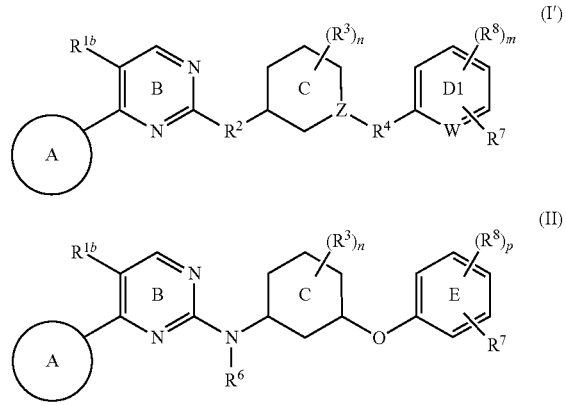

30 Claims, 3 Drawing Sheets

Specification includes a Sequence Listing.

(56) References Cited

U.S. PATENT DOCUMENTS

| | | |
|---|---|---|
| 2016/0264554 A1 | 9/2016 | Gray et al. |
| 2017/0204096 A1 | 7/2017 | Gelin et al. |
| 2019/0031642 A1 | 1/2019 | Gray et al. |
| 2019/0241541 A1 | 8/2019 | Ciblat et al. |
| 2019/0292167 A1 | 9/2019 | Bradley et al. |
| 2021/0292299 A1 | 9/2021 | Gray et al. |
| 2021/0300911 A1 | 9/2021 | Gray et al. |
| 2021/0317105 A9 | 10/2021 | Gray et al. |
| 2022/0055998 A1 | 2/2022 | Gray et al. |
| 2022/0073512 A1 | 3/2022 | Gray et al. |
| 2022/0089611 A1 | 3/2022 | Gray et al. |
| 2023/0114207 A1* | 4/2023 | Gray .............. A61K 31/7048 424/172.1 |

FOREIGN PATENT DOCUMENTS

| | | |
|---|---|---|
| JP | 2010-536869 | 12/2010 |
| JP | 2010-536869 A | 12/2010 |
| JP | 2011-515371 | 5/2011 |
| JP | 2011-515371 A | 5/2011 |
| JP | 2012-511021 | 5/2012 |
| JP | 2012-511021 A | 5/2012 |
| JP | 2016-512534 | 4/2016 |
| JP | 2016-512534 A | 4/2016 |
| JP | 2016-533379 A | 10/2016 |
| WO | WO 2000/047212 A1 | 8/2000 |
| WO | WO 2006/038001 A1 | 4/2006 |
| WO | WO 2006/072831 A1 | 7/2006 |
| WO | WO 2007/129195 A2 | 11/2007 |
| WO | WO 2009/115572 A2 | 9/2009 |
| WO | WO 2010/065893 A1 | 6/2010 |
| WO | WO 2012/066061 A1 | 5/2012 |
| WO | WO 2013/074986 A1 | 5/2013 |
| WO | WO 2014/063068 A1 | 4/2014 |
| WO | WO 2014/165065 A1 | 10/2014 |
| WO | WO 2015/058126 A1 | 4/2015 |
| WO | WO 2015/058140 A1 | 4/2015 |
| WO | WO 2015/154038 A1 | 10/2015 |
| WO | WO 2016/058544 A1 | 4/2016 |
| WO | WO 2016/160617 | 10/2016 |
| WO | WO 2016/201370 A1 | 12/2016 |
| WO | WO 2020/123925 | 6/2020 |
| WO | WO 2021/133601 A1 | 7/2021 |

OTHER PUBLICATIONS

International Preliminary Report on Patentability for Application No. PCT/US2017/063132 dated Jun. 6, 2019.
International Search Report and Written Opinion for Application No. PCT/US2017/063132 dated Jan. 29, 2018.
International Search Report and Written Opinion for PCT/US2014/061232, dated Dec. 23, 2014.
CAS Registry No. 1025964-63-9 Entered STN: Jun. 6, 2008.
CAS Registry No. 1026531-51-0 Entered STN: Jun. 8, 2008.
CAS Registry No. 1026878-26-1 Entered STN: Jun. 10, 2008.
CAS Registry No. 1026975-11-0 Entered STN: Jun. 10, 2008.
CAS Registry No. 1027155-85-6 Entered STN: Jun. 11, 2008.
CAS Registry No. 1028288-20-1 Entered STN: Jun. 15, 2008.
CAS Registry No. 1347533-63-4 Entered STN: Dec. 2, 2011.
CAS Registry No. 1347548-09-7 Entered STN: Dec. 2, 2011.
CAS Registry No. 1609787-73-6 Entered STN: Jun. 6, 2014.
CAS Registry No. 1702381-29-0 Entered STN: May 13, 2015.
CAS Registry No. 1702381-42-7 Entered STN: May 13, 2015.
CAS Registry No. 1702381-64-3 Entered STN: May 13, 2015.
CAS Registry No. 1702381-71-2 Entered STN: May 13, 2015.
CAS Registry No. 1702381-78-9 Entered STN: May 13, 2015.
CAS Registry No. 1702809-46-8 Entered STN: May 13, 2015.
CAS Registry No. 1703051-55-1 Entered STN: May 13, 2015.
CAS Registry No. 1703051-60-8 Entered STN: May 13, 2015.
CAS Registry No. 1703051-61-9 Entered STN: May 13, 2015.
CAS Registry No. 1703051-63-1 Entered STN: May 13, 2015.
CAS Registry No. 1998741-41-5 Entered STN: Sep. 23, 2016.
CAS Registry No. 1998741-43-7 Entered STN: Sep. 23, 2016.
CAS Registry No. 956025-12-0 Entered STN: Nov. 27, 2007.
Liang et al., CDK12: A Potent Target and Biomarker for Human Cancer Therapy. Cells. Jun. 18, 2020;9(6):1483. doi: 10.3390/cells9061483. PMID: 32570740; PMCID: PMC7349380.
Liu et al., Developing irreversible inhibitors of the protein kinase cysteinome. Chem Biol. Feb. 21, 2013;20(2):146-59. doi: 10.1016/j.chembiol.2012.12.006. PMID: 23438744; PMCID: PMC3583020.
Zhang et al., Covalent targeting of remote cysteine residues to develop CDK12 and CDK13 inhibitors. Nat Chem Biol. Oct. 2016;12(10):876-84. doi: 10.1038/nchembio.2166. Epub Aug. 29, 2016. PMID: 27571479; PMCID: PMC5033074.
Alam et al., Synthesis and SAR of aminopyrimidines as novel c-Jun N-terminal kinase (JNK) inhibitors. Bioorg Med Chem Lett. Jun. 15, 2007;17(12):3463-7. doi: 10.1016/j.bmcl.2007.03.078. Epub Mar. 30, 2007. PMID: 17459703.
Ferguson et al., Synthesis and structure activity relationships of a series of 4-amino-1H-pyrazoles as covalent inhibitors of CDK14. Bioorg Med Chem Lett. Aug. 1, 2019;29(15):1985-1993. doi: 10.1016/j.bmcl.2019.05.024. Epub May 23, 2019. With Supporting Information.
Roche et al., A new class of histamine H3 receptor antagonists derived from ligand based design. Bioorg Med Chem Lett. Jul. 1, 2007;17(13):3670-5. doi: 10.1016/j.bmcl.2007.04.056. Epub Apr. 25, 2007.
Zhang et al., Discovery of potent and selective covalent inhibitors of JNK. Chem Biol. Jan. 27, 2012;19(1):140-54. doi: 10.1016/j.chembiol.2011.11.010. Author Manuscript, 28 pages.
Desai et al., Effects of phosphorylation by CAK on cyclin binding by CDC2 and CDK2. Mol Cell Biol. Jan. 1995;15(1):345-50.

* cited by examiner

SEQUENCE LISTING

```
<160> NUMBER OF SEQ ID NOS: 3

<210> SEQ ID NO 1
<211> LENGTH: 346
<212> TYPE: PRT
<213> ORGANISM: Artificial Sequence
<220> FEATURE:
<223> OTHER INFORMATION: Synthetic polypeptide

<400> SEQUENCE: 1

Met Ala Leu Asp Val Lys Ser Arg Ala Lys Arg Tyr Glu Lys Leu Asp
1               5                   10                  15

Phe Leu Gly Glu Gly Gln Phe Ala Thr Val Tyr Lys Ala Arg Asp Lys
            20                  25                  30

Asn Thr Asn Gln Ile Val Ala Ile Lys Lys Ile Lys Leu Gly His Arg
        35                  40                  45

Ser Glu Ala Lys Asp Gly Ile Asn Arg Thr Ala Leu Arg Glu Ile Lys
    50                  55                  60

Leu Leu Gln Glu Leu Ser His Pro Asn Ile Ile Gly Leu Leu Asp Ala
65                  70                  75                  80

Phe Gly His Lys Ser Asn Ile Ser Leu Val Phe Asp Phe Met Glu Thr
                85                  90                  95

Asp Leu Glu Val Ile Ile Lys Asp Asn Ser Leu Val Leu Thr Pro Ser
            100                 105                 110

His Ile Lys Ala Tyr Met Leu Met Thr Leu Gln Gly Leu Glu Tyr Leu
        115                 120                 125

His Gln His Trp Ile Leu His Arg Asp Leu Lys Pro Asn Asn Leu Leu
    130                 135                 140

Leu Asp Glu Asn Gly Val Leu Lys Leu Ala Asp Phe Gly Leu Ala Lys
145                 150                 155                 160
```

Ser Phe Gly Ser Pro Asn Arg Ala Tyr Thr His Gln Val Val Thr Arg
            165                 170                 175

Trp Tyr Arg Ala Pro Glu Leu Leu Phe Gly Ala Arg Met Tyr Gly Val
            180                 185                 190

Gly Val Asp Met Trp Ala Val Gly Cys Ile Leu Ala Glu Leu Leu Leu
            195                 200                 205

Arg Val Pro Phe Leu Pro Gly Asp Ser Asp Leu Asp Gln Leu Thr Arg
            210                 215                 220

Ile Phe Glu Thr Leu Gly Thr Pro Thr Glu Glu Gln Trp Pro Asp Met
225                 230                 235                 240

Cys Ser Leu Pro Asp Tyr Val Thr Phe Lys Ser Phe Pro Gly Ile Pro
            245                 250                 255

Leu His His Ile Phe Ser Ala Ala Gly Asp Asp Leu Leu Asp Leu Ile
            260                 265                 270

Gln Gly Leu Phe Leu Phe Asn Pro Cys Ala Arg Ile Thr Ala Thr Gln
            275                 280                 285

Ala Leu Lys Met Lys Tyr Phe Ser Asn Arg Pro Gly Pro Thr Pro Gly
            290                 295                 300

Cys Gln Leu Pro Arg Pro Asn Cys Pro Val Glu Thr Leu Lys Glu Gln
305                 310                 315                 320

Ser Asn Pro Ala Leu Ala Ile Lys Arg Lys Arg Thr Glu Ala Leu Glu
            325                 330                 335

Gln Gly Gly Leu Pro Lys Lys Leu Ile Phe
            340                 345

<210> SEQ ID NO 2
<211> LENGTH: 1490
<212> TYPE: PRT
<213> ORGANISM: Artificial Sequence
<220> FEATURE:
<223> OTHER INFORMATION: Synthetic polypeptide

<400> SEQUENCE: 2

Met Pro Asn Ser Glu Arg His Gly Gly Lys Lys Asp Gly Ser Gly Gly
1               5                   10                  15

Ala Ser Gly Thr Leu Gln Pro Ser Gly Gly Gly Ser Ser Asn Ser
            20                  25                  30

Arg Glu Arg His Arg Leu Val Ser Lys His Lys Arg His Lys Ser Lys
            35                  40                  45

His Ser Lys Asp Met Gly Leu Val Thr Pro Glu Ala Ala Ser Leu Gly
        50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
            85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Leu Ser Ser Ser Lys Glu Ser Arg Ser
            165                 170                 175

```
Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
    210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
        260                 265                 270

Gln Ser Val Ser Pro Pro Tyr Lys Glu Pro Ser Ala Tyr Gln Ser Ser
            275                 280                 285

Thr Arg Ser Pro Ser Pro Tyr Ser Arg Arg Gln Arg Ser Val Ser Pro
        290                 295                 300

Tyr Ser Arg Arg Arg Ser Ser Ser Tyr Glu Arg Ser Gly Ser Tyr Ser
305                 310                 315                 320

Gly Arg Ser Pro Ser Pro Tyr Gly Arg Arg Ser Ser Ser Pro Phe
                325                 330                 335

Leu Ser Lys Arg Ser Leu Ser Arg Ser Pro Leu Pro Ser Arg Lys Ser
            340                 345                 350

Met Lys Ser Arg Ser Arg Ser Pro Ala Tyr Ser Arg His Ser Ser Ser
        355                 360                 365

His Ser Lys Lys Lys Arg Ser Ser Arg Ser Arg His Ser Ser Ile
370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Ala Lys Met Asp
                405                 410                 415

Gly Lys Glu Ser Lys Gly Ser Pro Val Phe Leu Pro Arg Lys Glu Asn
            420                 425                 430

Ser Ser Val Glu Ala Lys Asp Ser Gly Leu Glu Ser Lys Lys Leu Pro
        435                 440                 445

Arg Ser Val Lys Leu Glu Lys Ser Ala Pro Asp Thr Glu Leu Val Asn
450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                485                 490                 495

Ala Gln Gly Thr Arg Asp Ser Lys Pro Ile Ala Leu Lys Glu Glu Ile
            500                 505                 510

Val Thr Pro Lys Glu Thr Glu Thr Ser Glu Lys Glu Thr Pro Pro
        515                 520                 525

Leu Pro Thr Ile Ala Ser Pro Pro Leu Pro Thr Thr Thr Pro
        530                 535                 540

Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
                565                 570                 575

Pro Ala Ser Ser Thr Ser Thr Leu Pro Pro Ser Thr His Ser Lys Thr
        580                 585                 590

Ser Ala Val Ser Ser Gln Ala Asn Ser Gln Pro Pro Val Gln Val Ser
```

-continued

```
                595                 600                 605
Val Lys Thr Gln Val Ser Val Thr Ala Ala Ile Pro His Leu Lys Thr
610                 615                 620

Ser Thr Leu Pro Pro Leu Pro Leu Pro Pro Leu Leu Pro Gly Asp Asp
625                 630                 635                 640

Asp Met Asp Ser Pro Lys Glu Thr Leu Pro Ser Lys Pro Val Lys Lys
                645                 650                 655

Glu Lys Glu Gln Arg Thr Arg His Leu Leu Thr Asp Leu Pro Leu Pro
                660                 665                 670

Pro Glu Leu Pro Gly Gly Asp Leu Ser Pro Pro Asp Ser Pro Glu Pro
                675                 680                 685

Lys Ala Ile Thr Pro Pro Gln Gln Pro Tyr Lys Lys Arg Pro Lys Ile
690                 695                 700

Cys Cys Pro Arg Tyr Gly Glu Arg Arg Gln Thr Glu Ser Asp Trp Gly
705                 710                 715                 720

Lys Arg Cys Val Asp Lys Phe Asp Ile Ile Gly Ile Ile Gly Glu Gly
                725                 730                 735

Thr Tyr Gly Gln Val Tyr Lys Ala Lys Asp Lys Asp Thr Gly Glu Leu
                740                 745                 750

Val Ala Leu Lys Lys Val Arg Leu Asp Asn Glu Lys Glu Gly Phe Pro
                755                 760                 765

Ile Thr Ala Ile Arg Glu Ile Lys Ile Leu Arg Gln Leu Ile His Arg
770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
                820                 825                 830

Glu Asp His Ile Lys Ser Phe Met Lys Gln Leu Met Glu Gly Leu Glu
                835                 840                 845

Tyr Cys His Lys Lys Asn Phe Leu His Arg Asp Ile Lys Cys Ser Asn
850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Leu Gly Glu Glu Arg
                900                 905                 910

Tyr Thr Pro Ala Ile Asp Val Trp Ser Cys Gly Cys Ile Leu Gly Glu
                915                 920                 925

Leu Phe Thr Lys Lys Pro Ile Phe Gln Ala Asn Leu Glu Leu Ala Gln
930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
                965                 970                 975

Gln Tyr Arg Arg Arg Leu Arg Glu Glu Phe Ser Phe Ile Pro Ser Ala
                980                 985                 990

Ala Leu Asp Leu Leu Asp His Met Leu Thr Leu Asp Pro Ser Lys Arg
                995                1000                1005

Cys Thr Ala Glu Gln Thr Leu Gln Ser Asp Phe Leu Lys Asp Val
   1010                1015                1020
```

```
Glu Leu Ser Lys Met Ala Pro Pro Asp Leu Pro His Trp Gln Asp
    1025                1030                1035
Cys His Glu Leu Trp Ser Lys Lys Arg Arg Gln Arg Gln Ser
    1040                1045                1050
Gly Val Val Val Glu Pro Pro Pro Ser Lys Thr Ser Arg Lys
    1055                1060                1065
Glu Thr Thr Ser Gly Thr Ser Thr Glu Pro Val Lys Asn Ser Ser
    1070                1075                1080
Pro Ala Pro Pro Gln Pro Ala Pro Gly Lys Val Glu Ser Gly Ala
    1085                1090                1095
Gly Asp Ala Ile Gly Leu Ala Asp Ile Thr Gln Gln Leu Asn Gln
    1100                1105                1110
Ser Glu Leu Ala Val Leu Leu Asn Leu Leu Gln Ser Gln Thr Asp
    1115                1120                1125
Leu Ser Ile Pro Gln Met Ala Gln Leu Leu Asn Ile His Ser Asn
    1130                1135                1140
Pro Glu Met Gln Gln Gln Leu Glu Ala Leu Asn Gln Ser Ile Ser
    1145                1150                1155
Ala Leu Thr Glu Ala Thr Ser Gln Gln Gln Asp Ser Glu Thr Met
    1160                1165                1170
Ala Pro Glu Glu Ser Leu Lys Glu Ala Pro Ser Ala Pro Val Ile
    1175                1180                1185
Leu Pro Ser Ala Glu Gln Thr Thr Leu Glu Ala Ser Ser Thr Pro
    1190                1195                1200
Ala Asp Met Gln Asn Ile Leu Ala Val Leu Leu Ser Gln Leu Met
    1205                1210                1215
Lys Thr Gln Glu Pro Ala Gly Ser Leu Glu Glu Asn Asn Ser Asp
    1220                1225                1230
Lys Asn Ser Gly Pro Gln Gly Pro Arg Arg Thr Pro Thr Met Pro
    1235                1240                1245
Gln Glu Glu Ala Ala Ala Cys Pro Pro His Ile Leu Pro Pro Glu
    1250                1255                1260
Lys Arg Pro Pro Glu Pro Pro Gly Pro Pro Pro Pro Pro Pro Pro
    1265                1270                1275
Pro Pro Leu Val Glu Gly Asp Leu Ser Ser Ala Pro Gln Glu Leu
    1280                1285                1290
Asn Pro Ala Val Thr Ala Ala Leu Leu Gln Leu Leu Ser Gln Pro
    1295                1300                1305
Glu Ala Glu Pro Pro Gly His Leu Pro His Glu His Gln Ala Leu
    1310                1315                1320
Arg Pro Met Glu Tyr Ser Thr Arg Pro Arg Pro Asn Arg Thr Tyr
    1325                1330                1335
Gly Asn Thr Asp Gly Pro Glu Thr Gly Phe Ser Ala Ile Asp Thr
    1340                1345                1350
Asp Glu Arg Asn Ser Gly Pro Ala Leu Thr Glu Ser Leu Val Gln
    1355                1360                1365
Thr Leu Val Lys Asn Arg Thr Phe Ser Gly Ser Leu Ser His Leu
    1370                1375                1380
Gly Glu Ser Ser Ser Tyr Gln Gly Thr Gly Ser Val Gln Phe Pro
    1385                1390                1395
Gly Asp Gln Asp Leu Arg Phe Ala Arg Val Pro Leu Ala Leu His
    1400                1405                1410
```

```
Pro Val Val Gly Gln Pro Phe Leu Lys Ala Glu Gly Ser Ser Asn
    1415                1420                1425

Ser Val Val His Ala Glu Thr Lys Leu Gln Asn Tyr Gly Glu Leu
    1430                1435                1440

Gly Pro Gly Thr Thr Gly Ala Ser Ser Ser Gly Ala Gly Leu His
    1445                1450                1455

Trp Gly Gly Pro Thr Gln Ser Ser Ala Tyr Gly Lys Leu Tyr Arg
    1460                1465                1470

Gly Pro Thr Arg Val Pro Pro Arg Gly Gly Arg Gly Arg Gly Val
    1475                1480                1485

Pro Tyr
    1490

<210> SEQ ID NO 3
<211> LENGTH: 1512
<212> TYPE: PRT
<213> ORGANISM: Artificial Sequence
<220> FEATURE:
<223> OTHER INFORMATION: Synthetic polypeptide

<400> SEQUENCE: 3

Met Pro Ser Ser Ser Asp Thr Ala Leu Gly Gly Gly Gly Leu Ser
1               5                   10                  15

Trp Ala Glu Lys Lys Leu Glu Glu Arg Arg Lys Arg Arg Phe Leu
                20                  25                  30

Ser Pro Gln Gln Pro Pro Leu Leu Leu Pro Leu Leu Gln Pro Gln Leu
                35                  40                  45

Leu Gln Pro Pro Pro Pro Pro Pro Leu Leu Phe Leu Ala Ala Pro
    50                  55                  60

Gly Thr Ala Ala Ala Ala Ala Ala Ala Ala Ser Ser Ser Cys
65                  70                  75                  80

Phe Ser Pro Gly Pro Pro Leu Glu Val Lys Arg Leu Ala Arg Gly Lys
                85                  90                  95

Arg Arg Ala Gly Gly Arg Gln Lys Arg Arg Gly Pro Arg Ala Gly
                100                 105                 110

Gln Glu Ala Glu Lys Arg Arg Val Phe Ser Leu Pro Gln Pro Gln Gln
                115                 120                 125

Asp Gly Gly Gly Gly Ala Ser Ser Gly Gly Gly Val Thr Pro Leu Val
    130                 135                 140

Glu Tyr Glu Asp Val Ser Ser Gln Ser Glu Gln Gly Leu Leu Leu Gly
145                 150                 155                 160

Gly Ala Ser Ala Ala Thr Ala Ala Thr Ala Gly Gly Thr Gly Gly
                165                 170                 175

Ser Gly Gly Ser Pro Ala Ser Ser Gly Thr Gln Arg Arg Gly Glu
                180                 185                 190

Gly Ser Glu Arg Arg Pro Arg Arg Asp Arg Arg Ser Ser Gly Arg
                195                 200                 205

Ser Lys Glu Arg His Arg Glu His Arg Arg Arg Asp Gly Gln Arg Gly
    210                 215                 220

Gly Ser Glu Ala Ser Lys Ser Arg Ser Arg His Ser His Ser Gly Glu
225                 230                 235                 240

Glu Arg Ala Glu Val Ala Lys Ser Gly Ser Ser Ser Ser Gly Gly
                245                 250                 255

Arg Arg Lys Ser Ala Ser Ala Thr Ser Ser Ser Ser Ser Arg Lys
                260                 265                 270
```

```
Asp Arg Asp Ser Lys Ala His Arg Ser Arg Thr Lys Ser Ser Lys Glu
            275                 280                 285

Pro Pro Ser Ala Tyr Lys Glu Pro Pro Lys Ala Tyr Arg Glu Asp Lys
            290                 295                 300

Thr Glu Pro Lys Ala Tyr Arg Arg Arg Ser Leu Ser Pro Leu Gly
305                 310                 315                 320

Gly Arg Asp Asp Ser Pro Val Ser His Arg Ala Ser Gln Ser Leu Arg
                325                 330                 335

Ser Arg Lys Ser Pro Ser Pro Ala Gly Gly Ser Ser Pro Tyr Ser
            340                 345                 350

Arg Arg Leu Pro Arg Ser Pro Ser Pro Tyr Ser Arg Arg Arg Ser Pro
            355                 360                 365

Ser Tyr Ser Arg His Ser Ser Tyr Glu Arg Gly Gly Asp Val Ser Pro
            370                 375                 380

Ser Pro Tyr Ser Ser Ser Ser Trp Arg Arg Ser Arg Ser Pro Tyr Ser
385                 390                 395                 400

Pro Val Leu Arg Arg Ser Gly Lys Ser Arg Ser Arg Ser Pro Tyr Ser
                405                 410                 415

Ser Arg His Ser Arg Ser Arg Ser Arg His Arg Leu Ser Arg Ser Arg
            420                 425                 430

Ser Arg His Ser Ser Ile Ser Pro Ser Thr Leu Thr Leu Lys Ser Ser
            435                 440                 445

Leu Ala Ala Glu Leu Asn Lys Asn Lys Lys Ala Arg Ala Ala Glu Ala
            450                 455                 460

Ala Arg Ala Ala Glu Ala Ala Lys Ala Ala Glu Ala Thr Lys Ala Ala
465                 470                 475                 480

Glu Ala Ala Ala Lys Ala Ala Lys Ala Ser Asn Thr Ser Thr Pro Thr
                485                 490                 495

Lys Gly Asn Thr Glu Thr Ser Ala Ser Ala Ser Gln Thr Asn His Val
            500                 505                 510

Lys Asp Val Lys Lys Ile Lys Ile Glu His Ala Pro Ser Pro Ser Ser
            515                 520                 525

Gly Gly Thr Leu Lys Asn Asp Lys Ala Lys Thr Lys Pro Pro Leu Gln
            530                 535                 540

Val Thr Lys Val Glu Asn Asn Leu Ile Val Asp Lys Ala Thr Lys Lys
545                 550                 555                 560

Ala Val Ile Val Gly Lys Glu Ser Lys Ser Ala Ala Thr Lys Glu Glu
                565                 570                 575

Ser Val Ser Leu Lys Glu Lys Thr Lys Pro Leu Thr Pro Ser Ile Gly
            580                 585                 590

Ala Lys Glu Lys Glu Gln His Val Ala Leu Val Thr Ser Thr Leu Pro
            595                 600                 605

Pro Leu Pro Leu Pro Pro Met Leu Pro Glu Asp Lys Glu Ala Asp Ser
            610                 615                 620

Leu Arg Gly Asn Ile Ser Val Lys Ala Val Lys Lys Glu Val Glu Lys
625                 630                 635                 640

Lys Leu Arg Cys Leu Leu Ala Asp Leu Pro Leu Pro Pro Glu Leu Pro
                645                 650                 655

Gly Gly Asp Asp Leu Ser Lys Ser Pro Glu Glu Lys Lys Thr Ala Thr
            660                 665                 670

Gln Leu His Ser Lys Arg Arg Pro Lys Ile Cys Gly Pro Arg Tyr Gly
            675                 680                 685

Glu Thr Lys Glu Lys Asp Ile Asp Trp Gly Lys Arg Cys Val Asp Lys
```

```
          690             695             700
Phe Asp Ile Ile Gly Ile Ile Gly Glu Gly Thr Tyr Gly Gln Val Tyr
705             710             715             720

Lys Ala Arg Asp Lys Asp Thr Gly Glu Met Val Ala Leu Lys Lys Val
            725             730             735

Arg Leu Asp Asn Glu Lys Glu Gly Phe Pro Ile Thr Ala Ile Arg Glu
            740             745             750

Ile Lys Ile Leu Arg Gln Leu Thr His Gln Ser Ile Ile Asn Met Lys
            755             760             765

Glu Ile Val Thr Asp Lys Glu Asp Ala Leu Asp Phe Lys Lys Asp Lys
            770             775             780

Gly Ala Phe Tyr Leu Val Phe Glu Tyr Met Asp His Asp Leu Met Gly
785             790             795             800

Leu Leu Glu Ser Gly Leu Val His Phe Asn Glu Asn His Ile Lys Ser
            805             810             815

Phe Met Arg Gln Leu Met Glu Gly Leu Asp Tyr Cys His Lys Lys Asn
            820             825             830

Phe Leu His Arg Asp Ile Lys Cys Ser Asn Ile Leu Leu Asn Asn Arg
            835             840             845

Gly Gln Ile Lys Leu Ala Asp Phe Gly Leu Ala Arg Leu Tyr Ser Ser
            850             855             860

Glu Glu Ser Arg Pro Tyr Thr Asn Lys Val Ile Thr Leu Trp Tyr Arg
865             870             875             880

Pro Pro Glu Leu Leu Leu Gly Glu Arg Tyr Thr Pro Ala Ile Asp
            885             890             895

Val Trp Ser Cys Gly Cys Ile Leu Gly Glu Leu Phe Thr Lys Lys Pro
            900             905             910

Ile Phe Gln Ala Asn Gln Glu Leu Ala Gln Leu Glu Leu Ile Ser Arg
            915             920             925

Ile Cys Gly Ser Pro Cys Pro Ala Val Trp Pro Asp Val Ile Lys Leu
            930             935             940

Pro Tyr Phe Asn Thr Met Lys Pro Lys Lys Gln Tyr Arg Arg Lys Leu
945             950             955             960

Arg Glu Glu Phe Val Phe Ile Pro Ala Ala Leu Asp Leu Phe Asp
            965             970             975

Tyr Met Leu Ala Leu Asp Pro Ser Lys Arg Cys Thr Ala Glu Gln Ala
            980             985             990

Leu Gln Cys Glu Phe Leu Arg Asp Val Glu Pro Ser Lys Met Pro Pro
            995             1000            1005

Pro Asp Leu Pro Leu Trp Gln Asp Cys His Glu Leu Trp Ser Lys
            1010            1015            1020

Lys Arg Arg Arg Gln Lys Gln Met Gly Met Thr Asp Asp Val Ser
            1025            1030            1035

Thr Ile Lys Ala Pro Arg Lys Asp Leu Ser Leu Gly Leu Asp Asp
            1040            1045            1050

Ser Arg Thr Asn Thr Pro Gln Gly Val Leu Pro Ser Ser Gln Leu
            1055            1060            1065

Lys Ser Gln Gly Ser Ser Asn Val Ala Pro Val Lys Thr Gly Pro
            1070            1075            1080

Gly Gln His Leu Asn His Ser Glu Leu Ala Ile Leu Leu Asn Leu
            1085            1090            1095

Leu Gln Ser Lys Thr Ser Val Asn Met Ala Asp Phe Val Gln Val
            1100            1105            1110
```

```
Leu Asn Ile Lys Val Asn Ser Glu Thr Gln Gln Leu Asn Lys
1115                1120                1125

Ile Asn Leu Pro Ala Gly Ile Leu Ala Thr Gly Glu Lys Gln Thr
1130                1135                1140

Asp Pro Ser Thr Pro Gln Gln Glu Ser Ser Lys Pro Leu Gly Gly
1145                1150                1155

Ile Gln Pro Ser Ser Gln Thr Ile Gln Pro Lys Val Glu Thr Asp
1160                1165                1170

Ala Ala Gln Ala Ala Val Gln Ser Ala Phe Ala Val Leu Leu Thr
1175                1180                1185

Gln Leu Ile Lys Ala Gln Gln Ser Lys Gln Lys Asp Val Leu Leu
1190                1195                1200

Glu Glu Arg Glu Asn Gly Ser Gly His Glu Ala Ser Leu Gln Leu
1205                1210                1215

Arg Pro Pro Pro Glu Pro Ser Thr Pro Val Ser Gly Gln Asp Asp
1220                1225                1230

Leu Ile Gln His Gln Asp Met Arg Ile Leu Glu Leu Thr Pro Glu
1235                1240                1245

Pro Asp Arg Pro Arg Ile Leu Pro Pro Asp Gln Arg Pro Pro Glu
1250                1255                1260

Pro Pro Glu Pro Pro Val Thr Glu Glu Asp Leu Asp Tyr Arg
1265                1270                1275

Thr Glu Asn Gln His Val Pro Thr Thr Ser Ser Leu Thr Asp
1280                1285                1290

Pro His Ala Gly Val Lys Ala Ala Leu Leu Gln Leu Leu Ala Gln
1295                1300                1305

His Gln Pro Gln Asp Asp Pro Lys Arg Glu Gly Gly Ile Asp Tyr
1310                1315                1320

Gln Ala Gly Asp Thr Tyr Val Ser Thr Ser Asp Tyr Lys Asp Asn
1325                1330                1335

Phe Gly Ser Ser Ser Phe Ser Ser Ala Pro Tyr Val Ser Asn Asp
1340                1345                1350

Gly Leu Gly Ser Ser Ser Ala Pro Pro Leu Glu Arg Arg Ser Phe
1355                1360                1365

Ile Gly Asn Ser Asp Ile Gln Ser Leu Asp Asn Tyr Ser Thr Ala
1370                1375                1380

Ser Ser His Ser Gly Gly Pro Pro Gln Pro Ser Ala Phe Ser Glu
1385                1390                1395

Ser Phe Pro Ser Ser Val Ala Gly Tyr Gly Asp Ile Tyr Leu Asn
1400                1405                1410

Ala Gly Pro Met Leu Phe Ser Gly Asp Lys Asp His Arg Phe Glu
1415                1420                1425

Tyr Ser His Gly Pro Ile Ala Val Leu Ala Asn Ser Ser Asp Pro
1430                1435                1440

Ser Thr Gly Pro Glu Ser Thr His Pro Leu Pro Ala Lys Met His
1445                1450                1455

Asn Tyr Asn Tyr Gly Gly Asn Leu Gln Glu Asn Pro Ser Gly Pro
1460                1465                1470

Ser Leu Met His Gly Gln Thr Trp Thr Ser Pro Ala Gln Gly Pro
1475                1480                1485
```

```
Gly Tyr Ser Gln Gly Tyr Arg Gly His Ile Ser Thr Ser Thr Gly
    1490            1495                1500

Arg Gly Arg Gly Arg Gly Leu Pro Tyr
    1505            1510
```

INHIBITORS OF CYCLIN-DEPENDENT KINASE 12 (CDK12) AND USES THEREOF

RELATED APPLICATIONS

This application is a continuation of U.S. application Ser. No. 16/462,892, filed May 21, 2019, which is a national stage filing under 35 U.S.C. § 371 of international PCT application, PCT/US2017/063132, filed Nov. 22, 2017, which claims the benefit of and priority under 35 U.S.C. § 119(e) to U.S. Provisional Application, U.S. Ser. No. 62/425,519, filed Nov. 22, 2016, the contents of each of which is incorporated herein by reference in their entireties.

GOVERNMENT SUPPORT

This invention was made with government support under grant numbers R01 CA179483 awarded by The National Institutes of Health and W81XWH-16-1-0250 awarded by The Department of the Army. The government has certain rights in the invention.

BACKGROUND OF THE INVENTION

The members of the cyclin-dependent kinase (CDK) family play critical regulatory roles in proliferation. There are currently 20 known mammalian CDKs.

CDK12 and CDK13 were identified in cDNA screens for cell cycle regulators. Because their cyclin partners were not yet known, they were initially named CRKRS and CDC2L5 (Ko et al., *J. Cell Sci.*, 2001, 114, 2591-2603; Marquès et al., *Biochem Biophys Res Commun.*, 2000, 279(3):832-837), respectively. They were found to be 1490- and 1512-amino acid proteins, respectively, with a conserved central CTD kinase domain and degenerate RS domains identified in their N- and C-terminal regions (Even et al., *J Cell Biochem.*, 2006, 99(3), 890-904).

Evidence has shown CDK12 and CDK13 play an important role in cancer development. A comprehensive genomic approach identified CDK12 to be one of the most frequently somatically mutated genes in high-grade serous ovarian cancer, the most fatal form of the disease (Erratum, *Nature*, 2011, 474(7353), 609-615). Several identified point mutations in the kinase domain point to the critical importance of the kinase activity of CDK12 for the development/progression of this disease. CDK12 has also been found to contribute to the development of breast cancer. Notably, CDK12 is located on chromosome 17, within the 17q21 locus that contains several candidate genes for breast cancer susceptibility (Kauraniemi et al., *Cancer Res.*, 2001, 61(22), 8235-8240), and it is co-amplified with the tyrosine kinase receptor ERBB2, a protein amplified and overexpressed in about 20% of breast tumors. Gene fusion between CDK12 and ERBB2 was also detected in gastric cancer (Zang et al., *Cancer Res.*, 2011, 71(1), 29-39). CDK12 is also implicated in the modification of tamoxifen sensitivity in estrogen-positive breast cancer via the modulation of the mitogen-activated protein kinase pathway (Iorns et al., *Carcinogenesis*, 2009, 30(10):1696-1701).

Due to the important regulatory functions of kinases, such as CDK12, in cell cycle control, cell proliferation, differentiation, and apoptosis, it is important to develop modulators of the activities of these kinases, including selective modulators (e.g., selective inhibitors), for use as research tools as well as therapeutic agents in the treatment of diseases.

SUMMARY OF THE INVENTION

Cyclin dependent kinases (CDKs) (e.g., cyclin-dependent kinase 12 (CDK12)) are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. Most CDKs require the phosphorylation of a threonine residue located in the T-loop to achieve full kinase activity. This threonine residue is conserved in all CDKs that function in cell cycle regulation. CDK12 also plays a role in transcription and possibly in DNA repair. This suggests that the CDK12 enzyme complexes are involved in multiple functions in the cell, e.g., cell cycle control, apoptosis, transcription regulation, and DNA repair.

Cyclin-dependent kinase 12 (CDK12) is recognized as an elongation regulator of RNA polymerase II-mediated transcription through its kinase function of phosphorylation on CTD domain of RNA Pol II. However, the detailed mechanism is not clear, and the exact site of phosphorylation on CTD by CDK12 is still controversial. A genome-wide screening also identified CDK12/cyclin K playing a critical role in mediating genome stability via regulation of expression of DDR genes. The deletion of CDK12/cyclin K severely impaired the expression of several critical regulators of genome stability, such as BRCA1, ATR, FANCI, and FANCD2 proteins in cells. Furthermore, several mutations of CDK12 were already identified in a variety of tumors including ovary, breast, and prostate, and these alterations on CDK12 sensitized these tumors to DNA damage agents, such as cisplatin and its derivatives, and inhibitors of DNA repair, such as PARP inhibitors. Thus, CDK12 is a potential therapeutic target of drugs for cancers and other diseases. Cysteine 1039 on CDK12 is three residues away from CDK7 cysteine 312. Recently solved CDK12 structures show that cysteine 1039 is also targetable with a similar orientation as cysteine 312 on CDK7. Without wishing to be bound by any particular theory, the inventive compounds' selectivity for CDK12 may be due to the compounds' ability to covalently modify a specific cysteine residue of these kinases (e.g., Cys1039 of CDK12). In contrast to THZ1, these compounds however do not bind to cysteine 312 of CDK7 and also do not reversibly inhibit other CDKs. Without wishing to be bound by any particular theory, the irreversible inhibition of CDK12 by the inventive compounds results in prolonged disruption of transcription and induction of apoptosis of a diverse subset of cancer cell lines. Genome-wide transcript analysis following inhibitor treatment delineates CDK12-responsive genes important in the maintenance of the cancer cell state. Selective covalent inhibition of CDK12 may be a viable cancer therapeutic strategy.

The present invention provides compounds of Formulae (I') and (II), and pharmaceutically acceptable salts, solvates, hydrates, polymorphs, co-crystals, tautomers, stereoisomers, isotopically labeled derivatives, prodrugs, and compositions thereof. The compounds of Formulae (I') and (II), and pharmaceutically acceptable salts, solvates, hydrates, polymorphs, co-crystals, tautomers, stereoisomers, isotopically labeled derivatives, prodrugs, and compositions thereof, may inhibit the activity of a kinase. In certain embodiments, the kinase is a CDK. In certain embodiments, the kinase is CDK12. In certain embodiments, the compounds of Formulae (I') and (II) are selective for CDK12 compared to other kinases. The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., CDK12) and as therapeutics for the prevention and/or treatment of diseases associated with the overexpression and/or aberrant (e.g., increased) activity of a kinase (e.g., CDK12). In certain embodiments, the inventive compounds are used for the prevention and/or treatment of proliferative diseases (e.g., cancers (e.g., leukemia, lymphoma, melanoma, multiple myeloma, breast cancer, Ewing's sarcoma, osteosarcoma, brain cancer, neuroblastoma, lung cancer), benign neoplasms, angiogenesis, inflammatory diseases, autoinflammatory diseases, and autoimmune diseases) in a subject.

The present invention provides compounds of Formulae (I') and (II), and pharmaceutically acceptable salts, solvates, hydrates, polymorphs, co-crystals, tautomers, stereoisomers, isotopically labeled derivatives, prodrugs, and compositions thereof. The compounds of Formulae (I') and (II), and pharmaceutically acceptable salts, solvates, hydrates, polymorphs, co-crystals, tautomers, stereoisomers, isotopically labeled derivatives, prodrugs, and compositions thereof, may inhibit the activity of a kinase. The compounds described herein may in certain embodiments selectively inhibit specific CDK subtypes, for example, CDK12. In certain embodiments, the compounds of Formulae (I') and (II) are selective for CDK12 compared to other kinases. The present invention also provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., CDK12) and as therapeutics for the prevention and/or treatment of diseases associated with the overexpression and/or aberrant activity of a kinase (e.g., CDK12). In certain embodiments, the inventive compounds are used for the prevention and/or treatment of proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject.

In one aspect, the present invention provides compounds of Formula (I'):

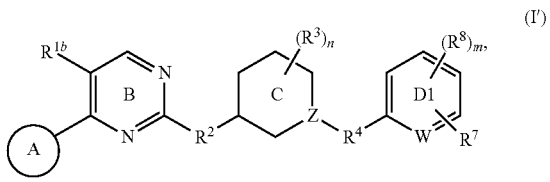

and pharmaceutically acceptable salts, solvates, hydrates, polymorphs, co-crystals, tautomers, stereoisomers, isotopically labeled derivatives, and prodrugs thereof, wherein Ring A, Z, W, $R^{1b}$, $R^2$, $R^3$, $R^4$, $R^7$, $R^8$, m, and n are as defined herein.

In one aspect, the present invention provides compounds of Formula (I):

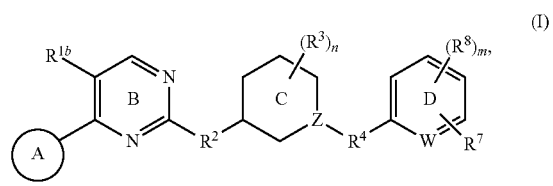

and pharmaceutically acceptable salts, solvates, hydrates, polymorphs, co-crystals, tautomers, stereoisomers, isotopically labeled derivatives, and prodrugs thereof, wherein Ring A, Z, $R^{1b}$, $R^2$, $R^3$, $R^4$, $R^7$, $R^8$, m, and n are as defined herein.

In one aspect, the present invention provides compounds of Formula (II):

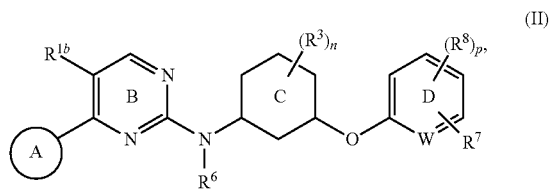

and pharmaceutically acceptable salts, solvates, hydrates, polymorphs, co-crystals, tautomers, stereoisomers, isotopically labeled derivatives, and prodrugs thereof, wherein Ring A, $R^{1b}$, $R^3$, $R^6$, $R^7$, $R^8$, n, and p are as defined herein.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating a proliferative disease in a subject in need thereof, preventing a proliferative disease in a subject in need thereof, inhibiting the activity of a protein kinase in a subject, biological sample, tissue, or cell, and/or inducing apoptosis in a cell. In certain embodiments, the proliferative disease is an inflammatory disease. In certain embodiments, the inflammatory disease is rheumatoid arthritis, Crohn's disease, or fibrosis.

In another aspect, the present invention provides methods for treating and/or preventing a proliferative disease. Exemplary proliferative diseases which may be treated include diseases associated with overexpression of a cyclin-dependent kinase (CDK), cancer, benign neoplasms, diseases associated with angiogenesis, inflammatory diseases, autoinflammatory diseases, and autoimmune diseases. In certain embodiments, the proliferative disease is cancer. In certain embodiments, the cancer is selected from the group consisting of pancreatic cancer, lung cancer (e.g., small cell lung cancer (SCLC), and non-small cell lung cancer), prostate cancer, breast cancer, ovarian cancer, kidney cancer, liver cancer, Ewing's sarcoma, osteosarcoma, brain cancer, neuroblastoma, and colorectal cancer. In certain embodiments, the proliferative disease is a benign neoplasm or disease associated with angiogenesis. In certain embodiments, the proliferative disease is an autoinflammatory disease. In certain embodiments, the proliferative disease is an autoimmune disease.

Another aspect of the invention relates to methods of inhibiting the activity of a kinase (e.g., CDK (e.g., CDK12))

using a compound described herein in a biological sample or subject. In certain embodiments, the method involves the selective inhibition of CDK12.

Also provided by the present invention are methods of inhibiting the transcription of one or more genes in the cell of a biological sample or subject using a compound described herein. The transcription of genes affected by the activity of CDK12 may be inhibited by a compound of the invention. In certain embodiments, these genes are one or more selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, and EWS-FLI.

The present invention also provides methods of inhibiting cell growth in a biological sample or subject. In still another aspect, the present invention provides methods of inducing apoptosis of a cell in a biological sample or subject.

The present invention provides methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent. The methods described herein may further include performing radiotherapy, immunotherapy, and/or transplantation on the subject.

In yet another aspect, the present invention provides compounds of Formulae (I') and (II), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., a proliferative disease such as cancer) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-4}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^AH(C^BH_2C^CH_3)$— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH($C_2H_5$)— is a $C_1$ hydrocarbon chain, and

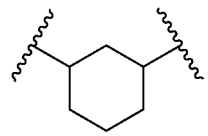 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C=C=$CH_2$—, and —C≡C—CH=CH— are all examples of a unsubstituted and unsaturated hydrocarbon chain. In certain embodiments, the hydrocarbon chain is unsubstituted (e.g., —$(CH_2)_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

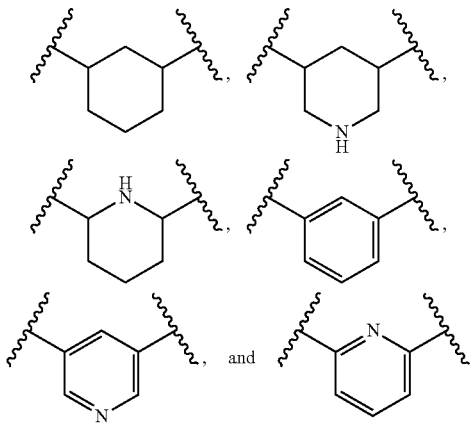

are all examples of a hydrocarbon chain. In contrast, in certain embodiments

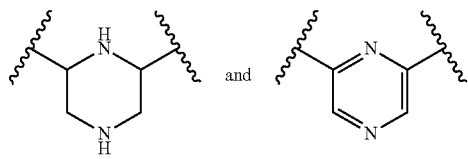 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("C$_{1-20}$ alkyl"). In some embodiments, an alkyl group has 1 to 10 carbon atoms ("C$_{1-10}$ alkyl"). In some embodiments, an alkyl group has 1 to 9 carbon atoms ("C$_{1-9}$ alkyl"). In some embodiments, an alkyl group has 1 to 8 carbon atoms ("C$_{1-8}$ alkyl"). In some embodiments, an alkyl group has 1 to 7 carbon atoms ("C$_{1-7}$ alkyl"). In some embodiments, an alkyl group has 1 to 6 carbon atoms ("C$_{1-6}$ alkyl"). In some embodiments, an alkyl group has 1 to 5 carbon atoms ("C$_{1-5}$ alkyl"). In some embodiments, an alkyl group has 1 to 4 carbon atoms ("C$_{1-4}$ alkyl"). In some embodiments, an alkyl group has 1 to 3 carbon atoms ("C$_{1-3}$ alkyl"). In some embodiments, an alkyl group has 1 to 2 carbon atoms ("C$_{1-2}$ alkyl"). In some embodiments, an alkyl group has 1 carbon atom ("C$_1$ alkyl"). In some embodiments, an alkyl group has 2 to 6 carbon atoms ("C$_{2-6}$ alkyl"). Examples of C$_{1-6}$ alkyl groups include methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), and n-hexyl (C$_6$). Additional examples of alkyl groups include n-heptyl (C$_7$), n-octyl (C$_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted C$_{1-10}$ alkyl (e.g., —CH$_3$). In certain embodiments, the alkyl group is substituted C$_{1-10}$ alkyl.

"Alkenyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_2$-6 alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_2$-6 alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and $_{ww}$ero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_3$-8 carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{aa}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^f$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$—C(=NR$^{X1}$)OR$^{X1}$—C(=NR$^{X1}$)SR$^{X1}$ and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{aa}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_3$-10 carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups, such as carbamate groups (e.g., —C(=O)OR$^{aa}$), include, but are not limited to, methyl carbamate, ethyl carbamate, 9-fluorenylmethyl carbamate (Fmoc), 9-(2-sulfo)fluorenylmethyl carbamate, 9-(2, 7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Teroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups, such as sulfonamide groups (e.g., —S(=O)$_2$R$^{aa}$), include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)N$(R^{bb})_2$, —C(=N$R^{bb}$)$R^{aa}$, —C(=N$R^{bb}$)$OR^{aa}$, —C(=N$R^{bb}$)N$(R^{bb})_2$, —S(=O)$R^{aa}$, —$SO_2R^{aa}$, —Si$(R^{aa})_3$, —P$(R^{cc})_2$, —P$(R^{cc})_3^+X^-$, —P$(OR^{cc})_2$, —P$(OR^{cc})_3^+X^-$, —P(=O)$(R^{aa})_2$, —P(=O)$(OR^{cc})_2$, and —P(=O)$(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=N$R^{bb}$)$R^{aa}$, —C(=N$R^{bb}$)$OR^{aa}$, —C(=N$R^{bb}$)$N(R^{bb})_2$, —S(=O)$R^{aa}$, —$SO_2R^{aa}$, —Si$(R^{aa})_3$, —P$(R^{cc})_2$, —P$(R^{cc})_3^+X^-$, —P$(OR^{cc})_2$, —P$(OR^{cc})_3^+X^-$, —P(=O)$(R^{aa})_2$, —P(=O) $(OR^{cc})_2$, and —P(=O)$(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March's Advanced Organic Chemistry 6th ed. (501-502). Exemplary leaving groups include, but are not limited to, halo (e.g., chloro, bromo, iodo) and activated substituted hydroxyl groups (e.g., —OC(=O)$SR^{aa}$, —OC(=O)$R^{aa}$, —$OCO_2Ra$, —OC(=O)$N(R^{bb})_2$, —OC(=N$R^{bb}$)$R^{aa}$, —OS(=O)$R^{aa}$, —OC(=N$R^{bb}$)$OR^{aa}$, —OC(=N$R^{bb}$) $N(R^{bb})_2$, —$OS(=O)R^{aa}$, —$OSO_2R^{aa}$, —$OP(R^{cc})_2$, —OP$(R^{cc})_3$, —OP(=O)$_2R^{aa}$, —OP(=O)$(R^{aa})_2$, —OP(=O) $(OR^{cc})_2$, —OP(=O)$_2N(R^{bb})_2$, and —OP(=O)$(NR^{bb})_2$, wherein $R^{aa}$, $R^{bb}$, and $R^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference.

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulae (I') and (II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers".

When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formulae (I') and (II), which have cleavable groups and become by solvolysis or under physiological conditions the compounds of Formulae (I') and (II) which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formulae (I') and (II) may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formula (I') or (II) refers to an amount sufficient to elicit the desired biological response, i.e., treating the condition. As will be appreciated by those of ordinary skill in this art, the effective amount of a compound of Formula (I') or (II) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I') or (II) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I') or (II) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angio-immunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

An "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

A "protein" or "peptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

The term "kinase" refers to any enzyme that catalyzes the addition of phosphate groups to an amino acid residue of a substrate (e.g., a protein or nucleoside). For example, a serine kinase catalyzes the addition of a phosphate group to serine residue in a protein. In certain embodiments, the kinase is a protein kinase. Examples of kinases include, but are not limited to, a CMGC kinase (e.g., a cyclin-dependent kinase (CDK, e.g., CDK1, CDK2, CDK2, CDK4, CDK5, CDK7, CDK8, CDK9, CDK10, CDK11, CDK12, CDK13, CDK14, CDK16, CDK20), a mitogen-activated protein kinase (MAPK, e.g., MAPK1, MAPK3, MAPK4, MAPK6, MAPK7, MAPK8, MAPK9, MAPK10, MAPK11, MAPK12, MAPK13, MAPK14, MAPK15), a glycogen synthase kinase 3 (GSK3, e.g., GSK3α, GSK3β), or a CDC-like kinase (CLK, e.g., CLK1, CLK2, CLK3, CLK4)), an AGC kinase (e.g., protein kinase A (PKA), protein kinase C (PKC), protein kinase G (PKG)), a $Ca^{2+}$/calmodulin-dependent protein kinase (CaM kinase, e.g., a specialized CaM kinase, a multifunctional CaM kinase), a casein kinase 1 (CK1, e.g., CK1alpha, CK1beta 1, CK1gamma 1, CK1gamma 2, CK1gamma 3, CK1delta, CK1epsilon), a STE kinase (e.g., a homolog of yeast Sterile 7, Sterile 11, or Sterile 20 kinase), a tyrosine kinase (TK, e.g., a receptor tyrosine kinase (RTK), a non-receptor tyrosine kinase (nRTK)), and a tyrosine-kinase-like kinase (TKL, e.g., a mixed lineage kinase (MLK), RAF, a serine threonine kinase receptor (STKR), a leucine rich repeat kinase (LRRK), a LIM domain kinase (LIMK), a testis expressed serine kinase (TESK), an IL1 receptor associated kinase (IRAK), a receptor interacting protein kinase (RIPK)).

The term "CDK" refers to a cyclin-dependent kinase. A CDK binds a cyclin (e.g., Cyclin H), which is a regulatory protein. CDKs phosphorylate their substrates at serines and threonines. The consensus sequence for the phosphorylation site in the amino acid sequence of a CDK substrate is [S/T*]PX[K/R], where S/T* is the phosphorylated serine or threonine, P is proline, X is any amino acid, K is lysine, and R is arginine. CDKs include CDK1, CDK2, CDK2, CDK4, CDK5, CDK7, CDK8, CDK9, CDK10, CDK11, CDK12, CDK14, CDK16, and CDK20.

CDK7, cyclin-dependent kinase 7, is a CDK, wherein the substrate is Cyclin H, MAT1 (e.g., MNAT1), or Cyclin H and MAT1. CDK7 is alternatively referred to as CAK1, HCAK, MO15, STK1, CDKN7, and p39MO15. Non-limiting examples of the nucleotide and protein sequences for human CDK7 are described in GenBank Accession Number: NP_001790, incorporated herein by reference. The amino acid sequence of this CDK7 is as follows:

(SEQ ID NO: 1)
MALDVKSRAKRYEKLDFLGEGQFATVYKARDKNTNQIVAIKKIKLGHRSEA

KDGINRTALREIKLLQELSHPNIIGLLDAFGHKSNISLVFDFMETDLEVII

KDNSLVLTPSHIKAYMLMTLQGLEYLHQHWILHRDLKPNNLLLDENGVLKL

ADFGLAKSFGSPNRAYTHQVVTRWYRAPELLFGARMYGVGVDMWAVGCILA

ELLLRVPFLPGDSDLDQLTRIFETLGTPTEEQWPDMCSLPDYVTFKSFPGI

PLHHIFSAAGDDLLDLIQGLFLFNPCARITATQALKMKYFSNRPGPTPGCQ

LPRPNCPVETLKEQSNPALAIKRKRTEALEQGGLPKKLIF

CDK12, cyclin-dependent kinase 12, is a CDK, wherein the substrate is Cyclin K or flavopiridol. CDK12 is alternatively referred to as Cdc2-related kinase, CDC2-related protein kinase 7, Cell division cycle 2-related protein kinase 7, Cell division protein kinase 12, CRK7, CRKR, CRKRS, cyclin-dependent kinase 12, or KIAA0904. Non-limiting examples of the nucleotide and protein sequences for human CDK12 are described in Uniprot Number: Q9NYV4, which is incorporated herein by reference. The amino acid sequence of this CDK12 is as follows:

(SEQ ID NO: 2)
MPNSERHGGKKDGSGGASGTLQPSSGGGSSNSRERHRLVSKHKRHKSKHSK

DMGLVTPEAASLGTVIKPLVEYDDISSDSDTFSDDMAFKLDRRENDERRGS

DRSDRLHKHRHHQHRRSRDLLKAKQTEKEKSQEVSSKSGSMKDRISGSSKR

SNEETDDYGKAQVAKSSSKESRSSKLHKEKTRKERELKSGHKDRSKSHRKR

ETPKSYKTVDSPKRRSRSPHRKWSDSSKQDDSPSGASYGQDYDLSPSRSHT

SSNYDSYKKSPGSTSRRQSVSPPYKEPSAYQSSTRSPSPYSRRQRSVSPYS

RRRSSSYERSGSYSGRSPSPYGRRRSSSPFLSKRSLSRSPLPSRKSMKSRS

RSPAYSRHSSSHSKKKRSSSRSRHSSISPVRLPLNSSLGAELSRKKKERAA

AAAAAKMDGKESKGSPVFLPRKENSSVEAKDSGLESKKLPRSVKLEKSAPD

TELVNVTHLNTEVKNSSDTGKVKLDENSEKHLVKDLKAQGTRDSKPIALKE

EIVTPKETETSEKETPPPLPTIASPPPPLPTTTPPPQTPPLPPLPPIPALP

QQPPLPPSQPAFSQVPASSTSTLPPSTHSKTSAVSSQANSQPPVQVSVKTQ

VSVTAAIPHLKTSTLPPLPLPPLLPGDDDMDSPKETLPSKPVKKEKEQRTR

HLLTDLPLPPELPGGDLSPPDSPEPKAITPPQQPYKKRPKICCPRYGERRQ

TESDWGKRCVDKFDIIGIIGEGTYGQVYKAKDKDTGELVALKKVRLDNEKE

GFPITAIREIKILRQLIHRSVVNMKEIVTDKQDALDFKKDKGAFYLVFEYM

DHDLMGLLESGLVHFSEDHIKSFMKQLMEGLEYCHKKNFLHRDIKCSNILL

NNSGQIKLADFGLARLYNSEESRPYTNKVITLWYRPPELLLGEERYTPAID

VWSCGCILGELFTKKPIFQANLELAQLELISRLCGSPCPAVWPDVIKLPYF

NTMKPKKQYRRRLREEFSFIPSAALDLLDHMLTLDPSKRCTAEQTLQSDFL

KDVELSKMAPPDLPHWQDCHELWSKKRRRQRQSGVVVEEPPPSKTSRKETT

SGTSTEPVKNSSPAPPQPAPGKVESGAGDAIGLADITQQLNQSELAVLLNL

LQSQTDLSIPQMAQLLNIHSNPEMQQQLEALNQSISALTEATSQQQDSETM

APEESLKEAPSAPVILPSAEQTTLEASSTPADMQNILAVLLSQLMKTQEPA

GSLEENNSDKNSGPQGPRRTPTMPQEEAAACPPHILPPEKRPPEPPGPPPP

PPPPPLVEGDLSSAPQELNPAVTAALLQLLSQPEAEPPGHLPHEHQALRPM

EYSTRPRPNRTYGNTDGPETGFSAIDTDERNSGPALTESLVQTLVKNRTFS

GSLSHLGESSSYQGTGSVQFPGDQDLRFARVPLALHPVVGQPFLKAEGSSN

SVVHAETKLQNYGELGPGTTGASSSGAGLHWGGPTQSSAYGKLYRGPTRVP

PRGGRGRGVPY

CDK13, cyclin-dependent kinase 13, is a CDK, wherein the relevant cyclin is cyclin K and a reference inhibitor is the pan-CDK inhibitor flavopiridol and the c-terminal domain (CTD) of RNA-polymerase II is a physiological substrate. CDK13 is alternatively referred to as CHED; CDC2L; CDC2L5; or hCDK13. Non-limiting examples of the nucleotide and protein sequences for human CDK12 are described in GenBank Accession Number M80629, which is incorporated herein by reference. The amino acid sequence of this CDK13 is as follows:

(SEQ ID NO: 3)
MPSSSDTALGGGGGLSWAEKKLEERRKRRRFLSPQQPPLLLPLLQPQLLQP

PPPPPPLLFLAAPGTAAAAAAAAASSSCFSPGPPLEVKRLARGKRRAGGR

QKRRRGPRAGQEAEKRRVFSLPQPQQDGGGGASSGGGVTPLVEYEDVSSQS

EQGLLLGGASAATAATAAGGTGGSGGSPASSSGTQRRGEGSERRPRRDRRS

SSGRSKERHREHRRRDGQRGGSEASKSRSRHSHSGEERAEVAKSGSSSSSG

GRRKSASATSSSSSSRKDRDSKAHRSRTKSSKEPPSAYKEPPKAYREDKTE

PKAYRRRRSLSPLGGRDDSPVSHRASQSLRSRKSPSPAGGGSSPYSRRLPR

SPSPYSRRRSPSYSRHSSYERGGDVSPSPYSSSSWRRSRSPYSPVLRRSGK

SRSRSPYSSRHSRSRSRHRLSRSRSRHSSISPSTLTLKSSLAAELNKNKKA

RAAEAARAAEAAKAAEATKAAEAAAKAAKASNTSTPTKGNTETSASASQTN

HVKDVKKIKIEHAPSPSSGGTLKNDKAKTKPPLQVTKVENNLIVDKATKKA

VIVGKESKSAATKEESVSLKEKTKPLTPSIGAKEKEQHVALVTSTLPPLPL

PPMLPEDKEADSLRGNISVKAVKKEVEKKLRCLLADLPLPPELPGGDDLSK

SPEEKKTATQLHSKRRPKICGPRYGETKEKDIDWGKRCVDKFDIIGIIGEG

TYGQVYKARDKDTGEMVALKKVRLDNEKEGFPITAIREIKILRQLTHQSII

NMKEIVTDKEDALDFKKDKGAFYLVFEYMDHDLMGLLESGLVHFNENHIKS

FMRQLMEGLDYCHKKNFLHRDIKCSNILLNNRGQIKLADFGLARLYSSEES

RPYTNKVITLWYRPPELLLGEERYTPAIDVWSCGCILGELFTKKPIFQANQ

ELAQLELISRICGSPCPAVWPDVIKLPYFNTMKPKKQYRRKLREEFVFIPA

AALDLFDYMLALDPSKRCTAEQALQCEFLRDVEPSKMPPPDLPLWQDCHEL

WSKKRRRQKQMGMTDDVSTIKAPRKDLSLGLDDSRTNTPQGVLPSSQLKSQ

GSSNVAPVKTGPGQHLNHSELAILLNLLQSKTSVNMADFVQVLNIKVNSET

QQQLNKINLPAGILATGEKQTDPSTPQQESSKPLGGIQPSSQTIQPKVETD

AAQAAVQSAFAVLLTQLIKAQQSKQKDVLLEERENGSGHEASLQLRPPPEP

STPVSGQDDLIQHQDMRILELTPEPDRPRILPPDQRPPEPPEPPPVTEEDL

DYRTENQHVPTTSSSLTDPHAGVKAALLQLLAQHQPQDDPKREGGIDYQAG

DTYVSTSDYKDNFGSSSFSSAPYVSNDGLGSSSAPPLERRSFIGNSDIQSL

DNYSTASSHSGGPPQPSAFSESFPSSVAGYGDIYLNAGPMLFSGDKDHRFE

YSHGPIAVLANSSDPSTGPESTHPLPAKMHNYNYGGNLQENPSGPSLMHGQ

TWTSPAQGPGYSQGYRGHISTSTGRGRGRGLPY

BRIEF DESCRIPTION OF THE DRAWINGS

The accompanying drawings, which constitute a part of this specification, illustrate several embodiments of the invention and together with the description, serve to explain the principles of the invention.

Jurkat cells were treated with THZ1 (1 µM), compound BSJ-01-175-1 (1 µM), or DMSO vehicle control for 6 hrs. Clarified cellular lysates from each treatment condition were then incubated with either 1 µM THZ1-biotin, a concentration that binds CDK7-cyclin H, CDK12-cyclin K, and CDK13-cyclin K complexes. Lysates were incubated with THZ1-biotin overnight at 4 degrees Celsius. Subsequent addition of streptavidin-coated beads permits the immunoprecipitation of the indicated protein complexes. Following washing of beads with lysis buffer, the immunoprecipitated proteins were eluted from the beads by boiling in SDS buffer. Western blotting for cyclin K was used to identify precipitated CDK12-cyclin K or CDK13-cyclin K complexes. Western blotting for cyclin H was used to identify precipitated CDK7-cyclin H complexes. As THZ1 and compound BSJ-01-175-1 bind to their intended targets covalently, pretreatment of cells with these compounds would be expected to block subsequent capture and immunoprecipitation of these protein complexes with THZ1-biotin. The western blot data indicates that THZ1 binds intracellular CDK12-cyclin K, CDK13-cyclin K and CDK7-cyclin H complexes, while compound BSJ-01-175-1 binds intracellular CDK12-cyclin K and CDK13-cyclin K complexes selectively (and not CDK7-cyclin H).

Figure 2:
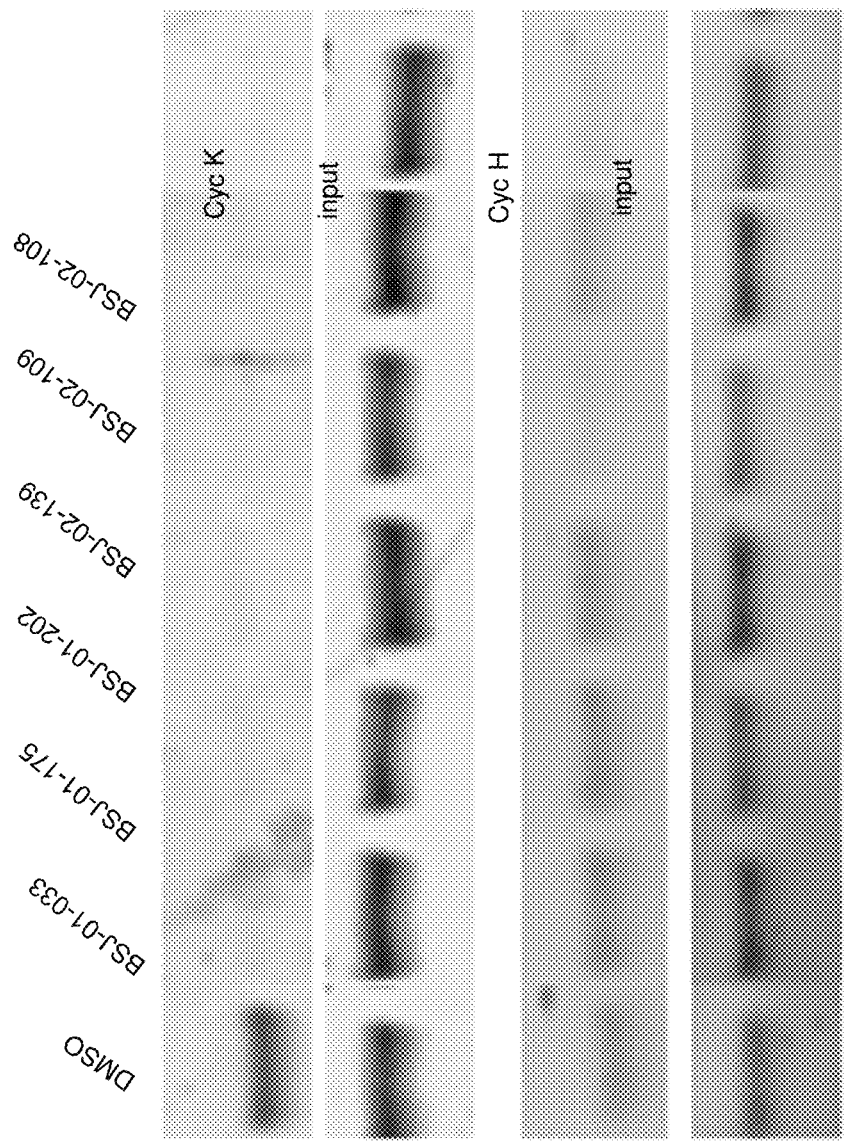

FIG. 2 shows inhibition of Jurkat cell viability by exemplified compounds at a concentration of 1.0 µM for 6 hours, followed by lysing and pulldown with Biotin-THZ1, and subsequent blot for cyclin K (Cyc K) and cyclin H (Cyc H). Compounds BSJ-01-033, BSJ-01-175, BSJ-01-202, BSJ-02-139, BSJ-02-109 and BSJ-02-108 show a loss in cyclin K pulldown, indicating loss of CDK12 binding and BSJ-02-139 and BSJ-02-108 also show a loss in cyclin H pulldown, indicating loss of CDK7 binding.

Figure 3:
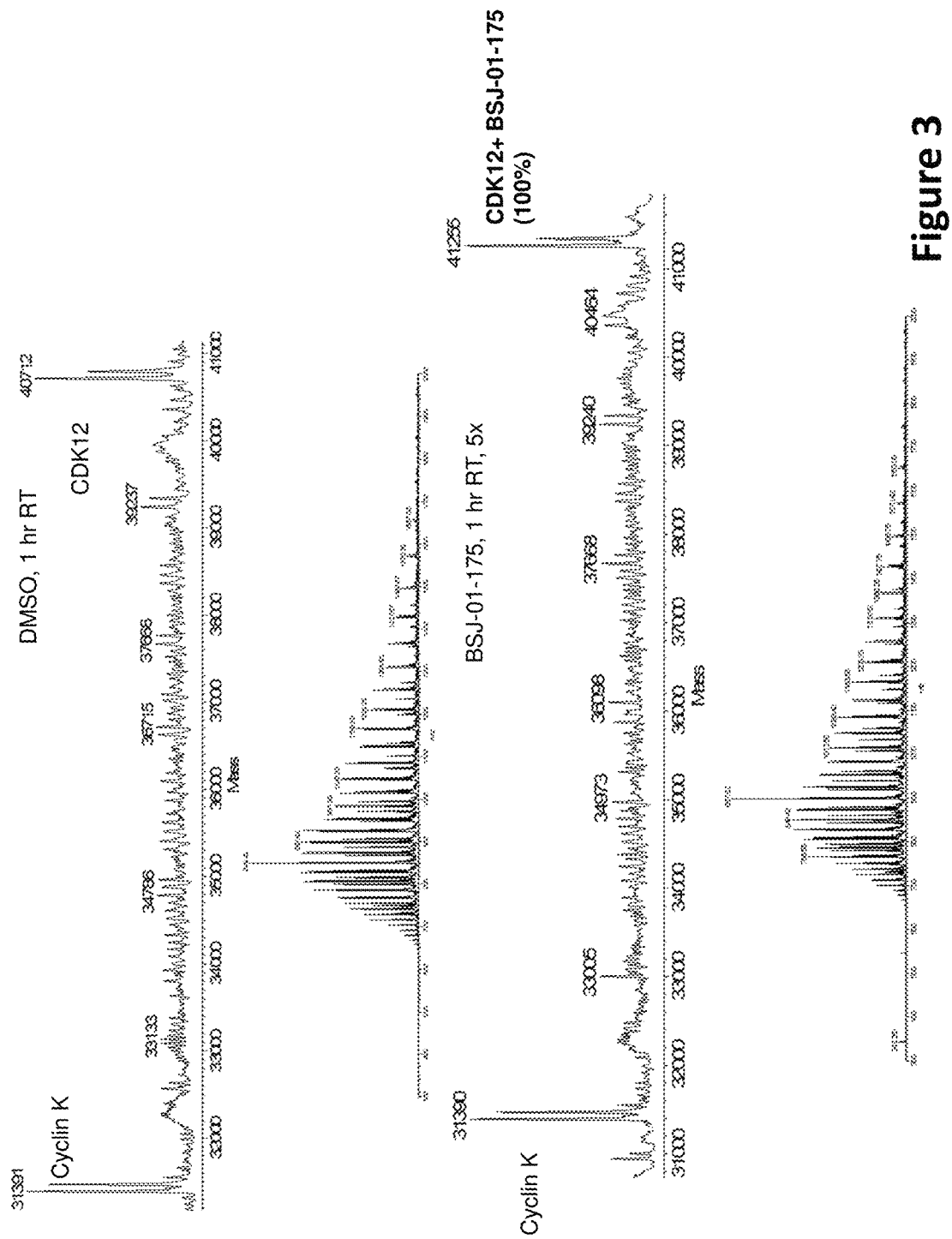

FIG. 3. shows exemplary mass spectrum labeling of CDK12 with compound BSJ-01-175. Compound BSJ-01-175 is able to label CDK12 once treated with a 5-fold excess of compound BSJ-01-175 for 1 hour at room temperature.

DETAILED DESCRIPTION OF CERTAIN EMBODIMENTS OF THE INVENTION

The present invention provides compounds, which inhibit the activity of a kinase, for the prevention and/or treatment of a proliferative disease of a subject. In certain embodiments, the inventive compounds inhibit the activity of cyclin-dependent kinase (CDK). In certain embodiments, the inventive compounds inhibit the activity of cyclin-dependent kinase 12 (CDK12). The present invention further provides methods of using the compounds described herein, e.g., as biological probes to study the inhibition of the activity of a kinase (e.g., CDK (e.g., CDK12)), and as therapeutics, e.g., in the prevention and/or treatment of diseases associated with the overexpression and/or aberrant activity of the kinase (e.g., CDK (e.g., CDK12)). In certain embodiments, the diseases are proliferative diseases. The proliferative diseases include, but are not limited to, cancer (e.g., leukemia, melanoma, multiple myeloma), benign neoplasm, angiogenesis, inflammatory diseases, autoinflammatory diseases, and autoimmune diseases. In certain embodiments, the cancer is associated with the overexpression and/or aberrant activity of a kinase (e.g., CDK (e.g., CDK12)). Also provided by the present disclosure are pharmaceutical compositions, kits, methods, and uses of a compound of Formulae (I') or (II) as described herein.

Compounds

In certain embodiments, a compound described herein is a compound of any one of Formulae (I') and (II), or a pharmaceutically acceptable salt, solvate, hydrate, polymorph, co-crystal, tautomer, stereoisomer, isotopically labeled derivative, or prodrug thereof.

In one aspect of the present invention, provided are compounds of Formula (I'):

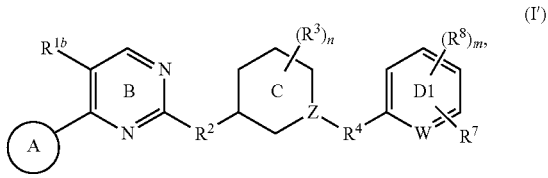

(I')

and pharmaceutically acceptable salts, solvates, hydrates, tautomers, and stereoisomers thereof, wherein:

Ring A is an optionally substituted heteroaryl ring of any one of the Formulae (ii-1)-(ii-5):

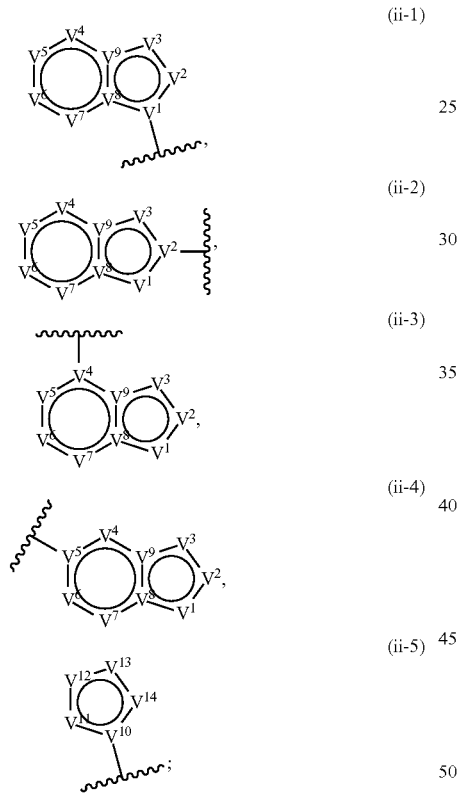

or an optionally substituted 6-membered aryl or heteroaryl ring;

each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, and $V^{14}$ is independently O, S, N, N($R^{A1}$), C, or C($R^{A2}$);

Z is —CH— or —N—;

each instance of $R^{A1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each instance of $R^{A2}$ is independently selected from hydrogen, halogen, —CN, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A2a}$, —N(R$^{A2b}$)$_2$, and —SR$^{A2a}$, wherein R$^{A2a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of R$^{A2b}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of R$^{A2b}$ are taken together with their intervening atoms to form a substituted or unsubstituted heterocyclic or substituted or unsubstituted heteroaryl ring; or any two R$^{A1}$, any two R$^{A2}$, or one R$^{A1}$ and one R$^{A2}$ are joined to form an optionally substituted carbocyclic, optionally substituted heterocyclic, optionally substituted aryl, or optionally substituted heteroaryl ring;

each of R$^{1b}$ is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{B1a}$, —N(R$^{B1b}$)$_2$, and —SR$^{B1a}$ wherein each occurrence of R$^{B1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom, wherein each occurrence of R$^{B1b}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of R$^{B1b}$ are taken together with their intervening atoms to form a substituted or unsubstituted heterocyclic or substituted or unsubstituted heteroaryl ring;

R$^2$ is —O—, —S—, —N(R$^6$)—, or an optionally substituted $C_1$-$C_4$ alkylene, wherein one or more methylene units of the alkylene are optionally and independently replaced with —O—, —S—, or —N(R$^6$)—;

each instance of R$^3$, if present, is independently selected from halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{C1}$, —N(R$^{C1a}$)$_2$, and —SR$^{C1}$, wherein each occurrence of R$^{C1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of $R^{C1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of $R^{C1a}$ are taken together with their intervening atoms to form a substituted or unsubstituted heterocyclic or substituted or unsubstituted heteroaryl ring; or two $R^3$ groups bound to the same ring carbon atom are taken together to form =O, or two $R^3$ groups bound to the same or different ring carbon atoms are joined to form an optionally substituted carbocyclyl, optionally substituted heterocyclyl, optionally substituted aryl, or optionally substituted heteroaryl ring;

$R^4$ is selected from a bond, —C(=O)—, —O—, —S—, —N($R^6$)—, —S(=O)$_2$—, and optionally substituted $C_1$-$C_4$ alkylene, wherein:

one or more methylene units of the alkylene other than a methylene unit bound to a nitrogen atom is optionally and independently replaced with —C(=O), —O—, —S—, —N($R^6$)—, or —S(=O)$_2$—;

each $R^6$ is independently selected from hydrogen and —$C_1$-$C_6$ alkyl;

$R^7$ is a warhead of formula:

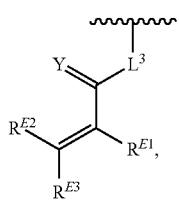
(i-1)

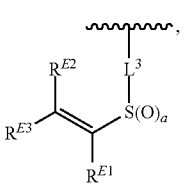
(i-2)

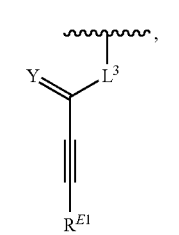
(i-3)

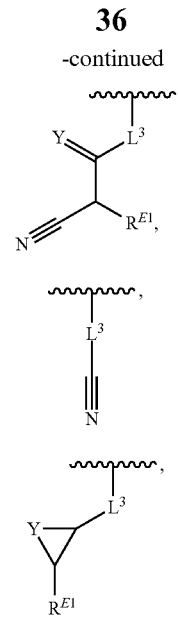
(i-4)

(i-5)

(i-6)

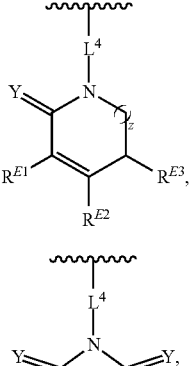
(i-7)

(i-8)

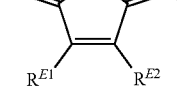
(i-9)

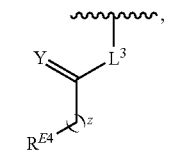
(i-10)

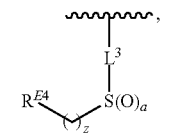
(i-11)

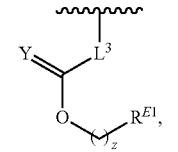
(i-12)

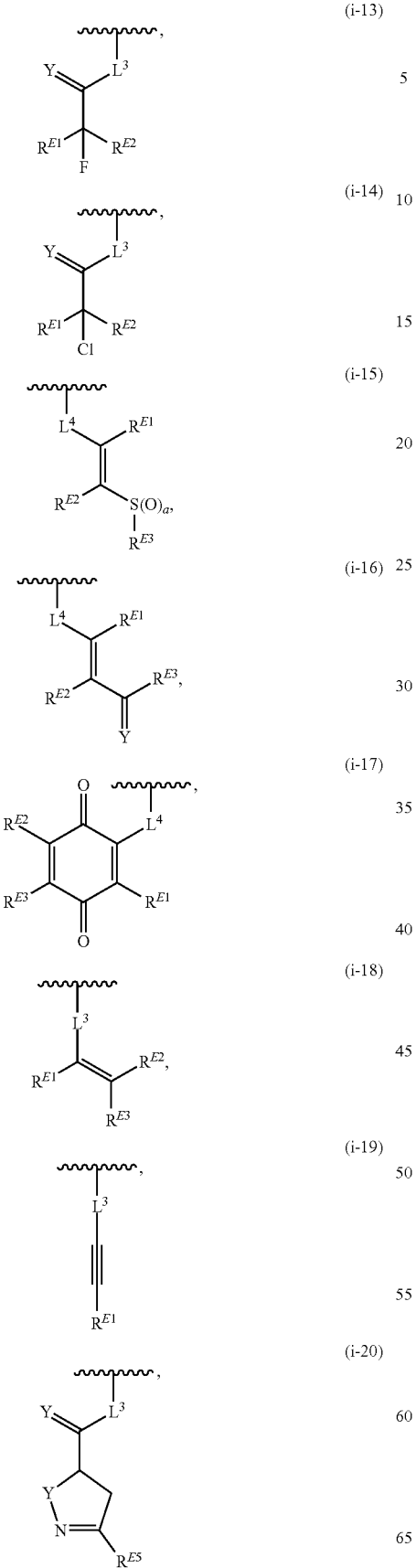
(i-13)
(i-14)
(i-15)
(i-16)
(i-17)
(i-18)
(i-19)
(i-20)
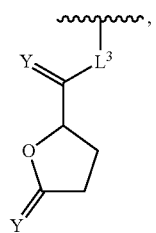
(i-21)
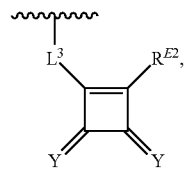
(i-22)
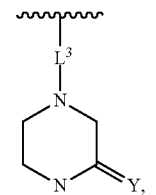
(i-23)
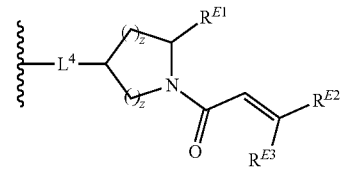
(i-24)
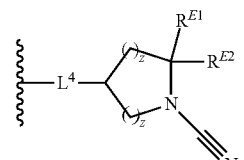
(i-25)
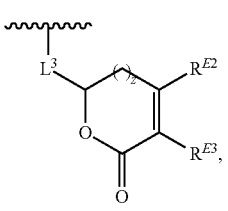
(i-26)
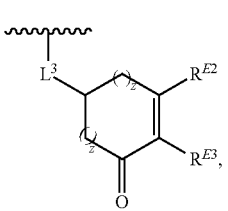
(i-27)

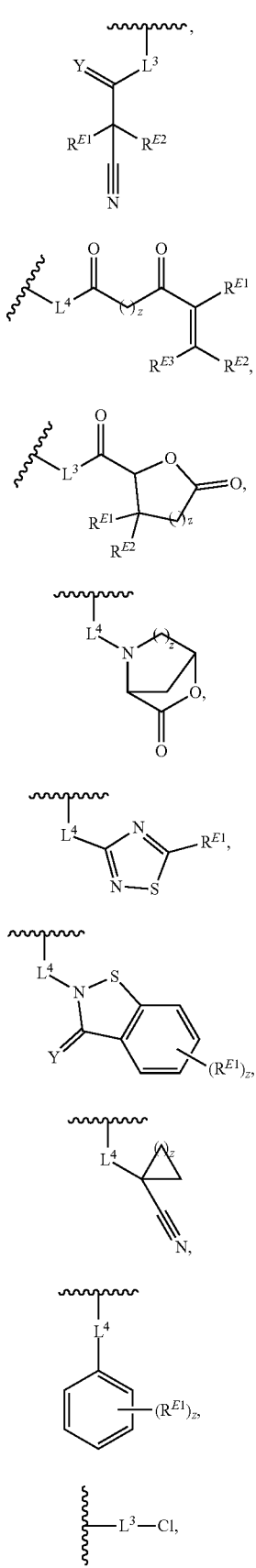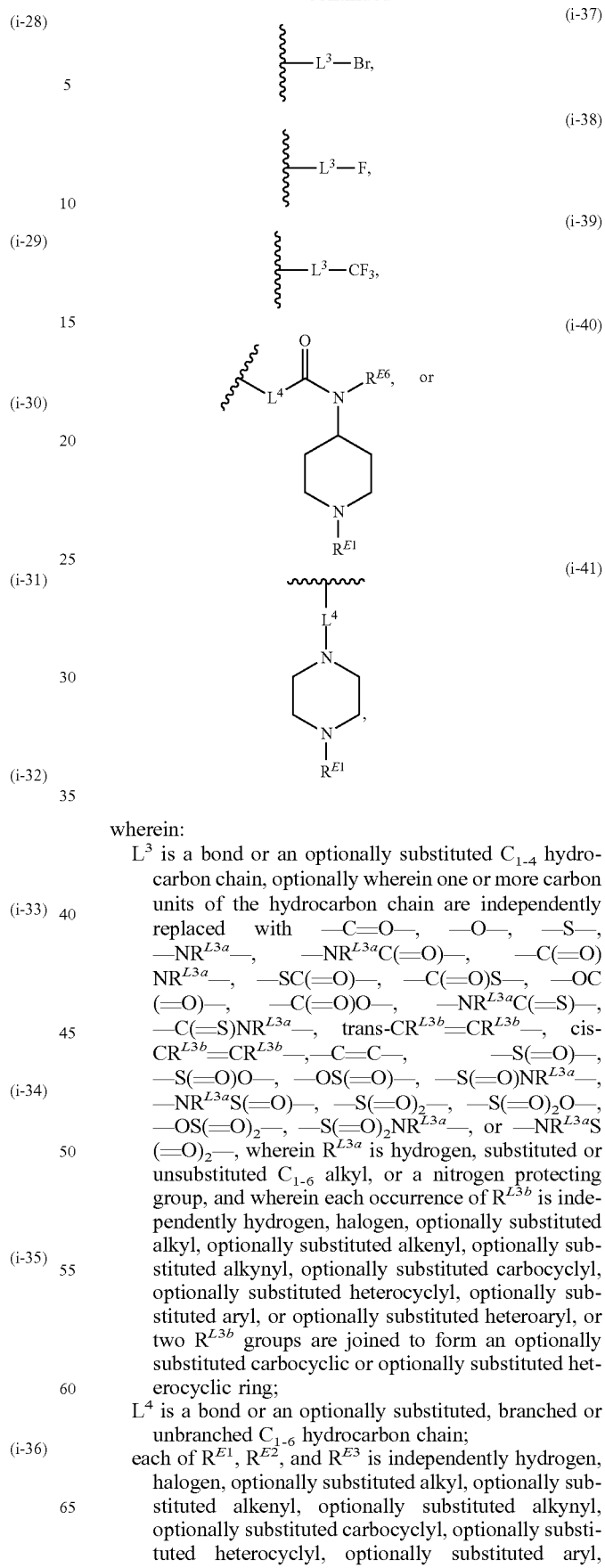

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR^EE, —CH₂N(R^EE)₂, —CH₂SR^EE, —OR^EE, —N(R^EE)₂, —Si(R^EE)₃, or —SR^EE, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two $R^{EE}$ groups are joined to form an optionally substituted heterocyclic ring; or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

$R^{E6}$ is hydrogen, substituted or unsubstituted $C_{1-6}$ alkyl, or a nitrogen protecting group;

each instance of Y is independently O, S, or $NR^{E7}$, wherein $R^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits; and W is —CR^{D1}— or —N=;

each instance of $R^8$, if present, is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR^{D1}, —N(R^{D1a})₂, and —SR^{D1}, wherein each occurrence of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom, wherein each occurrence of $R^{D1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of $R^{D1a}$ are taken together with their intervening atoms to form a substituted or unsubstituted heterocyclic or substituted or unsubstituted heteroaryl ring; or two $R^8$ groups are joined to form an optionally substituted carbocyclyl, optionally substituted heterocyclyl, optionally substituted aryl, or optionally substituted heteroaryl ring;

m is 0, 1, 2, 3 or 4; and n is 0, 1, 2, 3, 4, 5 or 6.

In certain embodiments, a compound of Formula (I') is of of Formula (I).

In one aspect of the present invention, provided are compounds of Formula (I):

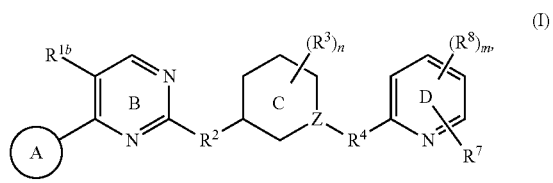

(I)

or a pharmaceutically acceptable salt, solvate, hydrate, polymorph, co-crystal, tautomer, stereoisomer, isotopically labeled derivative, or prodrug thereof, wherein:

Ring A is an optionally substituted heteroaryl ring of any one of the Formulae (ii-1)-(ii-5):

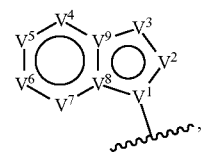

(ii-1)

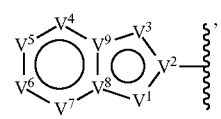

(ii-2)

(ii-3)

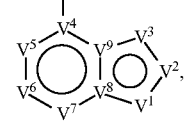

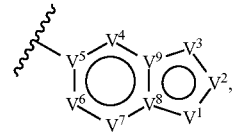

(ii-4)

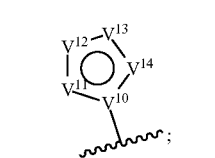

(ii-5)

or an optionally substituted 6-membered aryl or heteroaryl ring;

each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, and $V^{14}$ is independently O, S, N, $N(R^{41})$, C, or $C(R^{42})$;

Z is —CH— or —N—;

each instance of $R^{41}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each instance of $R^{42}$ is independently selected from hydrogen, halogen, —CN, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR^{A2a}, —N(R^{A2b})₂, and —SR^{A2a}, wherein $R^{A2a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom;

wherein each occurrence of $R^{A2b}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of $R^{A2b}$ are taken together with their intervening atoms to form a substituted or unsubstituted heterocyclic or substituted or unsubstituted heteroaryl ring; or any two $R^{A1}$, any two $R^{A2}$, or one $R^{A1}$ and one $R^{A2}$ are joined to form an optionally substituted carbocyclic, optionally substituted heterocyclic, optionally substituted aryl, or optionally substituted heteroaryl ring;

each of $R^{1b}$ is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{B1a}$, —$N(R^{B1b})_2$, and —$SR^{B1a}$, wherein each occurrence of $R^{B1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom;

wherein each occurrence of $R^{B1b}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of $R^{B1b}$ are taken together with their intervening atoms to form a substituted or unsubstituted heterocyclic or substituted or unsubstituted heteroaryl ring;

$R^2$ is —O—, —S—, —$N(R^6)$—, or an optionally substituted $C_1$-$C_4$ alkylene, wherein one or more methylene units of the alkylene are optionally and independently replaced with —O—, —S—, or —$N(R^6)$—;

each instance of $R^3$, if present, is independently selected from halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{C1}$, —$N(R^{C1a})_2$, and —$SR^{C1}$, wherein each occurrence of $R^{C1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom;

wherein each occurrence of $R^{C1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of $R^{C1a}$ are taken together with their intervening atoms to form a substituted or unsubstituted heterocyclic or substituted or unsubstituted heteroaryl ring; or two $R^3$ groups bound to the same ring carbon atom are taken together to form =O, or two $R^3$ groups bound to the same or different ring carbon atoms are joined to form an optionally substituted carbocyclyl, optionally substituted heterocyclyl, optionally substituted aryl, or optionally substituted heteroaryl ring;

$R^4$ is selected from a bond, —C(=O)—, —O—, —S—, —$N(R^6)$—, —$S(=O)_2$—, or an optionally substituted $C_1$-$C_4$ alkylene, wherein:

one or more methylene units of the alkylene other than a methylene unit bound to a nitrogen atom is optionally and independently replaced with —C(=O), —O—, —S—, —$N(R^6)$—, or —$S(=O)_2$—;

each $R^6$ is independently selected from hydrogen and —$C_1$-$C_6$ alkyl;

$R^7$ is a warhead of formula:

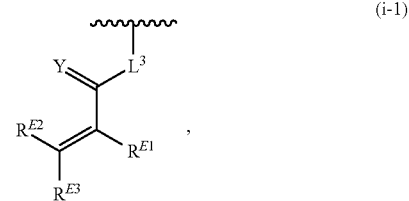

(i-1)

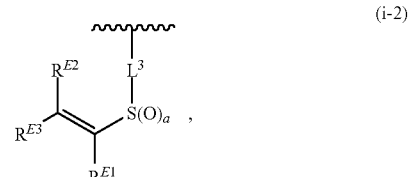

(i-2)

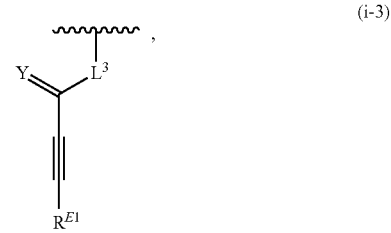

(i-3)

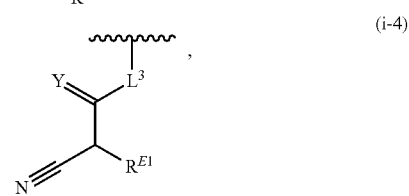

(i-4)

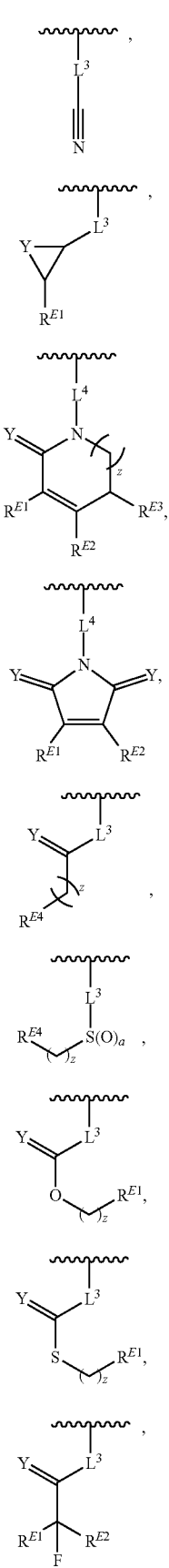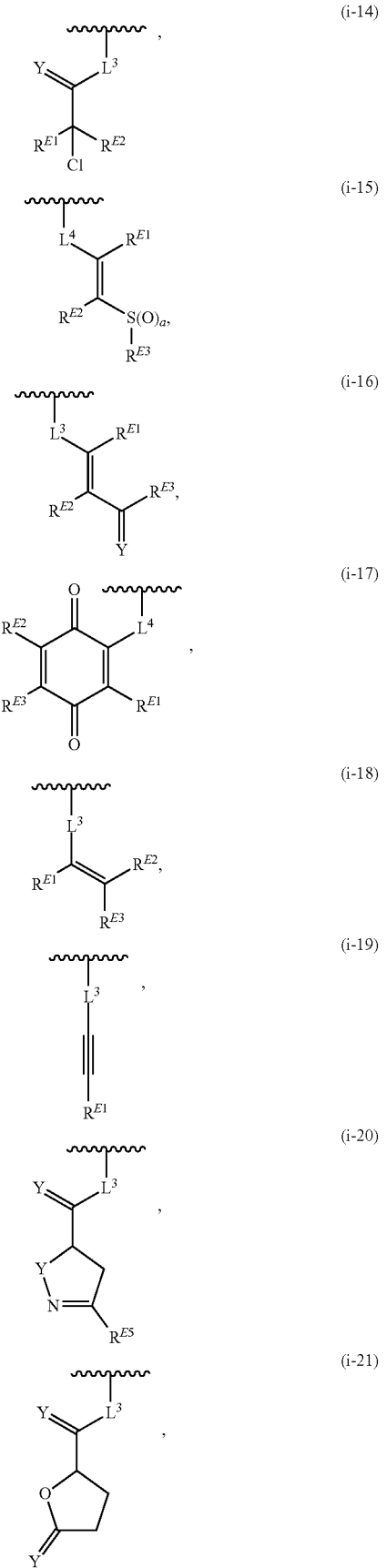

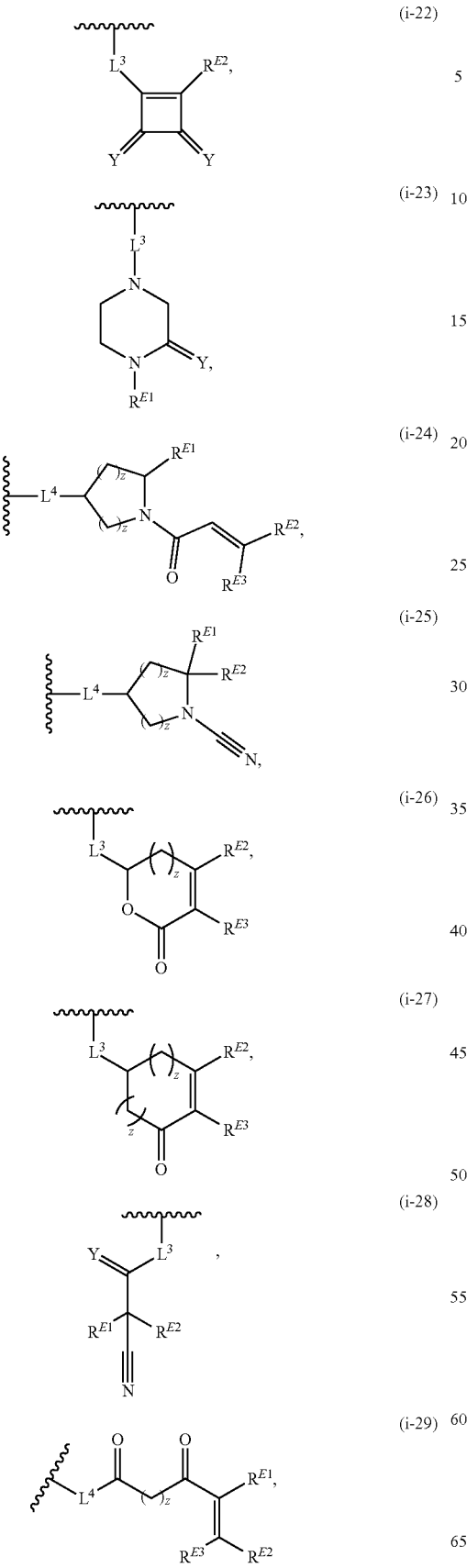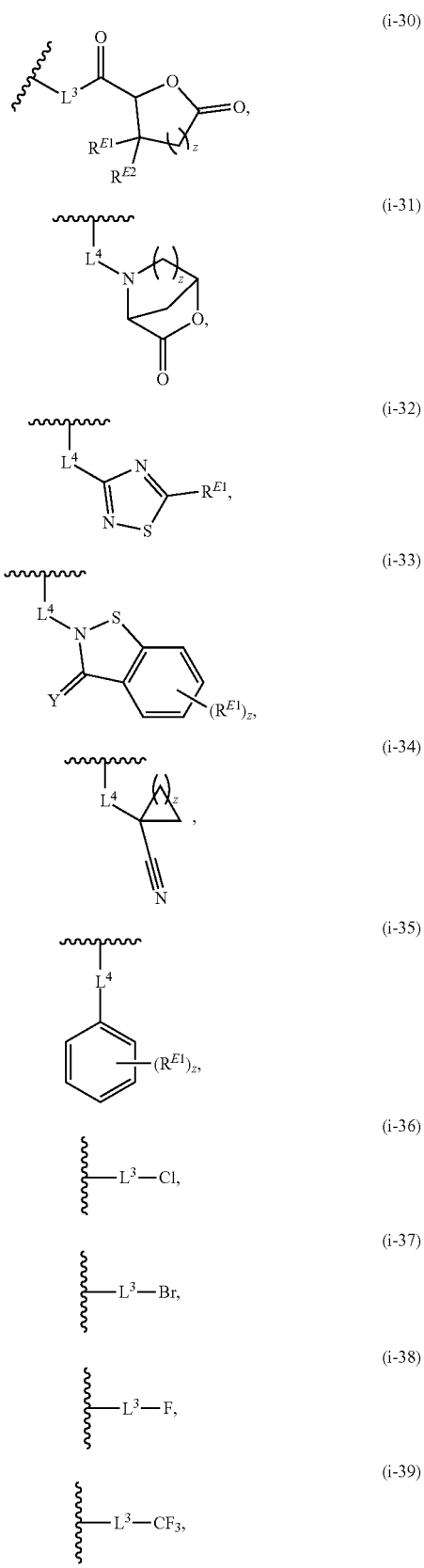

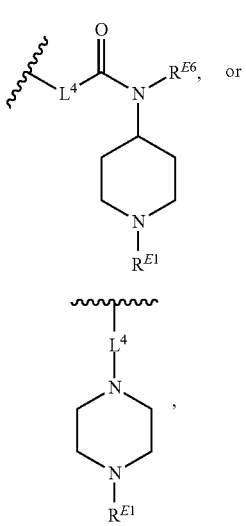

(i-40)

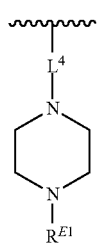

(i-41)

wherein:

L³ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L⁴ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits; and each instance of R⁸, if present, is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$, wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of R$^{D1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of R$^{D1a}$ are taken together with their intervening atoms to form a substituted or unsubstituted heterocyclic or substituted or unsubstituted heteroaryl ring; or two R⁸ groups are joined to form an optionally substituted carbocyclyl, optionally substituted heterocyclyl, optionally substituted aryl, or optionally substituted heteroaryl ring;

m is 0, 1, 2, 3 or 4; and n is 0, 1, 2, 3, 4, 5 or 6.

In certain embodiments, a compound described herein is of Formula (II):

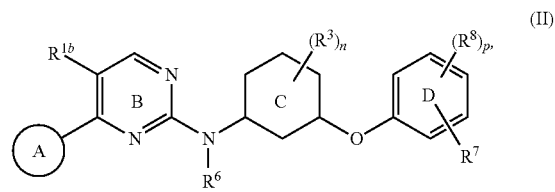

(II)

or a pharmaceutically acceptable salt, solvate, hydrate, polymorph, co-crystal, tautomer, stereoisomer, isotopically labeled derivative, or prodrug thereof, wherein:

Ring A is an optionally substituted heteroaryl ring of any one of the Formulae (ii-1)-(ii-5):

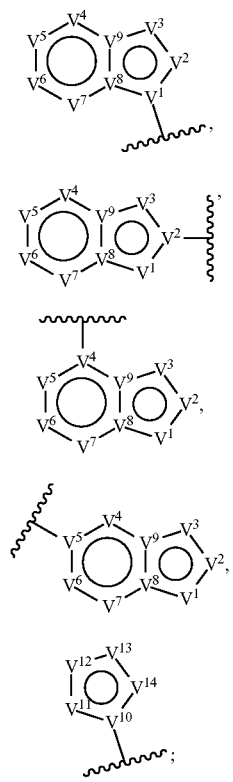

(ii-1)

(ii-2)

(ii-3)

(ii-4)

(ii-5)

or an optionally substituted 6-membered aryl or heteroaryl ring;

each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, and $V^{14}$ is independently O, S, N, $N(R^{A1})$, C, or $C(R^{A2})$;

each instance of $R^{A1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each instance of $R^{A2}$ is independently selected from hydrogen, halogen, —CN, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A2a}$, —$N(R^{A2b})_2$, and —$SR^{A2a}$, wherein $R^{A2a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom;

wherein each occurrence of $R^{A2b}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of $R^{A2b}$ are taken together with their intervening atoms to form a substituted or unsubstituted heterocyclic or substituted or unsubstituted heteroaryl ring; or any two $R^{A1}$, any two $R^{A2}$, or one $R^{A1}$ and one $R^{A2}$ are joined to form an optionally substituted carbocyclic, optionally substituted heterocyclic, optionally substituted aryl, or optionally substituted heteroaryl ring;

each of $R^{1b}$ is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{B1a}$, —$N(R^{B1b})_2$, and —$SR^{B1a}$, wherein each occurrence of $R^{B1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom;

wherein each occurrence of $R^{B1b}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of $R^{B1b}$ are taken together with their intervening atoms to form a substituted or unsubstituted heterocyclic or substituted or unsubstituted heteroaryl ring;

each instance of $R^3$, if present, is independently selected from halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{C1}$, —$N(R^{C1a})_2$, and —$SR^{C1}$, wherein each occurrence of $R^{C1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom;

wherein each occurrence of $R^{C1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of $R^{C1a}$ are taken together with their intervening atoms to form a substituted or unsubstituted heterocyclic or substituted or unsubstituted heteroaryl ring; or two $R^3$ groups bound to the same ring carbon atom are taken together to form =O, or two $R^3$ groups bound to the same or different ring carbon atoms are joined to form an optionally substituted carbocyclyl, optionally substituted heterocyclyl, optionally substituted aryl, or optionally substituted heteroaryl ring;
each $R^6$ is independently selected from hydrogen and —$C_1$-$C_6$ alkyl;
$R^7$ is a warhead of formula:
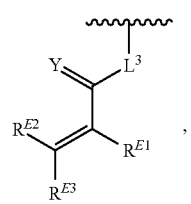
(i-1)
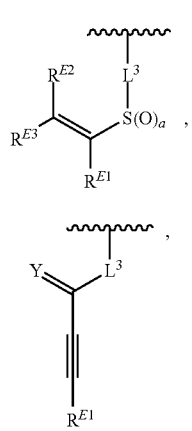
(i-2)
(i-3)
(i-4)
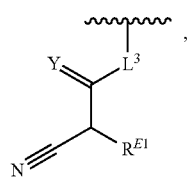
(i-5)
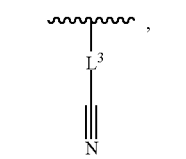
(i-6)
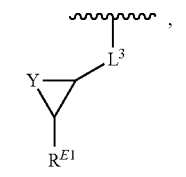
(i-7)
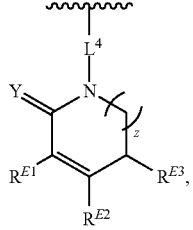
-continued
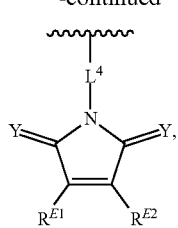
(i-8)
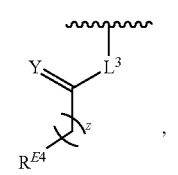
(i-9)
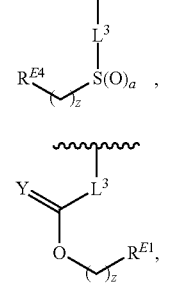
(i-10)
(i-11)
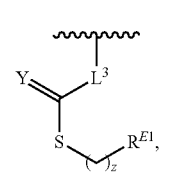
(i-12)
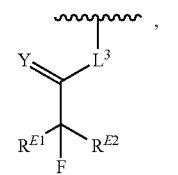
(i-13)
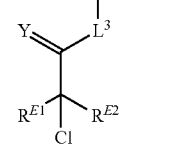
(i-14)
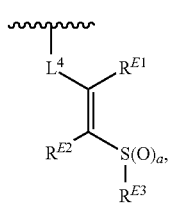
(i-15)
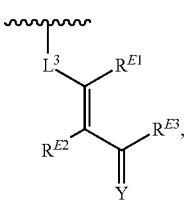
(i-16)

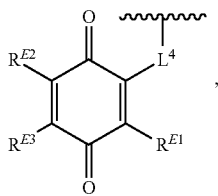 (i-17)
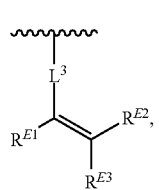 (i-18)
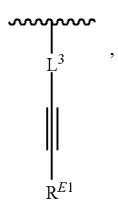 (i-19)
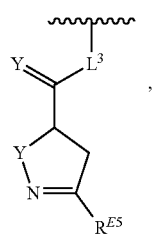 (i-20)
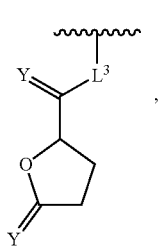 (i-21)
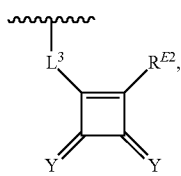 (i-22)
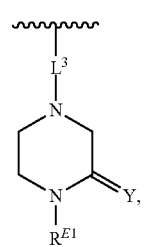 (i-23)
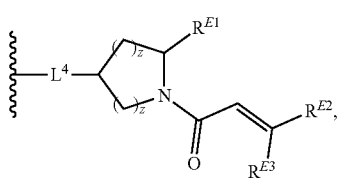 (i-24)
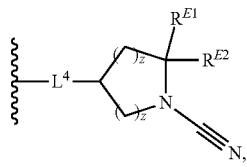 (i-25)
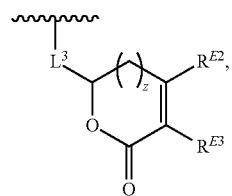 (i-26)
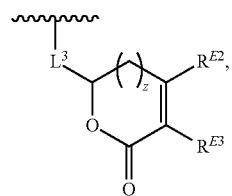 (i-27)
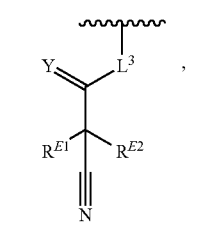 (i-28)
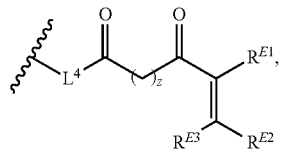 (i-29)
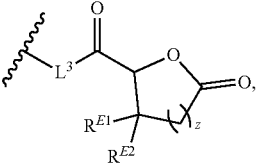 (i-30)
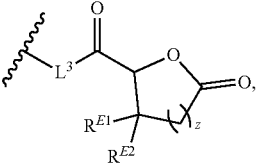 (i-31)

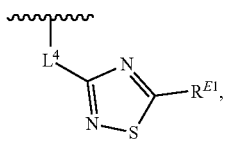 (i-32)

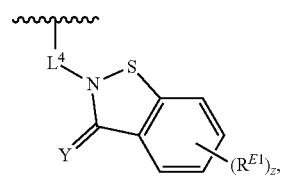 (i-33)

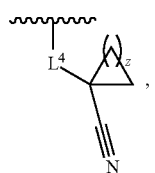 (i-34)

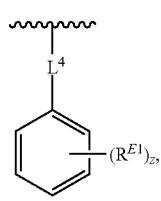 (i-35)

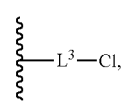 (i-36)

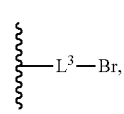 (i-37)

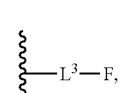 (i-38)

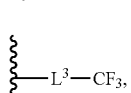 (i-39)

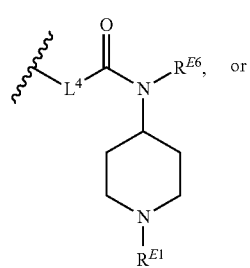 (i-40)

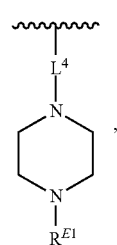 (i-41)

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits; and each instance of R$^8$, if present, is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$, wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom;

wherein each occurrence of R$^{D1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of R$^{D1a}$ are taken together with their intervening atoms to form a substituted or unsubstituted heterocyclic or substituted or unsubstituted heteroaryl ring; or two R$^8$ groups are joined to form an optionally substituted carbocyclyl, optionally substituted heterocyclyl, optionally substituted aryl, or optionally substituted heteroaryl ring;

n is 0, 1, 2, 3, 4, 5 or 6; and p is 0, 1, 2, 3, 4, or 5.

As generally defined herein in Formulae (I') and (II), Ring A is an optionally substituted heteroaryl ring of any one of the Formulae (ii-1)-(ii-5):

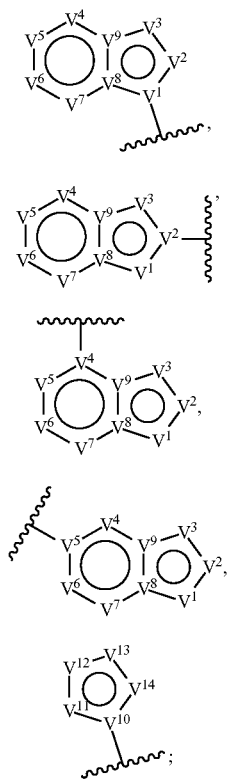

or an optionally substituted 6-membered aryl or heteroaryl ring; wherein each instance of V$^1$, V$^2$, V$^3$, V$^4$, V$^5$, V$^6$, V$^7$, V$^8$, V$^9$, V$^{10}$, V$^{11}$, V$^{12}$, V$^{13}$, and V$^{14}$ is independently O, S, N, N(R$^{A1}$) C, or C(R$^{A2}$).

Compounds of Formulae (I') and (II) include Ring A. In certain embodiments, Ring A is an optionally substituted monocyclic heteroaryl ring fused with an optionally substituted monocyclic aryl ring. In certain embodiments, Ring A is an optionally substituted 6-membered aryl ring. In certain embodiments, Ring A is an optionally substituted 6-membered heteroaryl ring. In certain embodiments, Ring A is an optionally substituted bicyclic heteroaryl ring. In certain embodiments, Ring A is an optionally substituted monocyclic heteroaryl ring fused with another optionally substituted monocyclic heteroaryl ring. Ring A may be an optionally substituted 6,5-membered heteroaryl ring or an optionally substituted 5,6-membered heteroaryl ring. In certain embodiments, Ring A is an optionally substituted monocyclic 5-membered heteroaryl ring fused with an optionally substituted monocyclic 6-membered aryl ring. In certain embodiments, Ring A is an optionally substituted monocyclic 5-membered heteroaryl ring fused with an optionally substituted monocyclic 6-membered heteroaryl ring. The point of attachment of Ring A to Ring B may be at any atom of Ring A, as valency permits. In certain embodiments, Ring A is of Formula (ii-1):

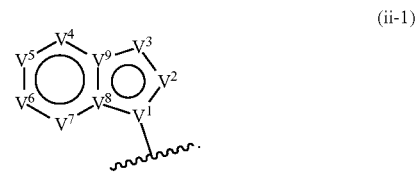

In certain embodiments, Ring A is of Formula (ii-2):

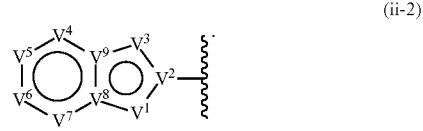

In certain embodiments, Ring A is of Formula (ii-3):

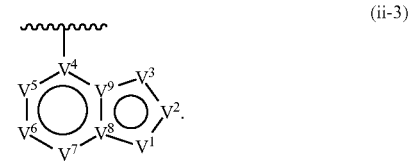

In certain embodiments, Ring A is of Formula (ii-4):

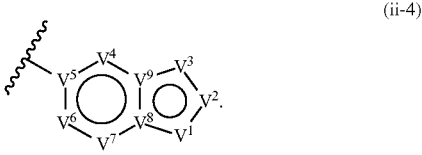

As generally described herein, in Formulae (I') and (II), $V^1$, $V^2$, $V^3$, $V^4$, $V^5$, $V^6$, $V^7$, $V^8$, and $V^9$ of Ring A may each independently be O, S, N, $NR^{A1}$, C, or $CR^{A2}$, as valency permits. In certain embodiments, $V^1$ is O, S, N or $NR^{A1}$. In certain embodiments, $V^1$ is N or $NR^A$. In certain embodiments, Ring A is of formula:

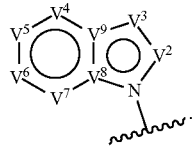

In certain embodiments, Ring A is of formula:

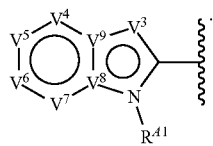

In certain embodiments, Ring A is of formula:

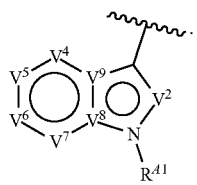

In certain embodiments, Ring A is of formula:

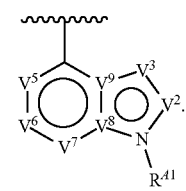

In certain embodiments, Ring A is of formula:

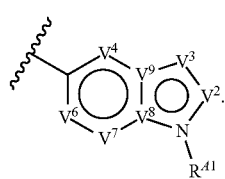

In certain embodiments, Ring A is of formula:

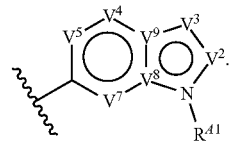

In certain embodiments, Ring A is of formula:

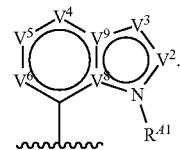

In certain embodiments, only one of $V^1$, $V^2$, $V^3$, $V^4$, $V^5$, $V^6$, $V^7$, $V^8$, and $V^9$ is selected from the group consisting of O, S, N, and $NR^{A1}$. In certain embodiments, only one of $V^1$, $V^2$, $V^3$, $V^4$, $V^5$, $V^6$, $V^7$, $V^8$, and $V^9$ is selected from the group consisting of N and $NR^{A1}$. In certain embodiments, $V^1$ is N or $NR^{A1}$; $V^2$, $V^3$, $V^4$, $V^5$, $V^6$, $V^7$, $V^8$, and $V^9$ are each independently C or $CR^{A2}$; and therefore, Ring A is an optionally substituted indole ring. In certain embodiments, Ring A is of Formula (iii-1):

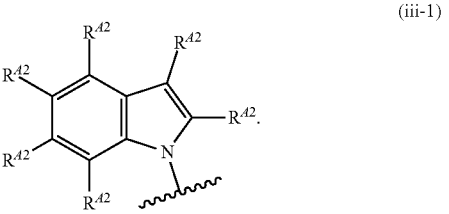

(iii-1)

In certain embodiments, Ring A is of Formula (iii-2):

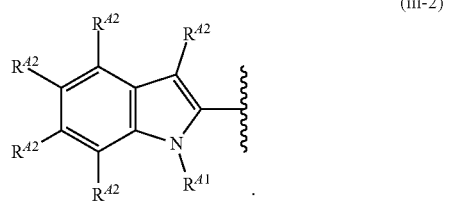

(iii-2)

In certain embodiments, Ring A is of Formula (iii-3):

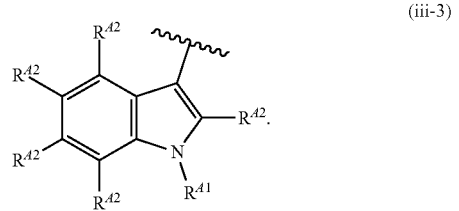

(iii-3)

In certain embodiments, Ring A is of formula:

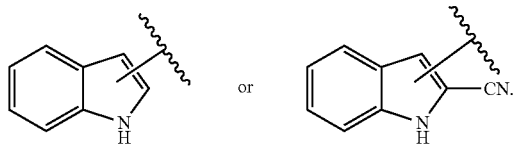

In certain embodiments, Ring A is of formula:

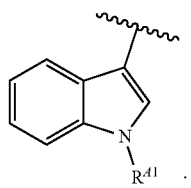

In certain embodiments, Ring A is of formula:

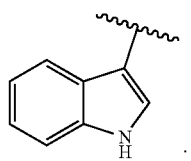 [SMILES: *c1c[nH]c2ccccc12]

In certain embodiments, Ring A is of formula:

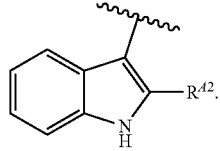

In certain embodiments, Ring A is of formula:

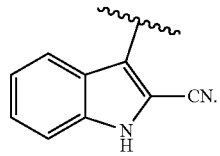 [SMILES: *c1c(C#N)[nH]c2ccccc12]

In certain embodiments, Ring A is of Formula (iii-4):

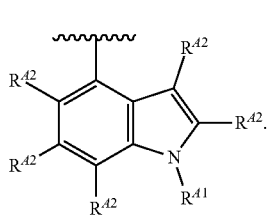

(iii-4)

In certain embodiments, Ring A is of Formula (iii-5):

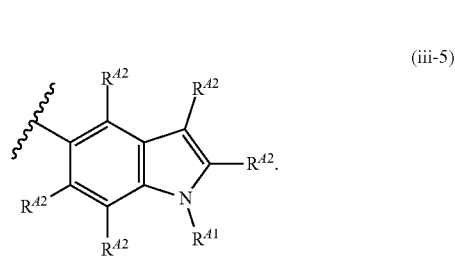

(iii-5)

In certain embodiments, Ring A is of Formula (iii-6):

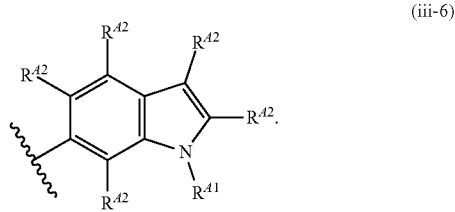

(iii-6)

In certain embodiments, Ring A is of Formula (iii-7):

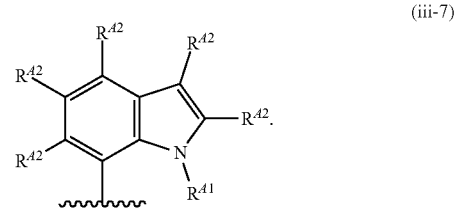

(iii-7)

In certain embodiments, only two of $V^1$, $V^2$, $V^3$, $V^4$, $V^5$, $V^6$, $V^7$, $V^8$, and $V^9$ are each independently selected from the group consisting of O, S, N, and $NR^{A1}$. In certain embodiments, only two of $V^1$, $V^2$, $V^3$, $V^4$, $V^5$, $V^6$, $V^7$, $V^8$, and $V^9$ are each independently selected from the group consisting of N and $NR^{A1}$. In certain embodiments, $V^1$ is N or $NR^{A1}$; and only one of $V^2$, $V^3$, $V^4$, $V^5$, $V^6$, $V^7$, $V^8$, and $V^9$ is N or $NR^{A1}$. In certain embodiments, $V^1$ and $V^2$ are each independently N or $NR^{A1}$; $V^3$, $V^4$, $V^5$, $V^6$, $V^7$, $V^8$, and $V^9$ are each independently C or $CR^{A2}$; and therefore, Ring A is an optionally substituted indazole ring. In certain embodiments, Ring A is of formula:

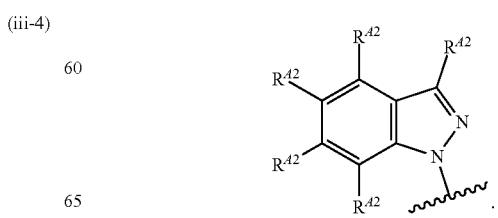

In certain embodiments, Ring A is of formula:

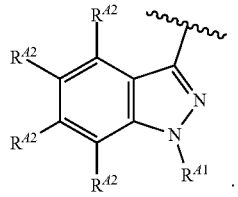

In certain embodiments, Ring A is of formula:

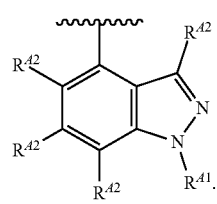

In certain embodiments, Ring A is of formula:

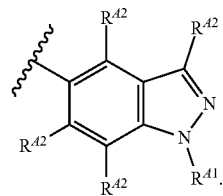

In certain embodiments, Ring A is of formula:

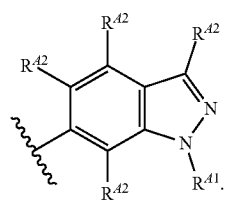

In certain embodiments, Ring A is of formula:

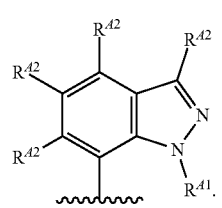

In certain embodiments, $V^1$ and $V^3$ are each independently N or $NR^{A1}$; $V^2$, $V^4$, $V^5$, $V^6$, $V^7$, $V^8$, and $V^9$ are each independently C or $CR^{A2}$; and therefore, Ring A is an optionally substituted benzimidazole ring. In certain embodiments, Ring A is of Formula (iv-1):

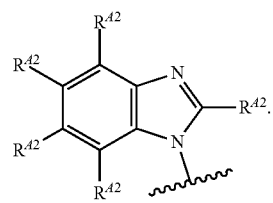

(iv-1)

In certain embodiments, Ring A is of Formula (iv-2):

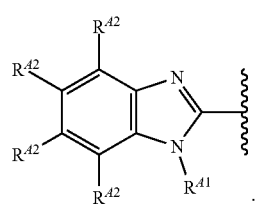

(iv-2)

In certain embodiments, Ring A is of Formula (iv-3):

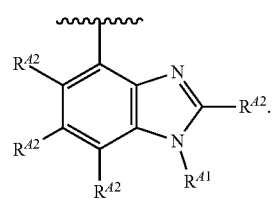

(iv-3)

In certain embodiments, Ring A is of Formula (iv-4):

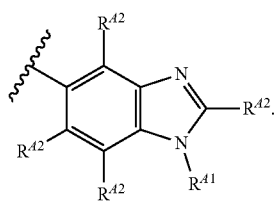

(iv-4)

In certain embodiments, Ring A is of Formula (iv-5):

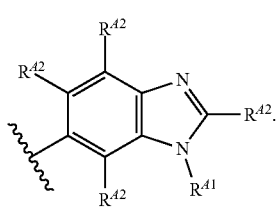

(iv-5)

In certain embodiments, Ring A is of Formula (iv-6):

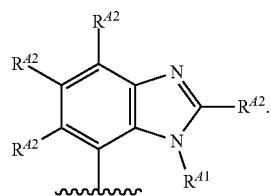

In certain embodiments, $V^1$ and $V^4$ are each independently N or $NR^{A1}$; $V^2$, $V^3$, $V^5$, $V^6$, $V^7$, $V^8$, and $V^9$ are each independently C or $CR^{A2}$; and therefore, Ring A is an optionally substituted 4-azaindazole ring. In certain embodiments, Ring A is of formula:

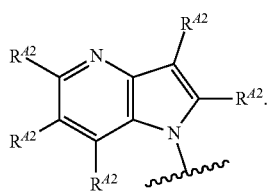

In certain embodiments, Ring A is of formula:

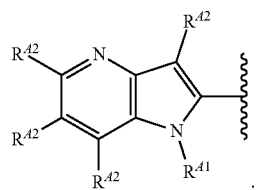

In certain embodiments, Ring A is of formula:

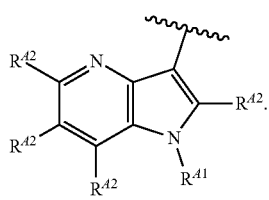

In certain embodiments, Ring A is of formula:

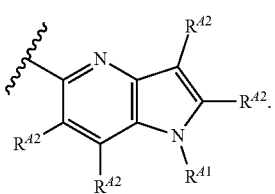

In certain embodiments, Ring A is of formula:

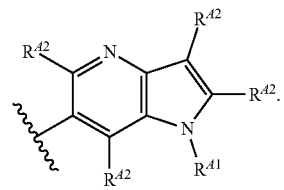

In certain embodiments, Ring A is of formula:

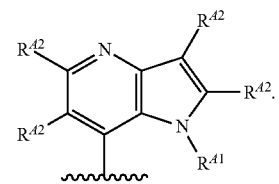

In certain embodiments, $V^1$ and $V^5$ are each independently N or $NR^{A1}$; $V^2$, $V^3$, $V^4$, $V^6$, $V^7$, $V^8$, and $V^9$ are each independently C or $CR^{A2}$; and therefore, Ring A is an optionally substituted 5-azaindazole ring. In certain embodiments, Ring A is of formula:

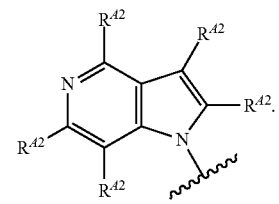

In certain embodiments, Ring A is of formula:

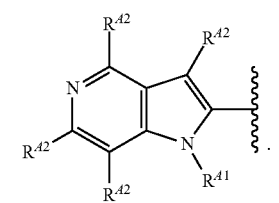

In certain embodiments, Ring A is of formula

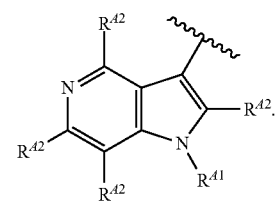

In certain embodiments, Ring A is of formula:

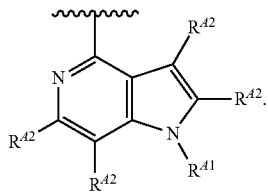

In Certain embodiments, Ring A is of formula:

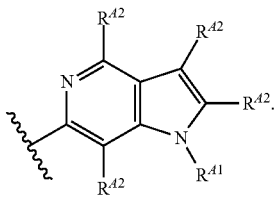

In certain embodiments, Ring A is of formula:

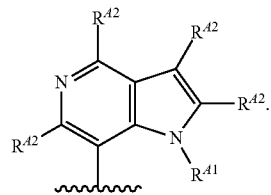

In certain embodiments, $V^1$ and $V^6$ are each independently N or $NR^{A1}$; $V^2$, $V^3$, $V^4$, $V^5$, $V^7$, $V^8$, and $V^9$ are each independently C or $CR^{A2}$; and therefore, Ring A is an optionally substituted 6-azaindole ring. In certain embodiments, Ring A is of formula:

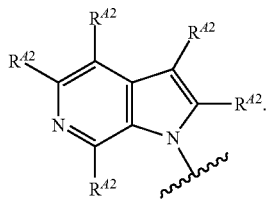

In certain embodiments, Ring A is of formula:

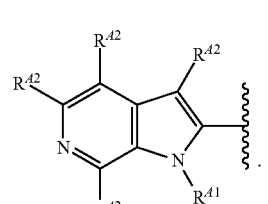

In certain embodiments, Ring A is of formula:

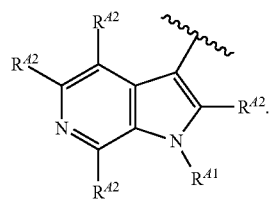

In certain embodiments, Ring A is of formula:

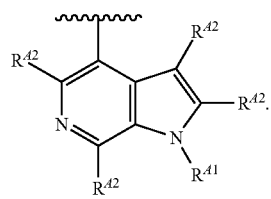

In certain embodiments, Ring A is of formula:

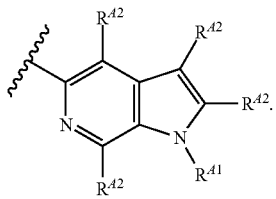

In certain embodiments, Ring A is of formula:

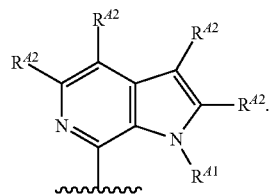

In certain embodiments, $V^1$ and $V^7$ are each independently N or $NR^{A1}$ $V^2$, $V^3$, $V^4$, $V^1$, $V^6$, $V^8$, and $V^9$ are each independently C or $CR^{A2}$; and therefore, Ring A is an optionally substituted 7-azaindole ring. In certain embodiments, Ring A is of Formula (v-1):

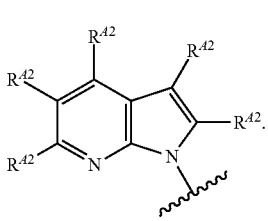

(v-1)

In certain embodiments, Ring A is of Formula (v-2):

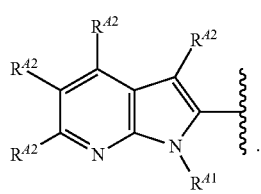

(v-2)

In certain embodiments, Ring A is of Formula (v-3):

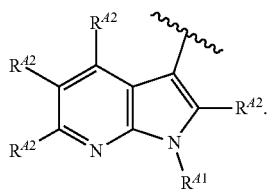

(v-3)

In certain embodiments, Ring A is of Formula (v-4):

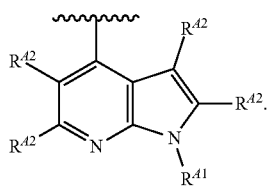

(v-4)

In certain embodiments, Ring A is of Formula (v-5):

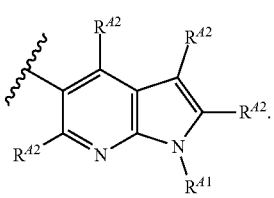

(v-5)

In certain embodiments, Ring A is of Formula (v-6):

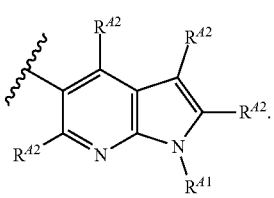

(v-6)

In certain embodiments, $V^1$ and $V^8$ are each independently N or $NR^{A1}$, $V^2$, $V^3$, $V^4$, $V^1$, $V^6$, $V^7$, and $V^9$ are each independently C or $CR^{A2}$; and therefore, Ring A is an optionally substituted 8-azaindole ring. In certain embodiments, Ring A is of Formula (vi-1):

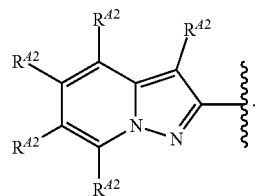

(vi-1)

In certain embodiments, Ring A is of Formula (vi-2):

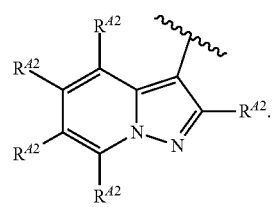

(vi-2)

In certain embodiments, Ring A is of Formula (vi-3):

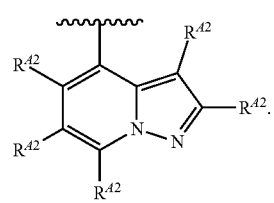

(vi-3)

In certain embodiments, Ring A is of Formula (vi-4):

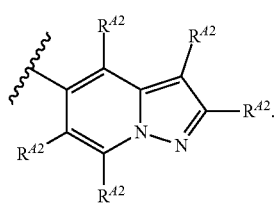

(vi-4)

In certain embodiments, Ring A is of Formula (vi-5):

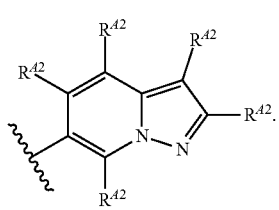

(vi-5)

In certain embodiments, Ring A is of Formula (vi-6):

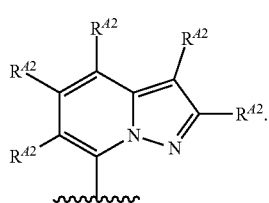
(vi-6)

In certain embodiments, $V^1$ and $V^9$ are each independently N or $NR^{A1}$; $V^2$, $V^3$, $V^4$, $V^1$, $V^6$, $V^7$, and $V^8$ are each independently C or $CR^{A2}$; and therefore, Ring A is an optionally substituted 9-azaindole ring. In certain embodiments, Ring A is of formula:

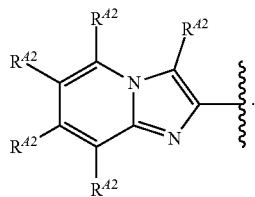

In certain embodiments, Ring A is of formula:

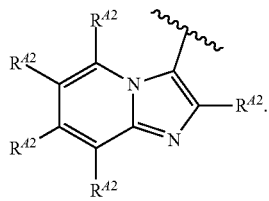

In certain embodiments, Ring A is of formula:

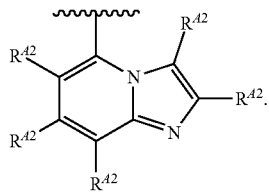

In Certain embodiments, Ring A is of formula:

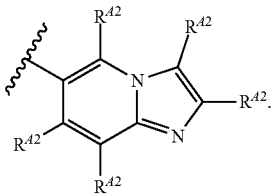

In Certain embodiments, Ring A is of formula:

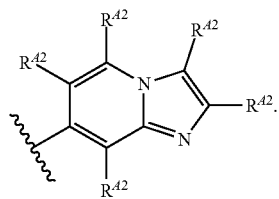

In certain embodiments, Ring A is of formula:

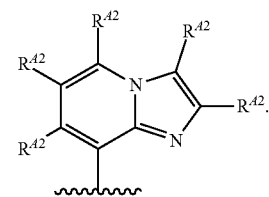

In certain embodiments, only three of $V^1$, $V^2$, $V^3$, $V^4$, $V^5$, $V^6$, $V^7$, $V^8$, and $V^9$ are each independently selected from the group consisting of O, S, N, and $NR^{A1}$. In certain embodiments, only three of $V^1$, $V^2$, $V^3$, $V^4$, $V^5$, $V^6$, $V^7$, $V^8$, and $V^9$ are each independently selected from the group consisting of N and $NR^{A1}$. In certain embodiments, $V^1$ is N or $NR^{A1}$; and only two of $V^2$, $V^3$, $V^4$, $V^5$, $V^6$, $V^7$, $V^8$, and $V^9$ are each independently N or $NR^{A1}$.

As generally described herein, in Formulae (I') and (II), Ring A may also be an optionally substituted 5-membered heteroaryl ring. In certain embodiments, Ring A is of Formula (ii-5):

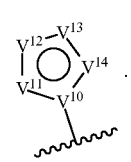
(ii-5)

As generally described herein, in Formulae (I') and (II), $V^{10}$, $V^{11}$, $V^{12}$, $V^{13}$, and $V^{14}$ of Ring A may each independently be O, S, N, $NR^{A1}$, C, or $CR^{A2}$, as valency permits. In certain embodiments, only one of $V^{10}$, $V^{11}$, $V^{12}$, $V^{13}$, and $V^{14}$ is selected from the group consisting of O, S, N, and $NR^{A1}$. In certain embodiments, Ring A is of formula:

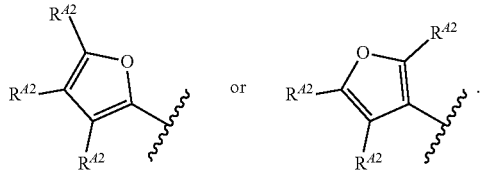

In certain embodiments, Ring A is of formula:

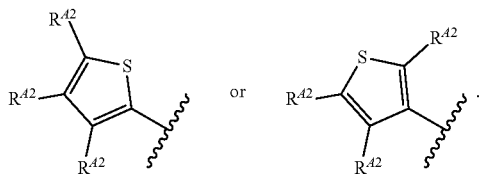 or 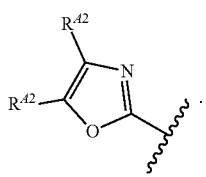

In certain embodiments, Ring A is of formula:

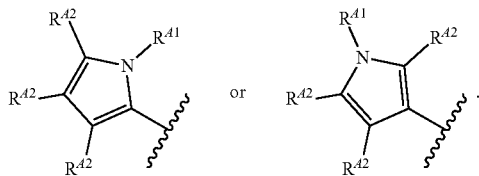

In certain embodiments, only two of $V^{10}$, $V^{11}$, $V^{12}$, $V^{13}$, and $V^{14}$ are independently selected from the group consisting of O, S, N, and $NR^{A1}$. In certain embodiments, Ring A is of formula:

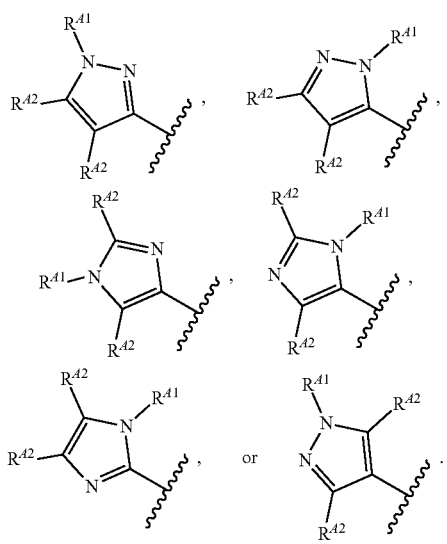

In certain embodiments, Ring A is of formula:

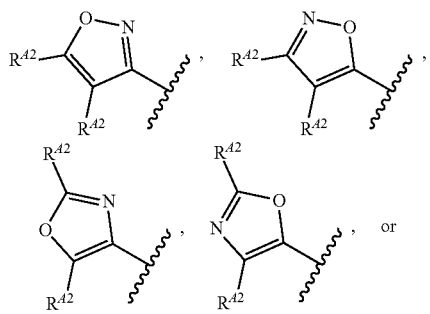

In certain embodiments, Ring A is of formula:

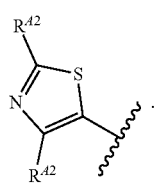

In certain embodiments, Ring A is of Formula (vii):

(vii)

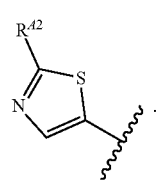

In certain embodiments, Ring A is of formula:

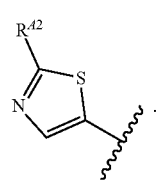

In certain embodiments, Ring A is of formula:

In certain embodiments, Ring A is of formula:

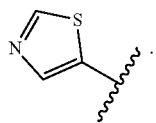

In certain embodiments, only three of $V^{10}$, $V^{11}$, $V^{12}$, $V^{13}$, and $V^{14}$ are each independently selected from the group consisting of O, S, N, and $NR^{41}$. In certain embodiments, Ring A is of formula:

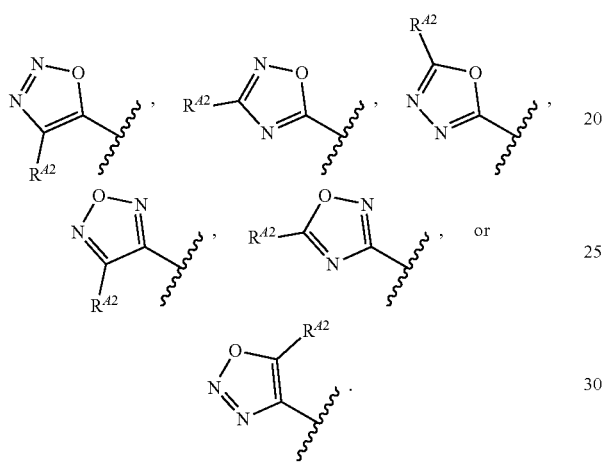

In certain embodiments, Ring A is of formula:

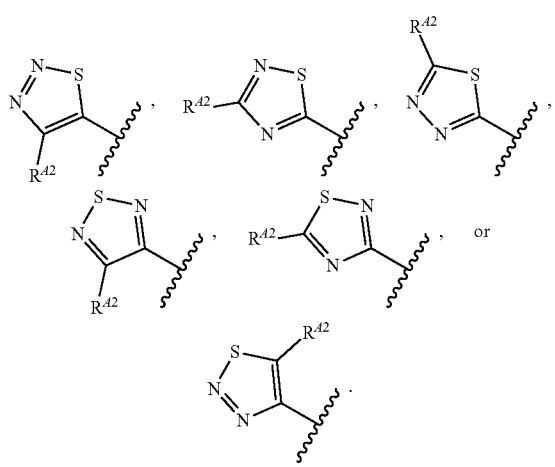

In certain embodiments, Ring A is of formula:

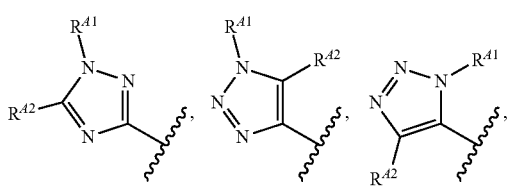

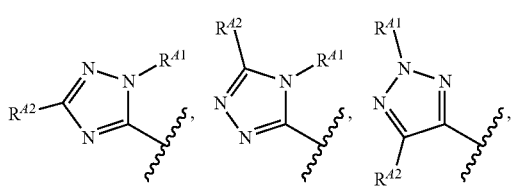

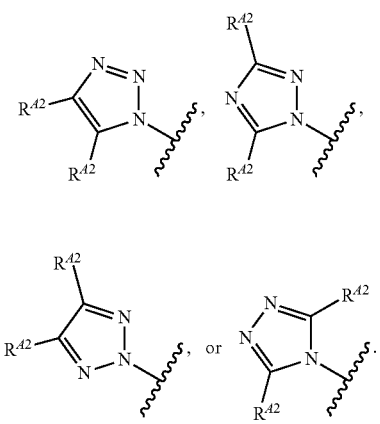

In certain embodiments, only four of $V^{10}$, $V^{11}$, $V^{12}$, $V^{13}$ and $V^{14}$ are each independently selected from the group consisting of N and $NR^{41}$. In certain embodiments, Ring A is of formula:

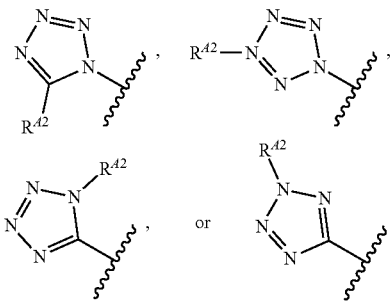

In certain embodiments, Ring A is an optionally substituted 6-membered aryl ring. In certain embodiments, Ring A is optionally substituted phenyl. In certain embodiments, Ring A is an optionally substituted 6-membered heteroaryl ring. In certain embodiments, Ring A is of Formula (ii-6):

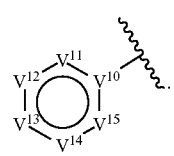

(ii-6)

In certain embodiments, $V^{10}$, $V^{11}$, $V^{12}$, $V^{13}$, $V^{14}$, and $V^{15}$ of Ring A may each independently be N, C, or $CR^{A2}$, as valency permits. In certain embodiments, only one of $V^{10}$, $V^{11}$, $V^{12}$, $V^{13}$, $V^{14}$, and $V^{15}$ is N. In certain embodiments, Ring A is of formula:

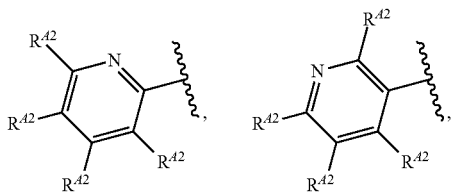

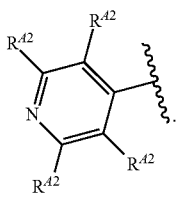

In certain embodiments, only two of $V^{10}$, $V^{11}$, $V^{12}$, $V^{13}$, $V^{14}$, and $V^{15}$ are N. In certain embodiments, Ring A is of formula:

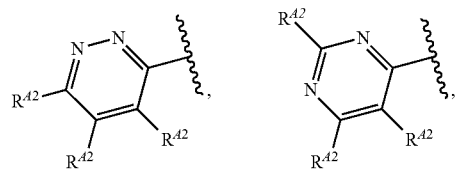

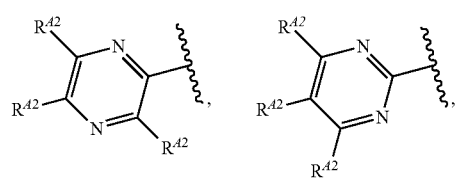

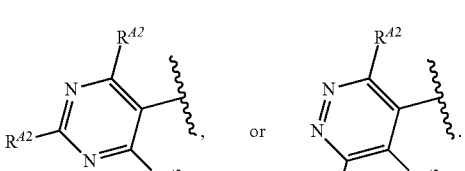

In certain embodiments, only three of $V^{10}$, $V^{11}$, $V^{12}$, $V^{13}$, $V^{14}$, and $V^{15}$ are N. In certain embodiments, Ring A is of formula:

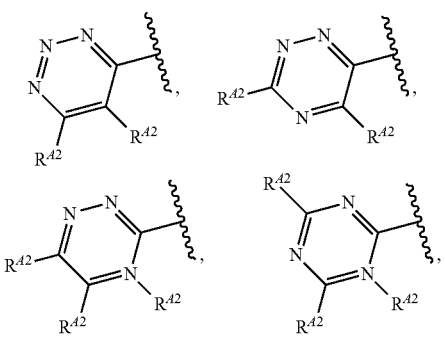

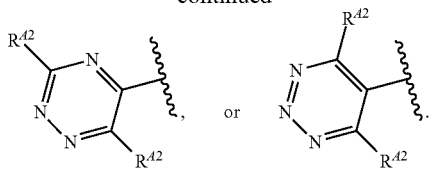

In certain embodiments, Ring A is of Formula (ii-1), (ii-5), or (ii-6). In certain embodiments, Ring A is of formula:

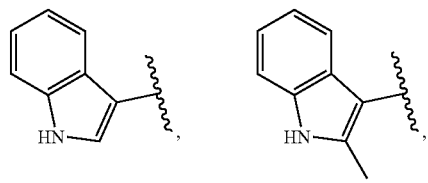

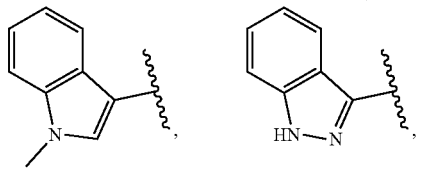

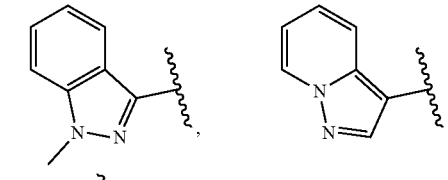

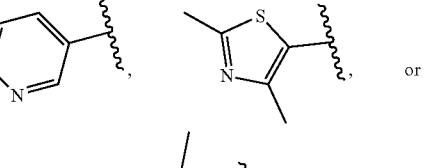

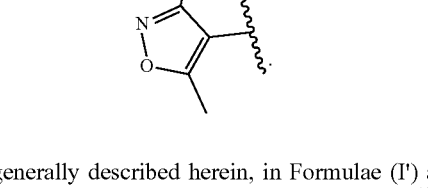

As generally described herein, in Formulae (I') and (II), Ring A may be substituted with one or more $R^{A1}$ groups when the $R^{A1}$ group is attached to a nitrogen atom. In certain embodiments, at least one instance of $R^{A1}$ is H (hydrogen). In certain embodiments, at least one instance of $R^{A1}$ is halogen. In certain embodiments, at least one instance of $R^{A1}$ is F (fluorine). In certain embodiments, at least one instance of $R^{A1}$ is Cl (chlorine). In certain embodiments, at least one instance of $R^{A1}$ is Br (bromine). In certain embodiments, at least one instance of $R^{A1}$ is I (iodine). In certain embodiments, at least one instance of $R^{A1}$ is substituted acyl. In certain embodiments, at least one instance of $R^{A1}$ is unsubstituted acyl. In certain embodiments, at least one instance of $R^{A1}$ is acetyl. In certain embodiments, at least one instance of $R^{A1}$ is substituted acetyl. In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is $C_{1-6}$ alkyl. In certain embodiments, at least one instance of $R^{A1}$ is methyl. In certain embodiments, at least one instance of $R^{A1}$ is ethyl. In certain embodiments, at least one instance of $R^{A1}$ is propyl. In certain embodiments, at least one instance of $R^{A1}$ is butyl. In certain embodiments, at least one instance of $R^{A1}$ is substituted alkenyl. In certain embodiments, at least one instance of $R^{A1}$ is unsubstituted alkenyl. In certain embodiments, at least one instance of $R^{A1}$ is vinyl. In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is ethynyl. In certain embodiments, at least one instance of $R^{A1}$ is substituted carbocyclyl. In certain embodiments, at least one instance of $R^{A1}$ is unsubstituted carbocyclyl. In certain embodiments, at least one instance of $R^{A1}$ is substituted heterocyclyl. In certain embodiments, at least one instance of $R^{A1}$ is unsubstituted heterocyclyl. In certain embodiments, at least one instance of $R^{A1}$ is substituted aryl. In certain embodiments, at least one instance of $R^{A1}$ is unsubstituted aryl. In certain embodiments, at least one instance of $R^{A1}$ is substituted phenyl. In certain embodiments, at least one instance of $R^{A1}$ is unsubstituted phenyl. In certain embodiments, at least one instance of $R^{A1}$ is substituted heteroaryl. In certain embodiments, at least one instance of $R^{A1}$ is unsubstituted heteroaryl. In certain embodiments, at least one instance of $R^{A1}$ is substituted pyridyl. In certain embodiments, at least one instance of $R^{A1}$ is unsubstituted pyridyl. In certain embodiments, at least one instance of $R^{A1}$ is a nitrogen protecting group (e.g., Bn, BOC, Cbz, Fmoc, trifluoroacetyl, triphenylmethyl, acetyl, or Ts).

In certain embodiments, at least one $R^{A1}$ is hydrogen, $C_{1-6}$ alkyl, or a nitrogen protecting group. In certain embodiments, all instances of $R^{A1}$ are each independently hydrogen, $C_{1-6}$ alkyl, or a nitrogen protecting group. In certain embodiments, all instances of $R^{A1}$ are hydrogen.

In Formulae (I') and (II), Ring A may be substituted with one or more $R^{A2}$ groups when the $R^{A2}$ group is attached to a carbon atom. In certain embodiments, at least one $R^{A2}$ is H. In certain embodiments, at least one $R^{A2}$ is halogen. In certain embodiments, at least one $R^{A2}$ is F. In certain embodiments, at least one $R^{A2}$ is Cl. In certain embodiments, at least one $R^{A2}$ is Br. In certain embodiments, at least one $R^{A2}$ is I (iodine). In certain embodiments, at least one $R^{A2}$ is substituted acyl. In certain embodiments, at least one $R^{A2}$ is unsubstituted acyl. In certain embodiments, at least one $R^{A2}$ is acetyl. In certain embodiments, at least one $R^{A2}$ is substituted acetyl. In certain embodiments, at least one $R^{A2}$ is substituted alkyl. In certain embodiments, at least one $R^{A2}$ is unsubstituted alkyl. In certain embodiments, at least one $R^{A2}$ is $C_{1-6}$ alkyl. In certain embodiments, at least one $R^{A2}$ is methyl. In certain embodiments, at least one $R^{A2}$ is ethyl. In certain embodiments, at least one $R^{A2}$ is propyl. In certain embodiments, at least one $R^{A2}$ is butyl. In certain embodiments, at least one $R^{A2}$ is substituted alkenyl. In certain embodiments, at least one $R^{A2}$ is unsubstituted alkenyl. In certain embodiments, at least one $R^{A2}$ is vinyl. In certain embodiments, at least one $R^{A2}$ is substituted alkynyl. In certain embodiments, at least one $R^{A2}$ is unsubstituted alkynyl. In certain embodiments, at least one $R^{A2}$ is ethynyl. In certain embodiments, at least one $R^{A2}$ is substituted carbocyclyl. In certain embodiments, at least one $R^{A2}$ is unsubstituted carbocyclyl. In certain embodiments, at least one $R^{A2}$ is substituted heterocyclyl. In certain embodiments, at least one $R^{A2}$ is unsubstituted heterocyclyl. In certain embodiments, at least one $R^{A2}$ is substituted aryl. In certain embodiments, at least one $R^{A2}$ is unsubstituted aryl. In certain embodiments, at least one $R^{A2}$ is substituted phenyl. In certain embodiments, at least one $R^{A2}$ is unsubstituted phenyl. In certain embodiments, at least one $R^{A2}$ is substituted heteroaryl. In certain embodiments, at least one $R^{A2}$ is unsubstituted heteroaryl. In certain embodiments, at least one $R^{A2}$ is substituted pyridyl. In certain embodiments, at least one $R^{A2}$ is unsubstituted pyridyl. In certain embodiments, at least one $R^{A2}$ is —CN. In certain embodiments, at least one $R^{A2}$ is —$OR^{A2a}$. In certain embodiments, at least one $R^{A2}$ is —$N(R^{A2b})_2$. In certain embodiments, at least one $R^{A2}$ is —$SR^{A2a}$.

In certain embodiments, two $R^{A2}$ groups are each independently halogen, optionally substituted alkyl, or optionally substituted aryl; and all other instances of $R^{A2}$ are hydrogen. In certain embodiments, two $R^{A2}$ groups are each independently halogen or optionally substituted alkyl; and all other instances of $R^{A2}$ are hydrogen. In certain embodiments, two $R^{A2}$ groups are halogen; and all other instances of $R^{A2}$ are hydrogen. In certain embodiments, two $R^{A2}$ groups are optionally substituted alkyl; and all other instances of $R^{A2}$ are hydrogen. In certain embodiments, two $R^{A2}$ groups are $C_{1-6}$ alkyl; and all other instances of $R^{A2}$ are hydrogen. In certain embodiments, two $R^{A2}$ groups are methyl; and all other instances of $R^{A2}$ are hydrogen. In certain embodiments, two $R^{A2}$ groups are ethyl; and all other instances of $R^{A2}$ are hydrogen. In certain embodiments, two $R^{A2}$ groups are propyl; and all other instances of $R^{A2}$ are hydrogen. In certain embodiments, two $R^{A2}$ groups are butyl; and all other instances of $R^{A2}$ are hydrogen. In certain embodiments, two $R^{A2}$ groups are optionally substituted aryl; and all other instances of $R^{A2}$ are hydrogen. In certain embodiments, two $R^{A2}$ groups are optionally substituted phenyl; and all other instances of $R^{A2}$ are hydrogen.

In certain embodiments, one $R^{A2}$ groups is halogen, optionally substituted alkyl, or optionally substituted aryl; and all other instances of $R^{A2}$ are hydrogen. In certain embodiments, one $R^{A2}$ is halogen or optionally substituted alkyl; and all other instances of $R^{A2}$ are hydrogen. In certain embodiments, one $R^{A2}$ is halogen; and all other instances of $R^{A2}$ are hydrogen. In certain embodiments, one $R^{A2}$ is optionally substituted alkyl; and all other instances of $R^{A2}$ are hydrogen. In certain embodiments, one $R^{A2}$ is $C_{1-6}$ alkyl; and all other instances of $R^{A2}$ are hydrogen. In certain embodiments, one $R^{A2}$ is methyl; and all other instances of $R^{A2}$ are hydrogen. In certain embodiments, one $R^{A2}$ is ethyl; and all other instances of $R^{A2}$ are hydrogen. In certain embodiments, one $R^{A2}$ is propyl; and all other instances of $R^{A2}$ are hydrogen. In certain embodiments, one $R^{A2}$ is butyl; and all other instances of $R^{A2}$ are hydrogen. In certain embodiments, one $R^{A2}$ is optionally substituted aryl; and all other instances of $R^{A2}$ are hydrogen. In certain embodiments, one $R^{A2}$ is optionally substituted phenyl; and all other instances of $R^{A2}$ are hydrogen. In certain embodiments, all instances of $R^{A2}$ are hydrogen.

In certain embodiments, when $R^{A2}$ is —$OR^{A2a}$ or —$SR^{A2a}$, $R^{A2a}$ is H. In certain embodiments, $R^{A2a}$ is halogen. In certain embodiments, $R^{A2a}$ is F. In certain embodiments, $R^{A2a}$ is Cl. In certain embodiments, $R^{A2a}$ is Br. In certain embodiments, $R^{A2a}$ is I (iodine). In certain embodiments, $R^{A2a}$ is substituted acyl. In certain embodiments, $R^{A2a}$ is unsubstituted acyl. In certain embodiments, $R^{A2a}$ is acetyl. In certain embodiments, $R^{A2a}$ is substituted acetyl. In certain embodiments, $R^{A2a}$ is substituted alkyl. In certain embodiments, $R^{A2a}$ is unsubstituted alkyl. In certain embodiments, $R^{A2a}$ is $C_{1-6}$ alkyl. In certain embodiments, $R^{A2a}$ is methyl. In certain embodiments, $R^{A2a}$ is ethyl. In certain embodiments, $R^{A2a}$ is propyl. In certain embodiments, $R^{A2a}$ is butyl. In certain embodiments, $R^{A2a}$ is substituted alkenyl. In certain embodiments, $R^{A2a}$ is unsubstituted alkenyl. In certain embodiments, $R^{A2a}$ is vinyl. In certain embodiments, $R^{A2a}$ is substituted alkynyl. In certain embodiments, $R^{A2a}$ is unsubstituted alkynyl. In certain embodiments, $R^{A2a}$ is ethynyl. In certain embodiments, $R^{A2a}$ is substituted carbocyclyl. In certain embodiments, $R^{A2a}$ is unsubstituted carbocyclyl. In certain embodiments, $R^{A2a}$ is substituted heterocyclyl. In certain embodiments, $R^{A2a}$ is unsubstituted heterocyclyl. In certain embodiments, $R^{A2a}$ is substituted aryl. In certain embodiments, $R^{A2a}$ is unsubstituted aryl. In certain embodiments, $R^{A2a}$ is substituted phenyl. In certain embodiments, $R^{A2a}$ is unsubstituted phenyl. In certain embodiments, $R^{A2a}$ is substituted heteroaryl. In certain embodiments, $R^{A2a}$ is unsubstituted heteroaryl. In certain embodiments, $R^{A2a}$ is substituted pyridyl. In certain embodiments, $R^{A2a}$ is unsubstituted pyridyl. In certain embodiments, $R^{A2a}$ is an oxygen protecting group when attached to an oxygen atom (e.g., silyl, TBDPS, TBDMS, TIPS, TES, TMS, MOM, THP, t-Bu, Bn, allyl, acetyl, pivaloyl, or benzoyl). In certain embodiments, $R^{A2a}$ is a sulfur protecting group when attached to a sulfur atom. In certain embodiments, $R^{A2a}$ is acetamidomethyl, t-Bu, 3-nitro-2-pyridine sulfenyl, 2-pyridine-sulfenyl, or triphenylmethyl when attached to a sulfur atom.

In certain embodiments, when $R^{A2}$ is $-N(R^{A2b})_2$, at least one $R^{A2b}$ is H. In certain embodiments, at least one $R^{A2b}$ is halogen. In certain embodiments, at least one $R^{A2b}$ is F. In certain embodiments, at least one $R^{A2b}$ is Cl. In certain embodiments, at least one $R^{A2b}$ is Br. In certain embodiments, at least one $R^{A2b}$ is I (iodine). In certain embodiments, at least one $R^{A2b}$ is substituted acyl. In certain embodiments, at least one $R^{A2b}$ is unsubstituted acyl. In certain embodiments, at least one $R^{A2b}$ is acetyl. In certain embodiments, at least one $R^{A2b}$ is substituted acetyl. In certain embodiments, at least one $R^{A2b}$ is substituted alkyl. In certain embodiments, at least one $R^{A2b}$ is unsubstituted alkyl. In certain embodiments, at least one $R^{A2b}$ is $C_{1-6}$ alkyl. In certain embodiments, at least one $R^{A2b}$ is methyl. In certain embodiments, at least one $R^{A2b}$ is ethyl. In certain embodiments, at least one $R^{A2b}$ is propyl. In certain embodiments, at least one $R^{A2b}$ is butyl. In certain embodiments, at least one $R^{A2b}$ is substituted alkenyl. In certain embodiments, at least one $R^{A2b}$ is unsubstituted alkenyl. In certain embodiments, at least one $R^{A2b}$ is vinyl. In certain embodiments, at least one $R^{A2b}$ is substituted alkynyl. In certain embodiments, at least one $R^{A2b}$ is unsubstituted alkynyl. In certain embodiments, at least one $R^{A2b}$ is ethynyl. In certain embodiments, at least one $R^{A2b}$ is substituted carbocyclyl. In certain embodiments, at least one $R^{A2b}$ is unsubstituted carbocyclyl. In certain embodiments, at least one $R^{A2b}$ is substituted heterocyclyl. In certain embodiments, at least one $R^{A2b}$ is unsubstituted heterocyclyl. In certain embodiments, at least one $R^{A2b}$ is substituted aryl. In certain embodiments, at least one $R^{A2b}$ is unsubstituted aryl. In certain embodiments, at least one $R^{A2b}$ is substituted phenyl. In certain embodiments, at least one $R^{A2b}$ is unsubstituted phenyl. In certain embodiments, at least one $R^{A2b}$ is substituted heteroaryl. In certain embodiments, at least one $R^{A2b}$ is unsubstituted heteroaryl. In certain embodiments, at least one $R^{A2b}$ is substituted pyridyl. In certain embodiments, at least one $R^{A2b}$ is unsubstituted pyridyl. In certain embodiments, at least one $R^{A2b}$ is a nitrogen protecting group when attached to a nitrogen atom. In certain embodiments, at least one $R^{A2b}$ is Bn, BOC, Cbz, Fmoc, trifluoroacetyl, triphenylmethyl, acetyl, or Ts when attached to a nitrogen atom. In certain embodiments, two $R^{A2b}$ groups are joined to form a substituted heterocyclic ring. In certain embodiments, two $R^{A2b}$ groups are joined to form an unsubstituted heterocyclic ring.

In Formulae (I') and (II), any two instances of $R^{A1}$, any two instances of $R^{A2}$, or one instance of $R^{A1}$ and one instance of $R^{A2}$ may be joined to form an optionally substituted carbocyclic, optionally substituted heterocyclic, optionally substituted aryl, or optionally substituted heteroaryl ring. In certain embodiments, two instances of $R^{A1}$ are joined to form a substituted or unsubstituted carbocyclic ring. In certain embodiments, two instances of $R^{A1}$ are joined to form a substituted or unsubstituted heterocyclic ring. In certain embodiments, two instances of $R^{A1}$ are joined to form a substituted or unsubstituted aryl ring. In certain embodiments, two instances of $R^{A1}$ are joined to form a substituted or unsubstituted heteroaryl ring. In certain embodiments, two instances of $R^{A2}$ are joined to form a substituted or unsubstituted carbocyclic ring. In certain embodiments, two instances of $R^{A2}$ are joined to form a substituted or unsubstituted heterocyclic ring. In certain embodiments, two instances of $R^{A2}$ are joined to form a substituted or unsubstituted aryl ring. In certain embodiments, two instances of $R^{A2}$ are joined to form a substituted or unsubstituted heteroaryl ring. In certain embodiments, one instance of $R^{A1}$ and one instance of $R^{A2}$ are joined to form a substituted carbocyclic ring. In certain embodiments, one instance of $R^{A1}$ and one instance of $R^{A2}$ are joined to form an unsubstituted carbocyclic ring. In certain embodiments, one instance of $R^{A1}$ and one instance of $R^{A2}$ are joined to form a substituted heterocyclic ring. In certain embodiments, one instance of $R^{A1}$ and one instance of $R^{A2}$ are joined to form an unsubstituted heterocyclic ring. In certain embodiments, one instance of $R^{A1}$ and one instance of $R^{A2}$ are joined to form a substituted aryl ring. In certain embodiments, one instance of $R^{A1}$ and one instance of $R^{A2}$ are joined to form an unsubstituted aryl ring. In certain embodiments, one instance of $R^{A1}$ and one instance of $R^{A2}$ are joined to form a substituted heteroaryl ring. In certain embodiments, one instance of $R^{A1}$ and one instance of $R^{A2}$ are joined to form an unsubstituted heteroaryl ring.

As generally defined herein, Formulae (I') and (II) include substituent $R^{1b}$. In certain embodiments, $R^{1b}$ is H. In certain embodiments, $R^{1b}$ is halogen. In certain embodiments, $R^{1b}$ is F. In certain embodiments, $R^{1b}$ is Cl. In certain embodiments, $R^{1b}$ is Br. In certain embodiments, $R^{1b}$ is I (iodine). In certain embodiments, $R^{1b}$ is substituted acyl. In certain embodiments, $R^{1b}$ is unsubstituted acyl. In certain embodiments, $R^{1b}$ is acetyl. In certain embodiments, $R^{1b}$ is substituted acetyl. In certain embodiments, $R^{1b}$ is substituted alkyl. In certain embodiments, $R^{1b}$ is unsubstituted alkyl. In certain embodiments, $R^{1b}$ is $C_{1-6}$ alkyl. In certain embodiments, $R^{1b}$ is methyl. In certain embodiments, $R^{1b}$ is ethyl. In certain embodiments, $R^{1b}$ is propyl. In certain embodiments, $R^{1b}$ is butyl. In certain embodiments, $R^{1b}$ is substituted alkenyl. In certain embodiments, $R^{1b}$ is unsubstituted alkenyl. In certain embodiments, $R^{1b}$ is vinyl. In certain embodiments, $R^{1b}$ is substituted alkynyl. In certain embodiments, $R^{1b}$ is unsubstituted alkynyl. In certain embodiments, $R^{1b}$ is ethynyl. In certain embodiments, $R^{1b}$ is substituted carbocyclyl. In certain embodiments, $R^{1b}$ is unsubstituted carbocyclyl. In certain embodiments, $R^{1b}$ is substituted aryl. In certain embodiments, $R^{1b}$ is unsubstituted aryl. In certain embodiments, $R^{1b}$ is substituted phenyl. In certain embodiments, $R^{1b}$ is unsubstituted phenyl. In certain embodiments, $R^{1b}$ is substituted heteroaryl. In certain embodiments, $R^{1b}$ is unsubstituted heteroaryl. In certain embodiments, $R^{1b}$ is substituted pyridyl. In certain embodiments, $R^{1b}$ is unsubstituted pyridyl. In certain embodiments, $R^{1b}$ is —CN. In certain embodiments, $R^{1b}$ is —$OR^{B1a}$. In certain embodiments, $R^{1b}$ is —$N(R^{B1b})_2$ (e.g., —$NMe_2$). In certain embodiments, $R^{1b}$ is —$SR^{B1a}$. In certain embodiments, $R^{1b}$ is hydrogen, halogen, substituted or unsubstituted $C_{1-6}$ alkyl, —CN, —$OR^{B1a}$, or —$N(R^{B1b})_2$. In certain embodiments, $R^{1b}$ is hydrogen, halogen, —CN, —$OR^{B1a}$, —$N(R^{B1b})_2$, unsubstituted $C_{1-6}$ alkyl, or $C_{1-6}$ alkyl substituted with one or more halogen, wherein each instance of $R^{B1a}$ is independently hydrogen, unsubstituted $C_{1-6}$ alkyl, or $C_{1-6}$ alkyl substituted with one or more halogen; and each occurrence of $R^{B1b}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group.

In certain embodiments, when $R^{B1b}$ is —$OR^{B1a}$ or —$SR^{B1a}$, $R^{B1a}$ is H. In certain embodiments, $R^{B1a}$ is substituted acyl. In certain embodiments, $R^{B1a}$ is unsubstituted acyl. In certain embodiments, $R^{B1a}$ is acetyl. In certain embodiments, $R^{B1a}$ is substituted acetyl. In certain embodiments, $R^{B1a}$ is substituted alkyl. In certain embodiments, $R^{B1a}$ is unsubstituted alkyl. In certain embodiments, $R^{B1a}$ is $C_{1-6}$ alkyl. In certain embodiments, $R^{B1a}$ is methyl. In certain embodiments, $R^{B1a}$ is ethyl. In certain embodiments, $R^{B1a}$ is propyl. In certain embodiments, $R^{B1a}$ is butyl. In certain embodiments, $R^{B1a}$ is substituted alkenyl. In certain embodiments, $R^{B1a}$ is unsubstituted alkenyl. In certain embodiments, $R^{B1a}$ is vinyl. In certain embodiments, $R^{B1a}$ is substituted alkynyl. In certain embodiments, $R^{B1a}$ is unsubstituted alkynyl. In certain embodiments, $R^{B1a}$ is ethynyl. In certain embodiments, $R^{B1a}$ is substituted carbocyclyl. In certain embodiments, $R^{B1a}$ is unsubstituted carbocyclyl. In certain embodiments, $R^{B1a}$ is substituted heterocyclyl. In certain embodiments, $R^{B1a}$ is unsubstituted heterocyclyl. In certain embodiments, $R^{B1a}$ is substituted aryl. In certain embodiments, $R^{B1a}$ is unsubstituted aryl. In certain embodiments, $R^{B1a}$ is substituted phenyl. In certain embodiments, $R^{B1a}$ is unsubstituted phenyl. In certain embodiments, $R^{B1a}$ is substituted or unsubstituted heteroaryl. In certain embodiments, $R^{B1a}$ is substituted or unsubstituted pyridyl. In certain embodiments, $R^{B1a}$ is an oxygen protecting group when attached to an oxygen atom. In certain embodiments, $R^{B1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1a}$ is a sulfur protecting group when attached to a sulfur atom. In certain embodiments, $R^{B1a}$ is acetamidomethyl, t-Bu, 3-nitro-2-pyridine sulfenyl, 2-pyridine-sulfenyl, or triphenylmethyl when attached to a sulfur atom.

In certain embodiments, $R^{1b}$ is —$N(R^{B1b})_2$. In certain embodiments, at least one instance of $R^{B1b}$ is substituted acyl. In certain embodiments, at least one instance of $R^{B1b}$ is unsubstituted acyl. In certain embodiments, at least one instance of $R^{B1b}$ is substituted or unsubstituted acetyl. In certain embodiments, at least one instance of $R^{B1b}$ is substituted alkyl. In certain embodiments, at least one instance of $R^{B1b}$ is unsubstituted alkyl. In certain embodiments, at least one instance of $R^{B1b}$ is $C_{1-6}$ alkyl. In certain embodiments, at least one instance of $R^{B1b}$ is methyl. In certain embodiments, at least one instance of $R^{B1b}$ is ethyl. In certain embodiments, at least one instance of $R^{B1b}$ is propyl. In certain embodiments, at least one instance of $R^{B1b}$ is butyl. In certain embodiments, at least one instance of $R^{B1b}$ is substituted alkenyl. In certain embodiments, at least one instance of $R^{B1b}$ is unsubstituted alkenyl. In certain embodiments, $R^{B1b}$ is vinyl. In certain embodiments, at least one instance of $R^{B1b}$ is substituted alkynyl. In certain embodiments, at least one instance of $R^{B1b}$ is unsubstituted alkynyl. In certain embodiments, at least one instance of $R^{B1b}$ is ethynyl. In certain embodiments, at least one instance of $R^{B1b}$ is substituted carbocyclyl. In certain embodiments, at least one instance of $R^{B1b}$ is unsubstituted carbocyclyl. In certain embodiments, at least one instance of $R^{B1b}$ is substituted heterocyclyl. In certain embodiments, at least one instance of $R^{B1b}$ is unsubstituted heterocyclyl. In certain embodiments, at least one instance of $R^{B1b}$ is substituted aryl. In certain embodiments, at least one instance of $R^{B1b}$ is unsubstituted aryl. In certain embodiments, $R^{B1b}$ is substituted phenyl. In certain embodiments, $R^{B1b}$ is unsubstituted phenyl. In certain embodiments, at least one instance of $R^{B1b}$ is substituted or unsubstituted heteroaryl. In certain embodiments, at least one instance of $R^{B1b}$ is substituted or unsubstituted pyridyl. In certain embodiments, at least one instance of $R^{B1b}$ is a nitrogen protecting group when attached to a nitrogen atom (e.g., Bn, BOC, Cbz, Fmoc, trifluoroacetyl, triphenylmethyl, acetyl, or Ts). In certain embodiments, two instances of $R^{B1b}$ are taken together with their intervening atoms to form a substituted or unsubstituted heterocyclic or substituted or unsubstituted heteroaryl ring.

As generally defined herein, in Formulae (I') and (II), $R^2$ is a divalent linker moiety connecting Ring B and Ring C. In certain embodiments, $R^2$ is —O—. In certain embodiments, $R^2$ is —S—. In certain embodiments, $R^2$ is —$N(R^6)$—, wherein each $R^6$ is independently selected from hydrogen and —$C_1$-$C_6$ alkyl. In certain embodiments, $R^2$ is —NH—. In certain embodiments, $R^2$ is —$N(C_1$-$C_6$ alkyl)- (e.g., —N(Me). In certain embodiments, $R^2$ is an optionally substituted $C_1$-$C_4$ alkylene, wherein one or more methylene units of the alkylene are optionally and independently replaced with —O—, —S—, or —$N(R^6)$—. In certain embodiments, $R^2$ is an optionally substituted $C_2$ hydrocarbon chain, optionally wherein one or two carbon units of the hydrocarbon chain is replaced with —O—, —S—, or —$NR^6$—. In certain embodiments, $R^2$ is an optionally substituted $C_3$ hydrocarbon chain, optionally wherein one or more carbon units of the hydrocarbon chain is replaced with —O—, —S—, or —$NR^6$—. In certain embodiments, $R^2$ is an optionally substituted $C_4$ hydrocarbon chain, optionally wherein one or more carbon units of the hydrocarbon chain is replaced with —O—, —S—, or —$NR^6$—. In certain embodiments, at least one carbon unit of the $C_{1-4}$ hydrocarbon chain is substituted with one or more substituents independently selected from the group consisting of —O—, —S—, or —NR— (e.g., —NH— or —NMe-).

Formulae (I') and (II) include Ring C of the formula:

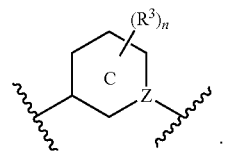

In certain embodiments, Z is —CH—. In certain embodiments, Z is N. In certain embodiments, Ring C is of formula:

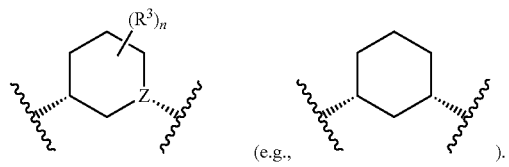

In certain embodiments, Ring C is of formula:

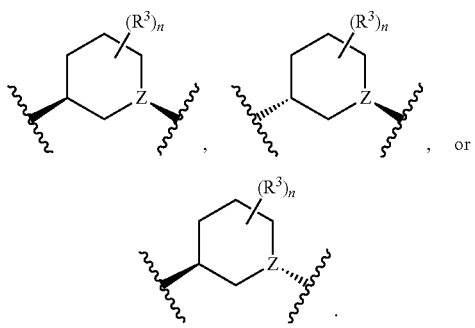

, or

In certain embodiments, Ring C is of formula:

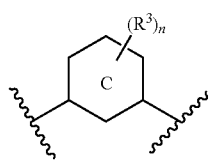

In certain embodiments, Ring C is of formula:

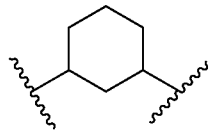

In certain embodiments, Ring C is of formula:

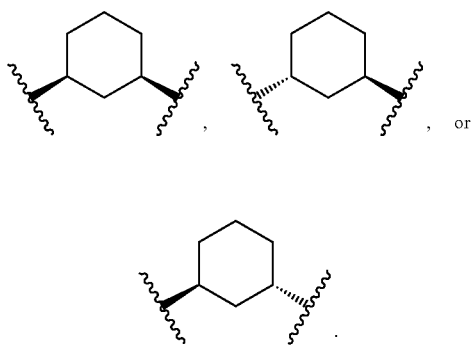

, or

In certain embodiments, Ring C is of formula:

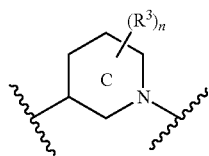

In certain embodiments, Ring C is of formula:

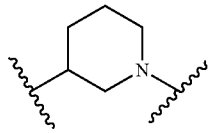

In certain embodiments, Ring C is of formula:

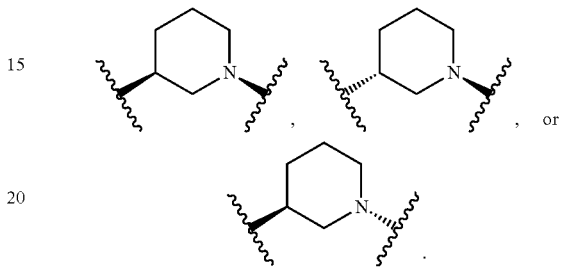

Ring C may include one or more instances of substituent $R^3$. In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6.

In certain embodiments, at least one instance of $R^3$ is halogen (e.g., F, Cl, Br, or I). In certain embodiments, at least one instance of $R^3$ is substituted or unsubstituted acyl (e.g., —C(=O)Me). In certain embodiments, at least one instance of $R^3$ is substituted or unsubstituted alkyl (e.g., substituted or unsubstituted $C_{1-6}$ alkyl). In certain embodiments, at least one instance of $R^3$ is substituted or unsubstituted methyl. In certain embodiments, at least one instance of $R^3$ is substituted or unsubstituted ethyl. In certain embodiments, at least one instance of $R^3$ is substituted or unsubstituted propyl. In certain embodiments, at least one instance of $R^3$ is substituted or unsubstituted alkenyl (e.g., substituted or unsubstituted $C_{2-6}$ alkenyl). In certain embodiments, at least one instance of $R^3$ is substituted or unsubstituted alkynyl (e.g., substituted or unsubstituted $C_{2-6}$ alkynyl). In certain embodiments, at least one instance of $R^3$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^3$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^3$ is substituted or unsubstituted aryl (e.g., substituted or unsubstituted, 6- to 10-membered aryl). In certain embodiments, at least one instance of $R^3$ is benzyl. In certain embodiments, at least one instance of $R^3$ is substituted or unsubstituted phenyl. In certain embodiments, at least one instance of $R^{A1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^3$ is —$OR^{C1}$ (e.g., —OH or —OMe). In certain embodiments, at least one instance of R³ is —N(R^{C1a})₂ (e.g., —NMe₂). In certain embodiments, at least one instance of R³ is —SR^{C1} (e.g., —SMe). In certain embodiments, two R³ groups bound to the same ring carbon atom are taken together to form =O. In certain embodiments, two R³ groups bound to the same or different ring carbon atoms are joined to form an optionally substituted carbocyclyl ring (e.g., substituted or unsubstituted, 3- to 7-membered, monocyclic carbocyclyl comprising zero, one, or two double bonds in the carbocyclic ring system). In certain embodiments, two R³ groups bound to the same or different ring carbon atoms are joined to form an optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two R³ groups bound to the same or different ring carbon atoms are joined to form an optionally substituted aryl. In certain embodiments, two R³ groups bound to the same or different ring carbon atoms are joined to form an optionally substituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, each occurrence of R^{C1} is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom. In certain embodiments, each occurrence of R^{C1a} is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of R^{C1a} are taken together with their intervening atoms to form a substituted or unsubstituted heterocyclic or substituted or unsubstituted heteroaryl ring.

As generally defined herein, in Formula (I'), R⁴ is a divalent linker moiety connecting Ring C and Ring D1. As generally defined herein, in Formula (I), R⁴ is a divalent linker moiety connecting Ring C and Ring D. In certain embodiments, R⁴ is a bond. In certain embodiments, R⁴ is a single bond. In certain embodiments, R⁴ is —C(=O)—. In certain embodiments, R⁴ is —O—. In certain embodiments, R⁴ is —S—. In certain embodiments, R⁴ is —N(R⁶)— (e.g., —NH—). In certain embodiments, R⁴ is —S(=O)₂—. In certain embodiments, R⁴ is an optionally substituted C₁-C₄ alkylene, wherein: one or more methylene units of the alkylene other than a methylene unit bound to a nitrogen atom is optionally and independently replaced with —C(=O)—, —O—, —S—, —N(R⁶)—, or —S(=O)₂—. In certain embodiments, R⁴ is an optionally substituted C₂ hydrocarbon chain, optionally wherein one or two carbon units of the hydrocarbon chain is replaced with —O—, —S—, —NR⁶—, or —S(=O)₂—. In certain embodiments, R⁴ is —NR⁶C(=O)—, —C(=O)NR⁶—, —NR⁶S(=O)₂—, —S(=O)₂NR⁶—, —NR⁶(C₁-₂ alkylene)-, or —(C₁-₂ alkylene)NR⁶—. In certain embodiments, R⁴ is —NR⁶C(=O)—, —C(=O)NR⁶—, —NR⁶S(=O)₂—, —S(=O)₂NR⁶—, —NR⁶(C₁-₂ alkylene)-. In certain embodiments, R⁴ is —NHC(=O)—, —C(=O)NH—, —NHS(=O)₂—, —N(C(O)OC(CH₃)₃)—, —N(Boc)CH₂—, —NH—, —NHCH₂—, —NMeCH₂—, or —OCH₂—. In certain embodiments, R⁴ is an optionally substituted C₄ hydrocarbon chain, optionally wherein one or more carbon units of the hydrocarbon chain is replaced with —C(=O)—, —O—, —S—, —N(R⁶)—, or —S(=O)₂—. In certain embodiments, at least one carbon unit of the C₁-₄ hydrocarbon chain is substituted with one or more substituents independently selected from the group consisting of —C(=O)—, —O—, —S—, —N(R⁶)—, or —S(=O)₂—.

Formula (I') includes Ring D1 of the formula:

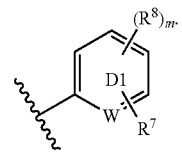

wherein W is —CR^{D1}= or —N=, and R^{D1} is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, Ring D1 is

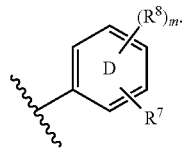

In certain embodiments, W is —CH=. In certain embodiments, W is —C(Me)-. In certain embodiments, W is —N=.

In certain embodiments, Ring D1 is a compound of Ring D of the formula:

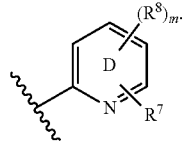

Formula (I) includes Ring D of the formula:

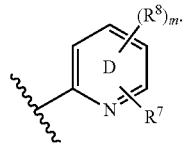

Ring D includes zero or more instances of substituent R⁸. In certain embodiments, m is 0. In certain embodiments, m is 1. In certain embodiments, m is 2. In certain embodiments, m is 3. In certain embodiments, m is 4. In certain embodiments, at least one instance of R⁸ is hydrogen. halogen (e.g., F, Cl, Br, or I). In certain embodiments, at least one instance of $R^8$ is F. In certain embodiments, at least one instance of $R^8$ is Cl. In certain embodiments, at least one instance of $R^8$ is Br. In certain embodiments, at least one instance of $R^8$ is I (iodine). In certain embodiments, at least one instance of $R^8$ is substituted or unsubstituted acyl (e.g., —C(=O)Me). In certain embodiments, at least one instance of $R^8$ is substituted or unsubstituted alkyl (e.g., substituted or unsubstituted $C_{1-6}$ alkyl). In certain embodiments, at least one instance of $R^8$ is substituted or unsubstituted $C_{1-6}$ alkyl. In certain embodiments, at least one instance of $R^8$ is unsubstituted $C_{1-6}$ alkyl. In certain embodiments, at least one instance of $R^8$ is substituted or unsubstituted methyl. In certain embodiments, at least one instance of $R^8$ is substituted methyl. In certain embodiments, at least one instance of $R^8$ is unsubstituted methyl. In certain embodiments, at least one instance of $R^8$ is substituted or unsubstituted ethyl. In certain embodiments, at least one instance of $R^8$ is substituted or unsubstituted propyl. In certain embodiments, at least one instance of $R^8$ is substituted or unsubstituted alkenyl (e.g., substituted or unsubstituted $C_{2-6}$ alkenyl). In certain embodiments, at least one instance of $R^8$ is substituted or unsubstituted alkynyl (e.g., substituted or unsubstituted $C_{2-6}$ alkynyl). In certain embodiments, at least one instance of $R^8$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^8$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^8$ is substituted or unsubstituted aryl (e.g., substituted or unsubstituted, 6- to 10-membered aryl). In certain embodiments, at least one instance of $R^8$ is benzyl. In certain embodiments, at least one instance of $R^8$ is substituted or unsubstituted phenyl. In certain embodiments, at least one instance of $R^8$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^8$ is —$OR^{D1}$ (e.g., —OH or —OMe). In certain embodiments, at least one instance of $R^8$ is —OH. In certain embodiments, at least one instance of $R^8$ is —OMe. In certain embodiments, at least one instance of $R^8$ is —O($C_{1-6}$ alkyl). In certain embodiments, at least one instance of $R^8$ is —$N(R^{D1a})_2$ (e.g., —$NMe_2$). In certain embodiments, at least one instance of $R^8$ is —$NMe_2$. In certain embodiments, at least one instance of $R^8$ is —$SR^{D1}$ (e.g., —SMe). In certain embodiments, at least one instance of $R^8$ is halogen, —O(alkyl), or optionally substituted alkyl. In certain embodiments, two $R^8$ groups are joined to form an optionally substituted carbocyclyl (e.g., substituted or unsubstituted, 3- to 7-membered, monocyclic carbocyclyl comprising zero, one, or two double bonds in the carbocyclic ring system). In certain embodiments, two $R^8$ groups are joined to form an optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two $R^8$ groups are joined to form an optionally substituted aryl ring (e.g., substituted or unsubstituted, 6- to 10-membered aryl). In certain embodiments, two $R^8$ groups are joined to form an optionally substituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, each occurrence of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom. In certain embodiments, each occurrence of $R^{D1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of $R^{D1a}$ are taken together with their intervening atoms to form a substituted or unsubstituted heterocyclic or substituted or unsubstituted heteroaryl ring.

Formula (II) includes Ring E of the formula:

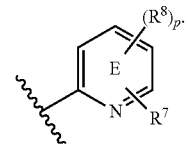

Ring E includes zero or more instances of substituent $R^8$. In certain embodiments, p is 0. In certain embodiments, p is 1. In certain embodiments, p is 2. In certain embodiments, m is 3. In certain embodiments, p is 4. In certain embodiments, p is 5. In certain embodiments, at least one instance of $R^8$ is hydrogen. In certain embodiments, at least one instance of $R^8$ is halogen (e.g., F, Cl, Br, or I). In certain embodiments, at least one instance of $R^8$ is F. In certain embodiments, at least one instance of $R^8$ is Cl. In certain embodiments, at least one instance of $R^8$ is Br. In certain embodiments, at least one instance of $R^8$ is I (iodine). In certain embodiments, at least one instance of $R^8$ is substituted or unsubstituted acyl (e.g., —C(=O)Me). In certain embodiments, at least one instance of $R^8$ is substituted or unsubstituted alkyl (e.g., substituted or unsubstituted $C_{1-6}$ alkyl). In certain embodiments, at least one instance of $R^8$ is substituted or unsubstituted $C_{1-6}$ alkyl. In certain embodiments, at least one instance of $R^8$ is unsubstituted $C_{1-6}$ alkyl. In certain embodiments, at least one instance of $R^8$ is substituted or unsubstituted methyl. In certain embodiments, at least one instance of $R^8$ is substituted methyl. In certain embodiments, at least one instance of $R^8$ is unsubstituted methyl. In certain embodiments, at least one instance of $R^8$ is substituted or unsubstituted ethyl. In certain embodiments, at least one instance of $R^8$ is substituted or unsubstituted propyl. In certain embodiments, at least one instance of $R^8$ is substituted or unsubstituted alkenyl (e.g., substituted or unsubstituted $C_{2-6}$ alkenyl). In certain embodiments, at least one instance of $R^8$ is substituted or unsubstituted alkynyl (e.g., substituted or unsubstituted $C_{2-6}$ alkynyl). In certain embodiments, at least one instance of $R^8$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^8$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^8$ is substituted or unsubstituted aryl (e.g., substituted or unsubstituted, 6- to 10-membered aryl). In certain embodiments, at least one instance of $R^8$ is benzyl. In certain embodiments, at least one instance of $R^8$ is substituted or unsubstituted phenyl. In certain embodiments, at least one instance of $R^8$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^8$ is —$OR^{D1}$ (e.g., —OH or —OMe). In certain embodiments, at least one instance of $R^8$ is —OH. In certain embodiments, at least one instance of $R^8$ is —OMe. In certain embodiments, at least one instance of $R^8$ is —$O(C_{1-6}$ alkyl). In certain embodiments, at least one instance of $R^8$ is —$N(R^{D1a})_2$ (e.g., —$NMe_2$). In certain embodiments, at least one instance of $R^8$ is —$NMe_2$. In certain embodiments, at least one instance of $R^8$ is —$SR^{D1}$ (e.g., —SMe). In certain embodiments, two $R^8$ groups are joined to form an optionally substituted carbocyclyl (e.g., substituted or unsubstituted, 3- to 7-membered, monocyclic carbocyclyl comprising zero, one, or two double bonds in the carbocyclic ring system). In certain embodiments, two $R^8$ groups are joined to form an optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two $R^8$ groups are joined to form an optionally substituted aryl ring (e.g., substituted or unsubstituted, 6- to 10-membered aryl). In certain embodiments, two $R^8$ groups are joined to form an optionally substituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, each occurrence of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, or a sulfur protecting group when attached to a sulfur atom. In certain embodiments, each occurrence of $R^{D1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of $R^{D1a}$ are taken together with their intervening atoms to form a substituted or unsubstituted heterocyclic or substituted or unsubstituted heteroaryl ring.

As generally defined herein, Formulae (I') and (II) include substituent $R^7$, wherein $R^7$ is a warhead of formula:

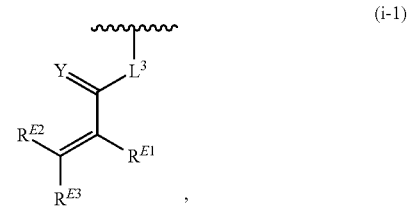

(i-1)

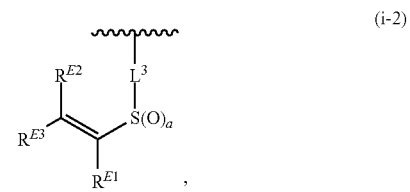

(i-2)

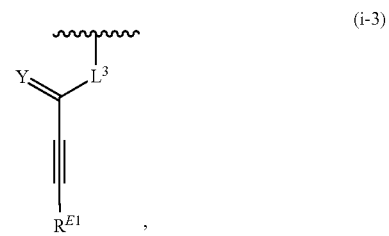

(i-3)

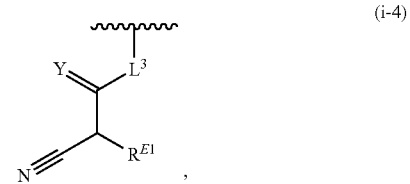

(i-4)

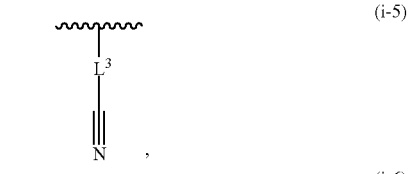

(i-5)

(i-6)

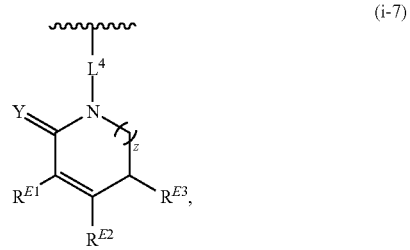

(i-7)

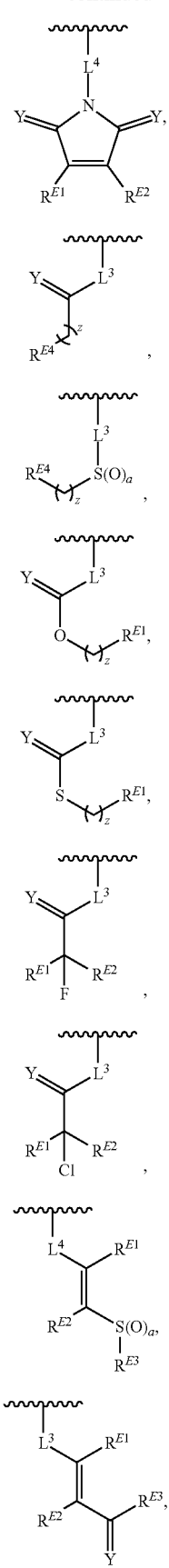
(i-8)
(i-9)
(i-10)
(i-11)
(i-12)
(i-13)
(i-14)
(i-15)
(i-16)
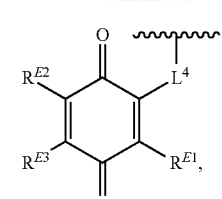 (i-17)
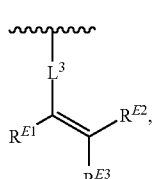 (i-18)
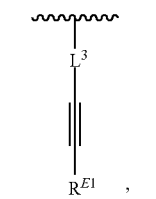 (i-19)
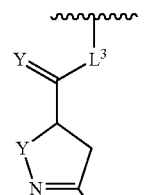 (i-20)
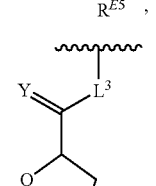 (i-21)
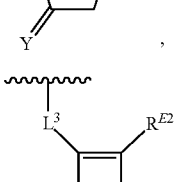 (i-22)
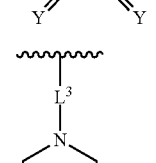 (i-23)
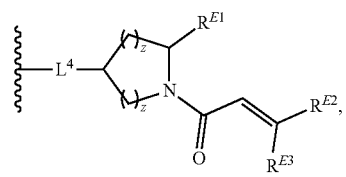 (i-24)

-continued
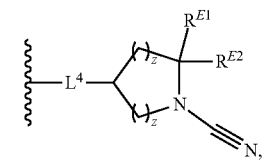 (i-25)
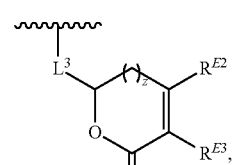 (i-26)
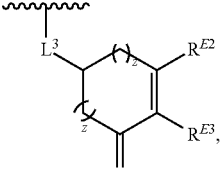 (i-27)
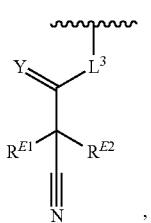 (i-28)
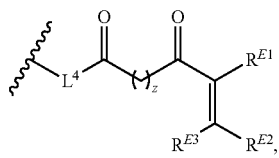 (i-29)
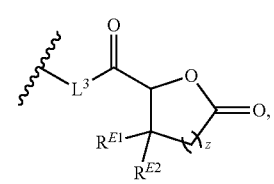 (i-30)
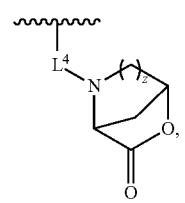 (i-31)
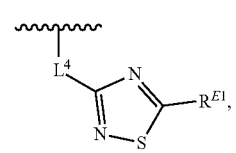 (i-32)
-continued
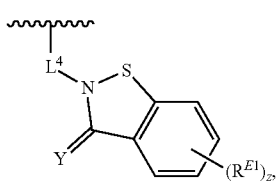 (i-33)
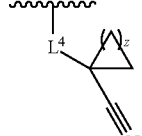 (i-34)
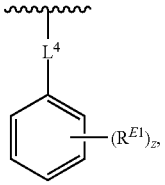 (i-35)
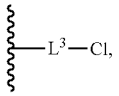 (i-36)
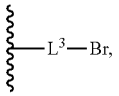 (i-37)
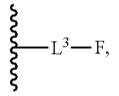 (i-38)
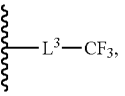 (i-39)
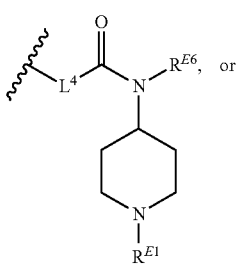 (i-40)
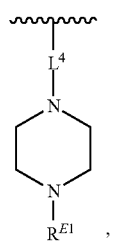 (i-41)
wherein:
$L^3$ is a bond or an optionally substituted $C_{1-4}$ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring; L$^4$ is a bond or an optionally substituted, branched or unbranched C$_{1-6}$ hydrocarbon chain; each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring; R$^{E4}$ is a leaving group; R$^{E5}$ is halogen; R$^{E6}$ is hydrogen, substituted or unsubstituted C$_{1-6}$ alkyl, or a nitrogen protecting group; each instance of Y is independently O, S, or NR$^{E7}$, wherein R$^{E7}$ is hydrogen, substituted or unsubstituted C$_{1-6}$ alkyl, or a nitrogen protecting group; a is 1 or 2; and each instance of z is independently 0, 1, 2, 3, 4, 5, or 6, as valency permits.

In certain embodiments, R$^7$ is a warhead of formula (i-1) through (i-41). In certain embodiments, the warhead is of formula

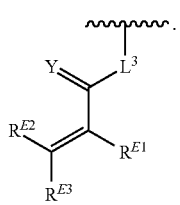

(i-1)

In certain embodiments, R$^7$ is a warhead is of formula

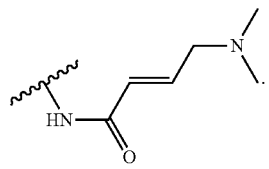 [SMILES: *NC(=O)/C=C/CN(C)C]

In certain embodiments, R$^7$ is a warhead is of formula

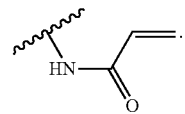

In certain embodiments, the warhead is of formula (i-2)

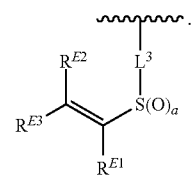

In certain embodiments, the warhead is of formula (i-3)

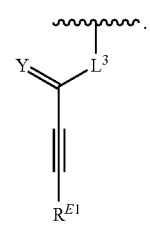

In certain embodiments, the warhead is of formula (i-4)

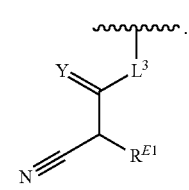

In certain embodiments, the warhead is of formula (i-5)

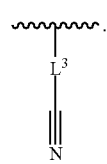

In certain embodiments, the warhead is of formula

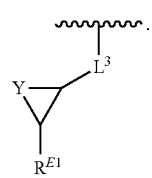
(i-6)

In certain embodiments, the warhead is

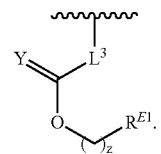
(i-11)

In certain embodiments, the warhead is of formula

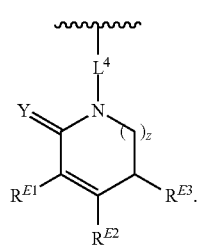
(i-7)

In certain embodiments, the warhead is of formula

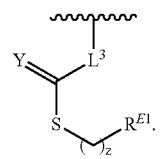
(i-12)

In certain embodiments, the warhead is of formula

In certain embodiments, the warhead is of formula

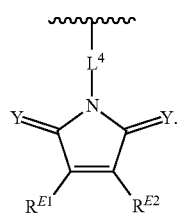
(i-8)

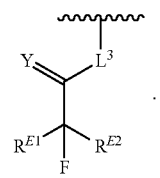
(i-13)

In certain embodiments, the warhead is of formula

In certain embodiments, the warhead is of formula

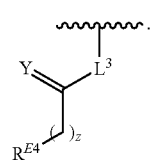
(i-9)

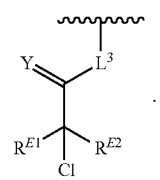
(i-14)

In certain embodiments, the warhead is of formula

In certain embodiments, the warhead is of formula

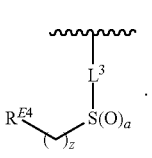
(i-10)

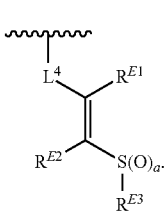
(i-15)

In certain embodiments, the warhead is of formula

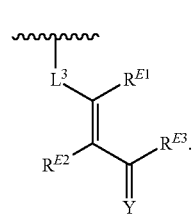

(i-16)

In certain embodiments, the warhead is of formula

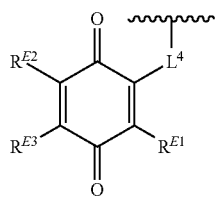

(i-17)

In certain embodiments, the warhead is of formula

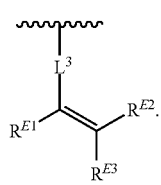

(i-18)

In certain embodiments, the warhead is of formula

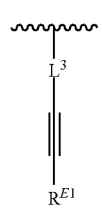

(i-19)

In certain embodiments, the warhead is of formula

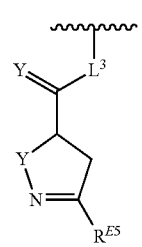

(i-20)

In certain embodiments, the warhead is

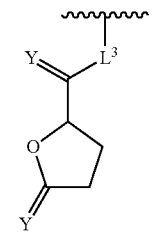

(i-21)

In certain embodiments, the warhead is of formula

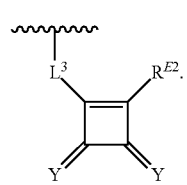

(i-22)

In certain embodiments, the warhead is of formula

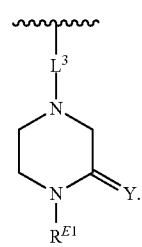

(i-23)

In certain embodiments, the warhead is of formula

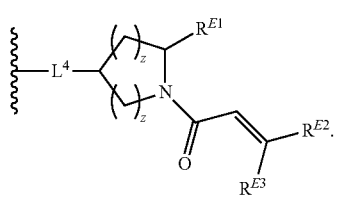

(i-24)

In certain embodiments, the warhead is of formula

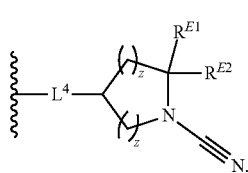

(i-25)

In certain embodiments, the warhead is of formula

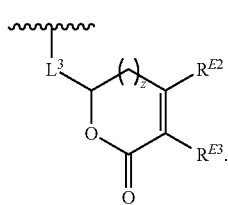

(i-26)

In certain embodiments, the warhead is of formula

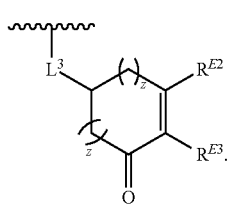

(i-27)

In certain embodiments, the warhead is of formula

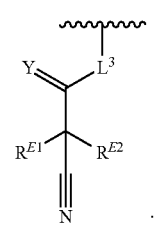

(i-28)

In certain embodiments, the warhead is of formula

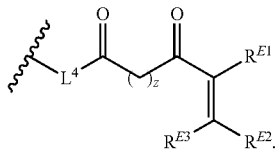

(i-29)

In certain embodiments, the warhead is of formula

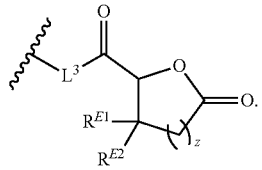

(i-30)

In certain embodiments, the warhead is of formula

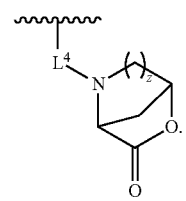

(i-31)

In certain embodiments, the warhead is of formula

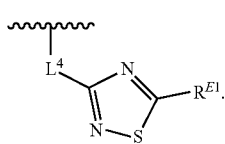

(i-32)

In certain embodiments, the warhead is of formula

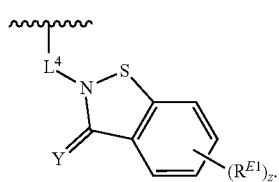

(i-33)

In certain embodiments, the warhead is of formula

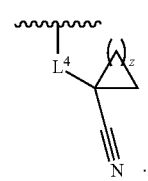

(i-34)

In certain embodiments, the warhead is of formula

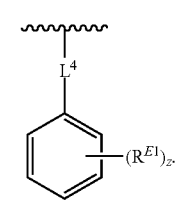

(i-35)

In certain embodiments, the warhead is of formula

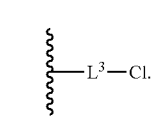

(i-36)

In certain embodiments, the warhead is of formula

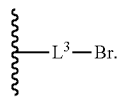

(i-37)

In certain embodiments, the warhead is of formula

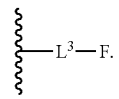

(i-38)

In certain embodiments, the warhead is of formula

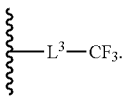

(i-39)

In certain embodiments, the warhead is of formula

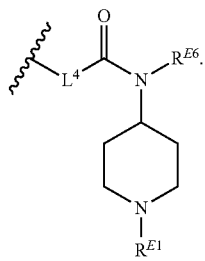

(i-40)

In certain embodiments, the warhead is of formula

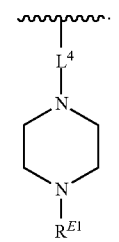

(i-41)

In certain embodiments, $L^3$ is a bond (e.g., a single bond, a double bond, or a triple bond). In certain embodiments, $L^3$ is a single bond. In certain embodiments, $L^3$ is a double bond. In certain embodiments, $L^3$ is a triple bond. In certain embodiments, $L^3$ is an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$— C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring. In certain embodiments, $L^4$ is a bond (e.g., a single bond, a double bond, or a triple bond). In certain embodiments, $L^4$ is an optionally substituted branched $C_{1-6}$ hydrocarbon chain (e.g., i-Pr). In certain embodiments, $L^4$ is an optionally substituted unbranched $C_{1-6}$ hydrocarbon chain (e.g., n-Pr, or n-Bu). In certain embodiments, at least one instance of R$^{E1}$ is H. In certain embodiments, at least one instance of R$^{E1}$ is halogen (e.g., F, Cl, Br, or I). In certain embodiments, at least one instance of R$^{E1}$ is optionally substituted alkyl (e.g., Me, or Et). In certain embodiments, at least one instance of R$^{E1}$ is optionally substituted alkenyl (e.g., optionally substituted vinyl). In certain embodiments, at least one instance of R$^{E1}$ is optionally substituted alkynyl. In certain embodiments, at least one instance of R$^{E1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of R$^{E1}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of R$^{E1}$ is substituted or unsubstituted aryl (e.g., substituted or unsubstituted, 6- to 10-membered aryl). In certain embodiments, at least one instance of R$^{E1}$ is substituted or unsubstituted phenyl. In certain embodiments, at least one instance of R$^{E1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of R$^{E1}$ is —CN. In certain embodiments, at least one instance of R$^{E1}$ is —CH$_2$OR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of R$^{E1}$ is —CH$_2$N(R$^{EF}$)$_2$ or N(R$^{EF}$)$_2$, wherein each instance of R$^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two R$^{EF}$ groups are joined to form an optionally substituted heterocyclic ring. In certain embodiments, at least one instance of R$^{E1}$ is —CH$_2$SR$^{EE}$ or —SR$^{EE}$ (e.g., —CH$_2$SMe or —SMe). In certain embodiments, at least one instance of R$^{E1}$ is —OR$^{EE}$ (e.g., —OMe). In certain embodiments, at least one instance of R$^{E1}$ is —Si(R$^{EG}$)$_3$, wherein each instance of R$^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$).

In certain embodiments, at least one instance of $R^{E2}$ is H. In certain embodiments, at least one instance of $R^{E2}$ is halogen (e.g., F, Cl, Br, or I). In certain embodiments, at least one instance of $R^{E2}$ is optionally substituted alkyl (e.g., Me, or Et). In certain embodiments, at least one instance of $R^{E2}$ is optionally substituted alkenyl (e.g., optionally substituted vinyl). In certain embodiments, at least one instance of $R^{E2}$ is optionally substituted alkynyl. In certain embodiments, at least one instance of $R^{E2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E2}$ is substituted or unsubstituted aryl (e.g., substituted or unsubstituted, 6- to 10-membered aryl). In certain embodiments, at least one instance of $R^{E2}$ is substituted or unsubstituted phenyl. In certain embodiments, at least one instance of $R^{E2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E2}$ is —CN. In certain embodiments, at least one instance of $R^{E2}$ is —CH$_2$OR$^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E2}$ is —CH$_2$N(R$^{EF}$)$_2$ or N(R$^{EF}$)$_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E2}$ is —CH$_2$SR$^{EE}$ or —SR$^{EE}$ (e.g., —CH$_2$SMe or —SMe). In certain embodiments, at least one instance of $R^{E2}$ is —OR$^{EE}$ (e.g., —OMe). In certain embodiments, at least one instance of $R^{E2}$ is —Si(R$^{EG}$)$_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$). In certain embodiments, at least one instance of $R^{E3}$ is H. In certain embodiments, at least one instance of $R^{E3}$ is halogen (e.g., F, Cl, Br, or I). In certain embodiments, at least one instance of $R^{E3}$ is optionally substituted alkyl (e.g., Me, or Et). In certain embodiments, at least one instance of $R^{E3}$ is optionally substituted alkenyl (e.g., optionally substituted vinyl). In certain embodiments, at least one instance of $R^{E3}$ is optionally substituted alkynyl. In certain embodiments, at least one instance of $R^{E3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E3}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E3}$ is substituted or unsubstituted aryl (e.g., substituted or unsubstituted, 6- to 10-membered aryl). In certain embodiments, at least one instance of $R^{E3}$ is substituted or unsubstituted phenyl. In certain embodiments, at least one instance of $R^{E3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E3}$ is —CN. In certain embodiments, at least one instance of $R^{E3}$ is —CH$_2$OR$^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E3}$ is —CH$_2$N(R$^{EF}$)$_2$ or N(R$^{EF}$)$_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E3}$ is —CH$_2$SR$^{EE}$ or —SR$^{EE}$ (e.g., —CH$_2$SMe or —SMe). In certain embodiments, at least one instance of $R^{E3}$ is —OR$^{EE}$ (e.g., —OMe). In certain embodiments, at least one instance of $R^{E3}$ is —Si(R$^{EG}$)$_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$). In certain embodiments, $R^{E1}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E2}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E2}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E1}$ and $R^{E2}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E2}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E4}$ is a leaving group (e.g., halogen, or a sulfonic acid ester, e.g., —O(tosylate) or —O(mesylate)). In certain embodiments, $R^{E5}$ is halogen (e.g., F, Cl, Br, or I). In certain embodiments, $R^{E6}$ is H. In certain embodiments, $R^{E6}$ is substituted or unsubstituted $C_{1-6}$ alkyl (e.g., Me, is —$CF_3$, Bn, Et, perfluoroethyl, Pr, perfluoropropyl, Bu, or perfluorobutyl). In certain embodiments, $R^{E6}$ is a nitrogen protecting group (e.g., Bn, Boc, Cbz, Fmoc, trifluoroacetyl, triphenylmethyl, acetyl, or Ts). In certain embodiments, at least one instance of Y is O. In certain embodiments, at least one instance of Y is S. In certain embodiments, at least one instance of Y is $NR^{E7}$, wherein $R^{E7}$ is hydrogen, substituted or unsubstituted $C_{1-6}$ alkyl, or a nitrogen protecting group (e.g., NMe). In certain embodiments, a is 1. In certain embodiments, a is 2. In certain embodiments, at least one instance of z is 0. In certain embodiments, at least one instance of z is 1. In certain embodiments, at least one instance of z is 2. In certain embodiments, at least one instance of z is 3. In certain embodiments, at least one instance of z is 4. In certain embodiments, at least one instance of z is 5. In certain embodiments, at least one instance of z is 6.

In certain embodiments, the compound of Formula (I') is of formula:

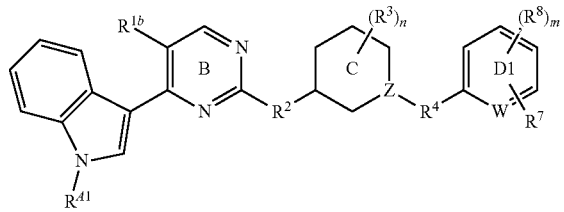

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

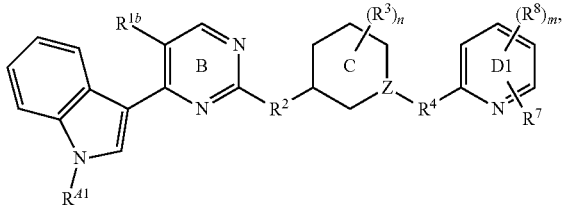

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

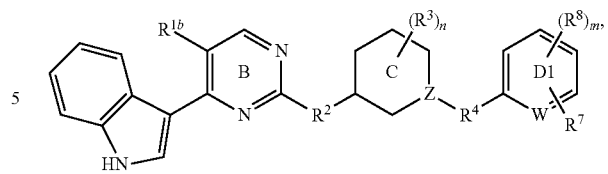

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

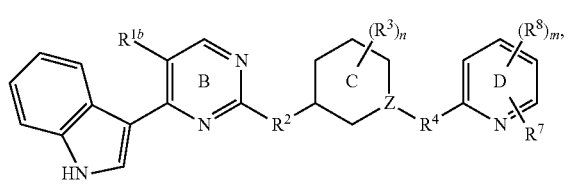

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

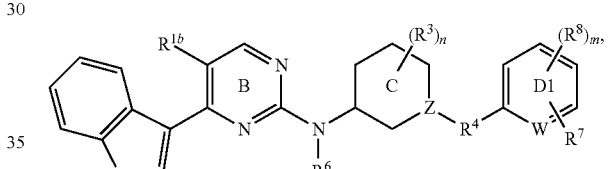

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

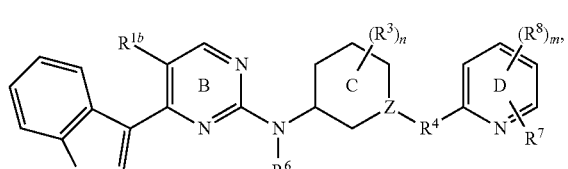

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

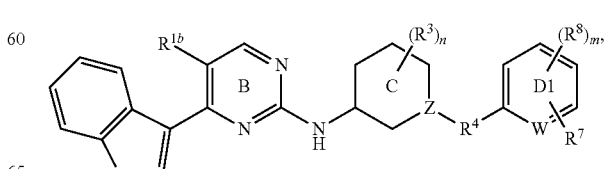

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

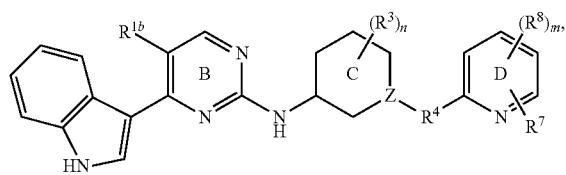

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

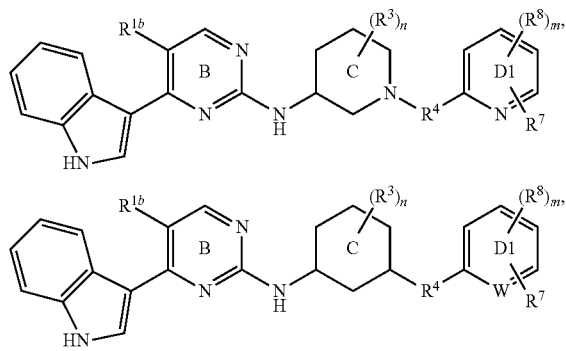

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

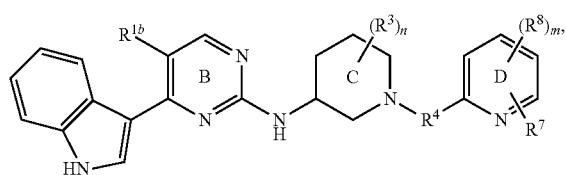

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

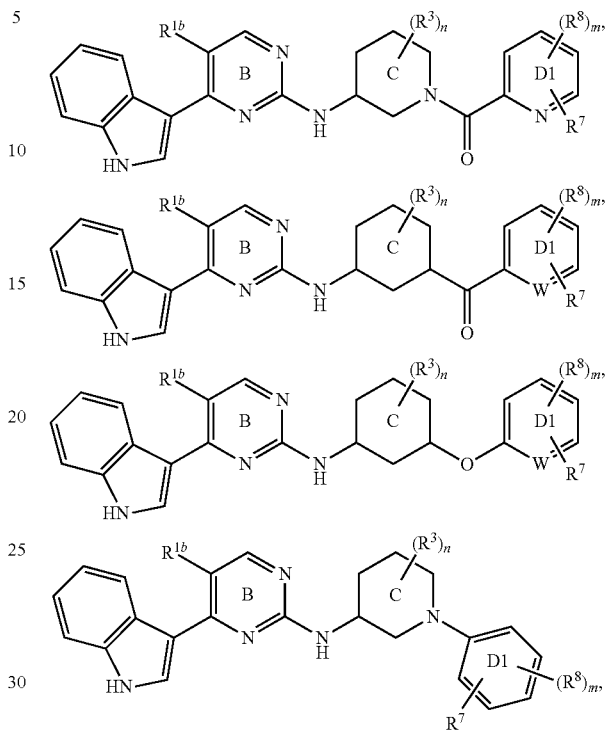

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

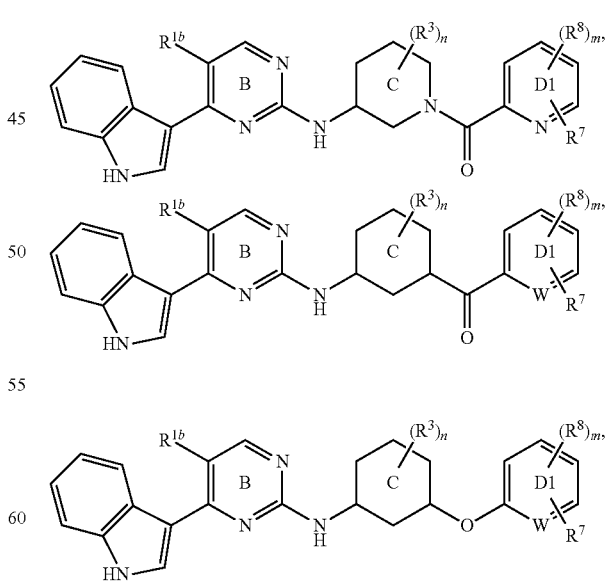

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

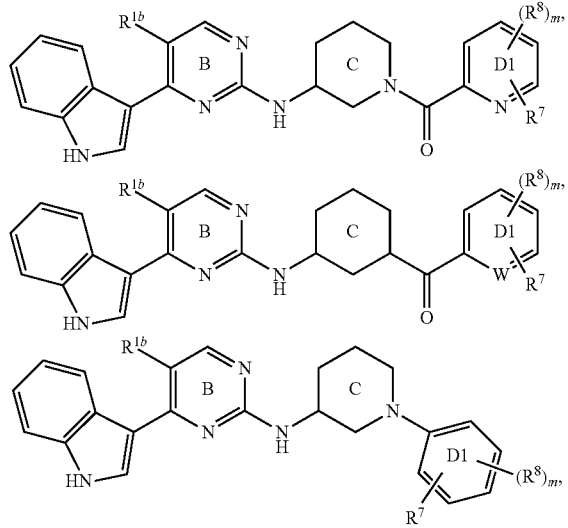

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

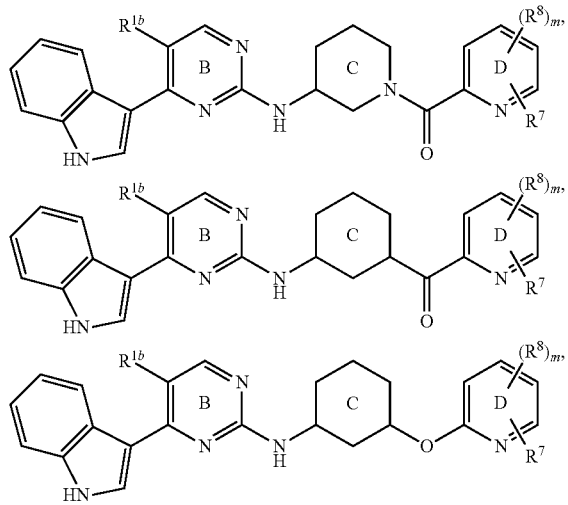

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

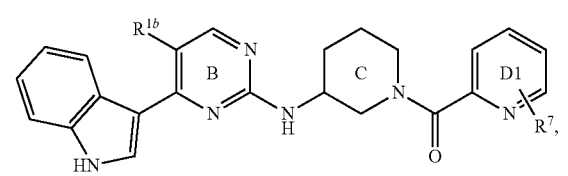

-continued

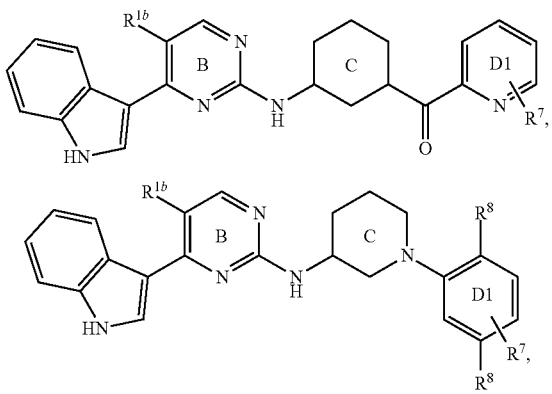

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

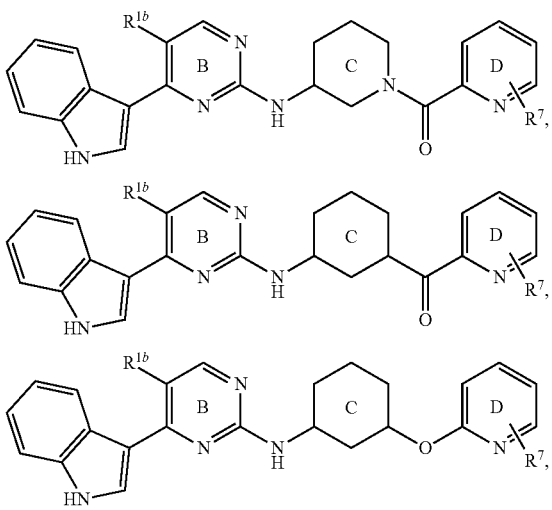

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

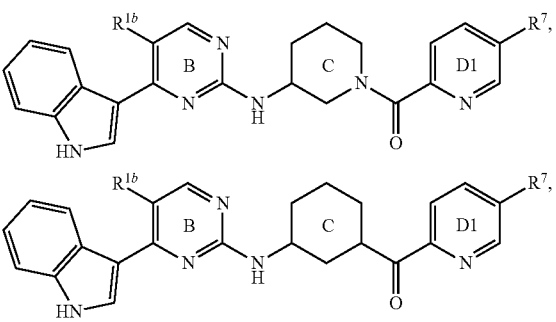

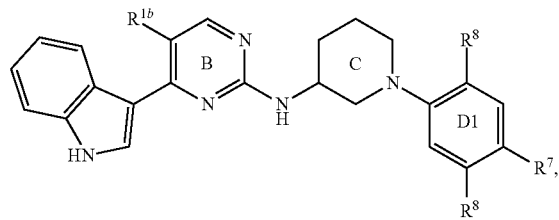

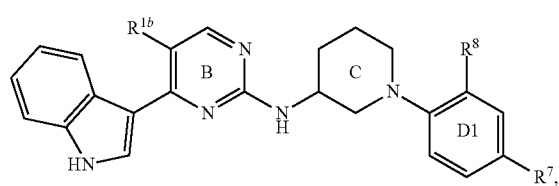

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

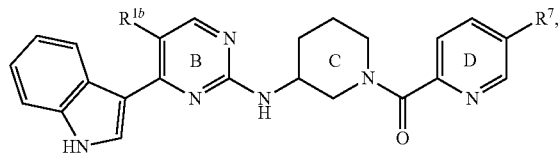

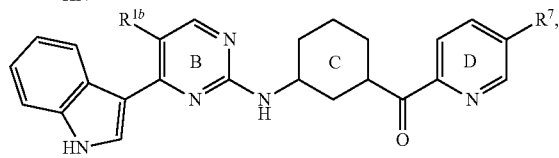

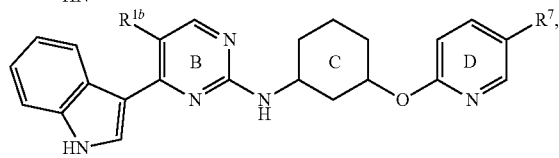

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

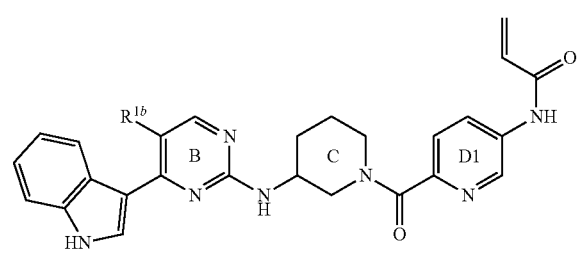

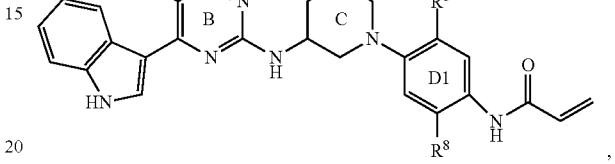

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

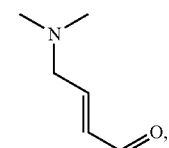

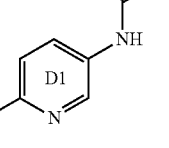

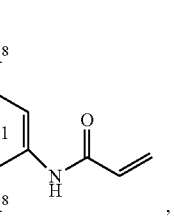

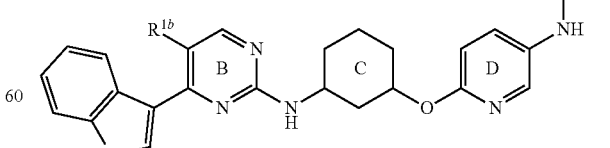

or a pharmaceutically acceptable salt, solvate, hydrate, polymorph, co-crystal, tautomer, stereoisomer, isotopically labeled derivative, or prodrug thereof.

Exemplary compounds of Formula (I') include, but are not limited to:

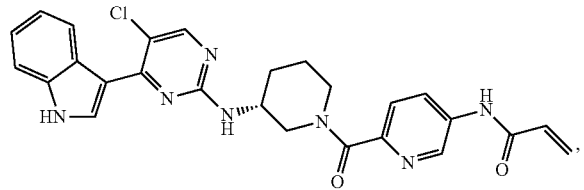

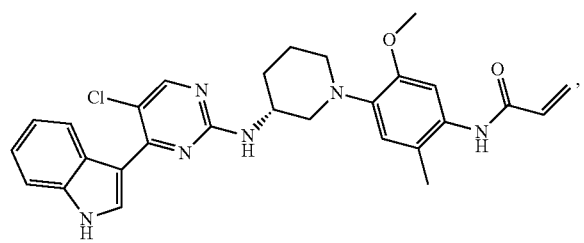

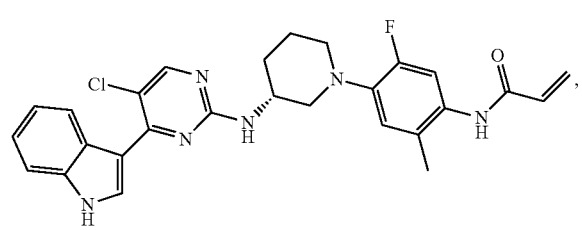 [SMILES: C=CC(=O)Nc1ccc(N2CCC[C@@H](Nc3ncc(Cl)c(-c4c[nH]c5ccccc45)n3)C2)c(F)c1]

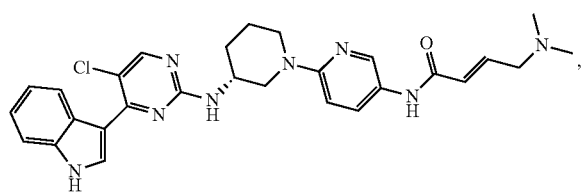

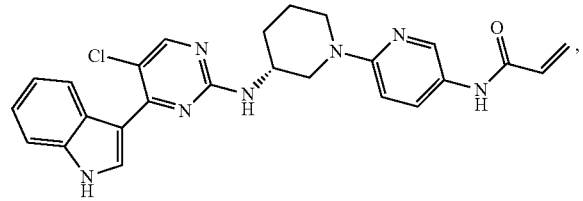

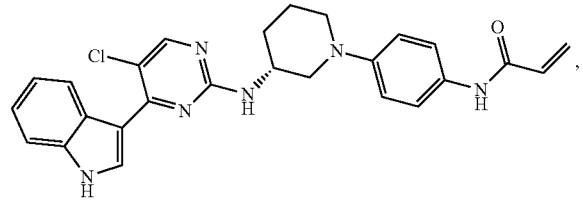

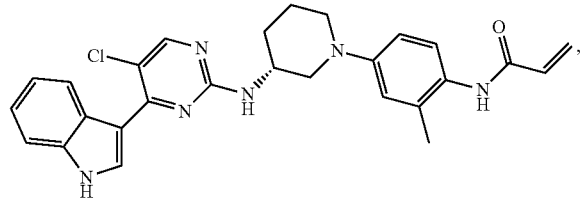

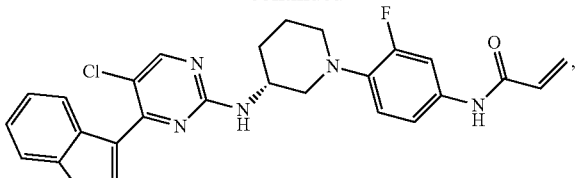

and pharmaceutically acceptable salts, solvates, hydrates, polymorphs, co-crystals, tautomers, stereoisomers, isotopically labeled derivatives, and prodrugs thereof.

Exemplary compounds of Formula (I) include, but are not limited to:

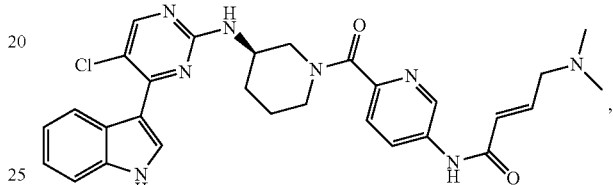

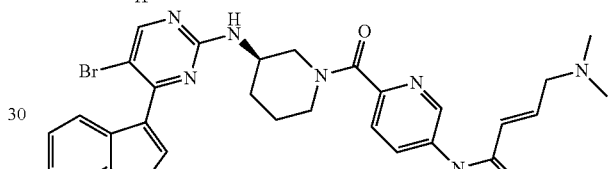

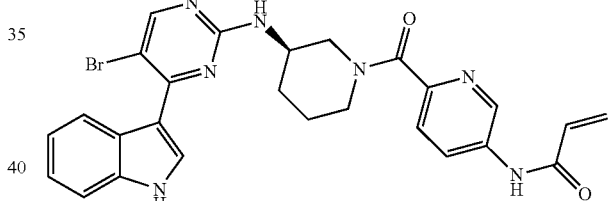

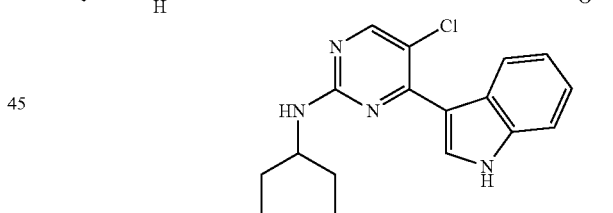

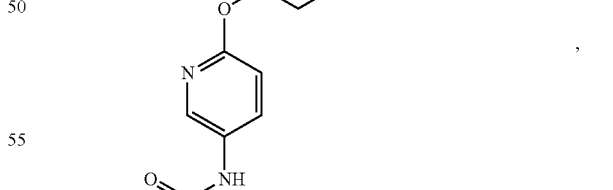

and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (II):

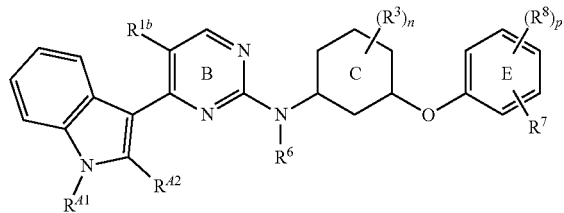

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

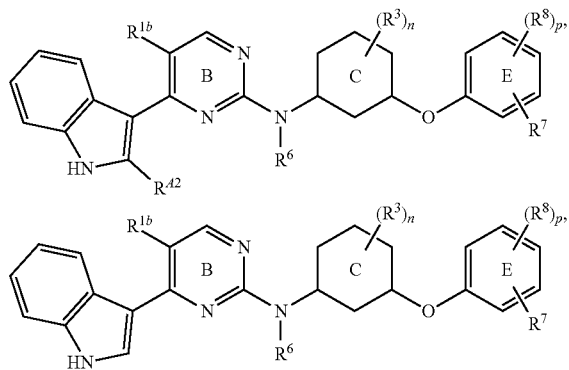

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

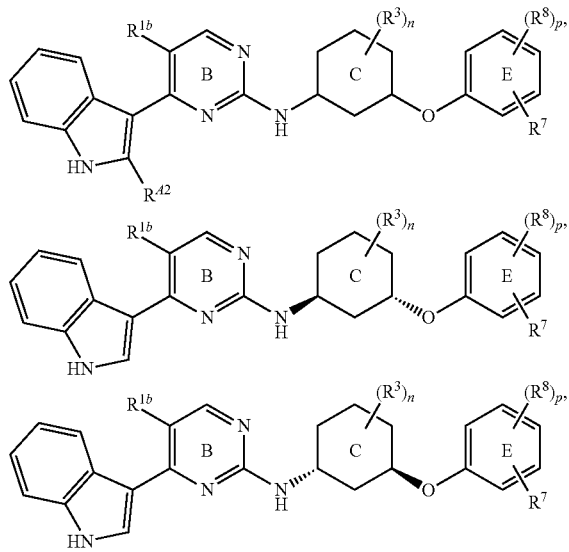

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

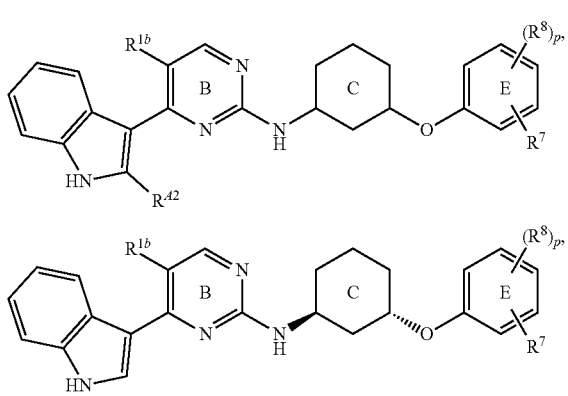

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

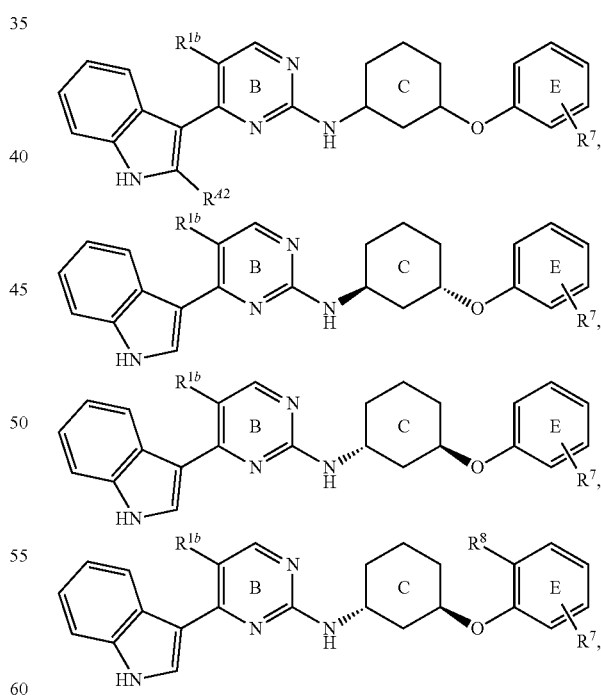

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

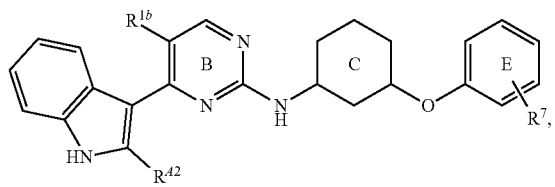

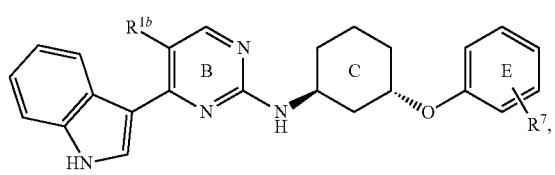

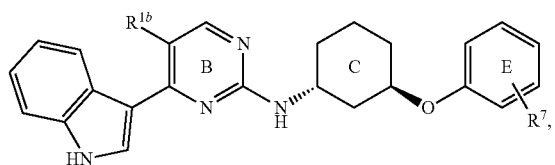

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

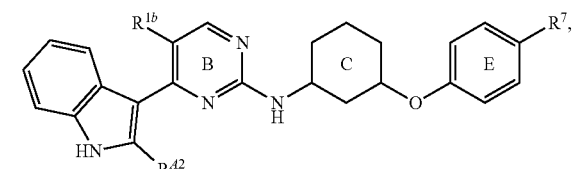

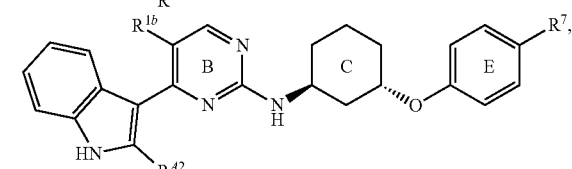

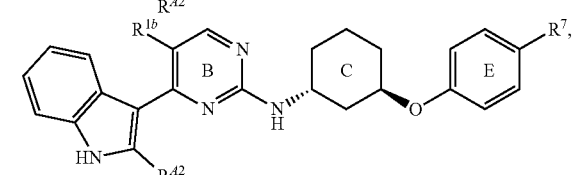

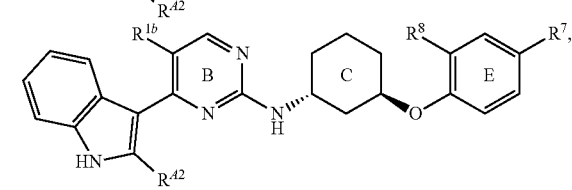

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

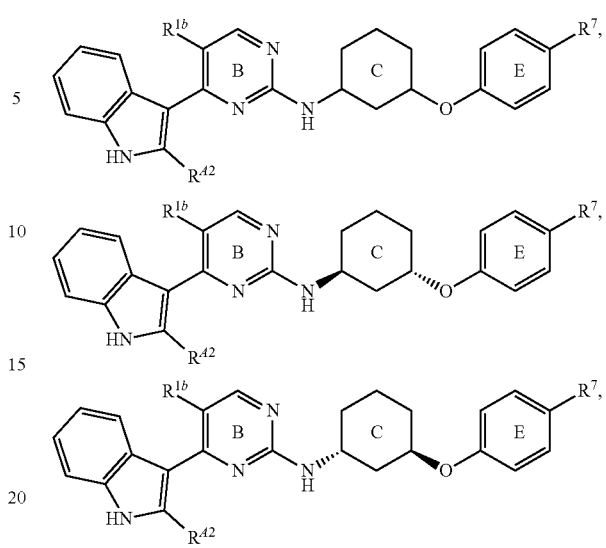

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

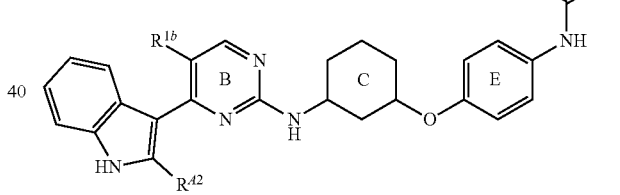

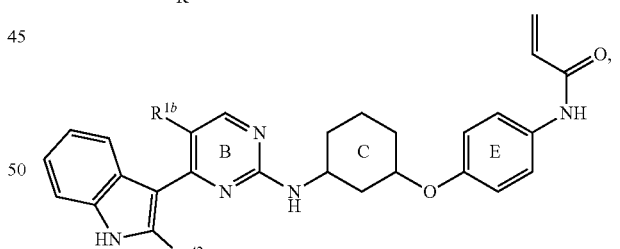

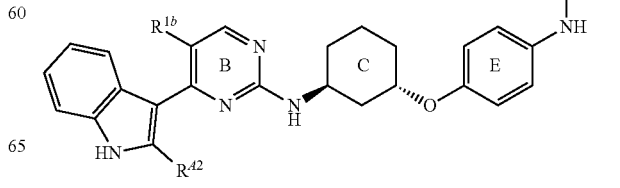

125
-continued
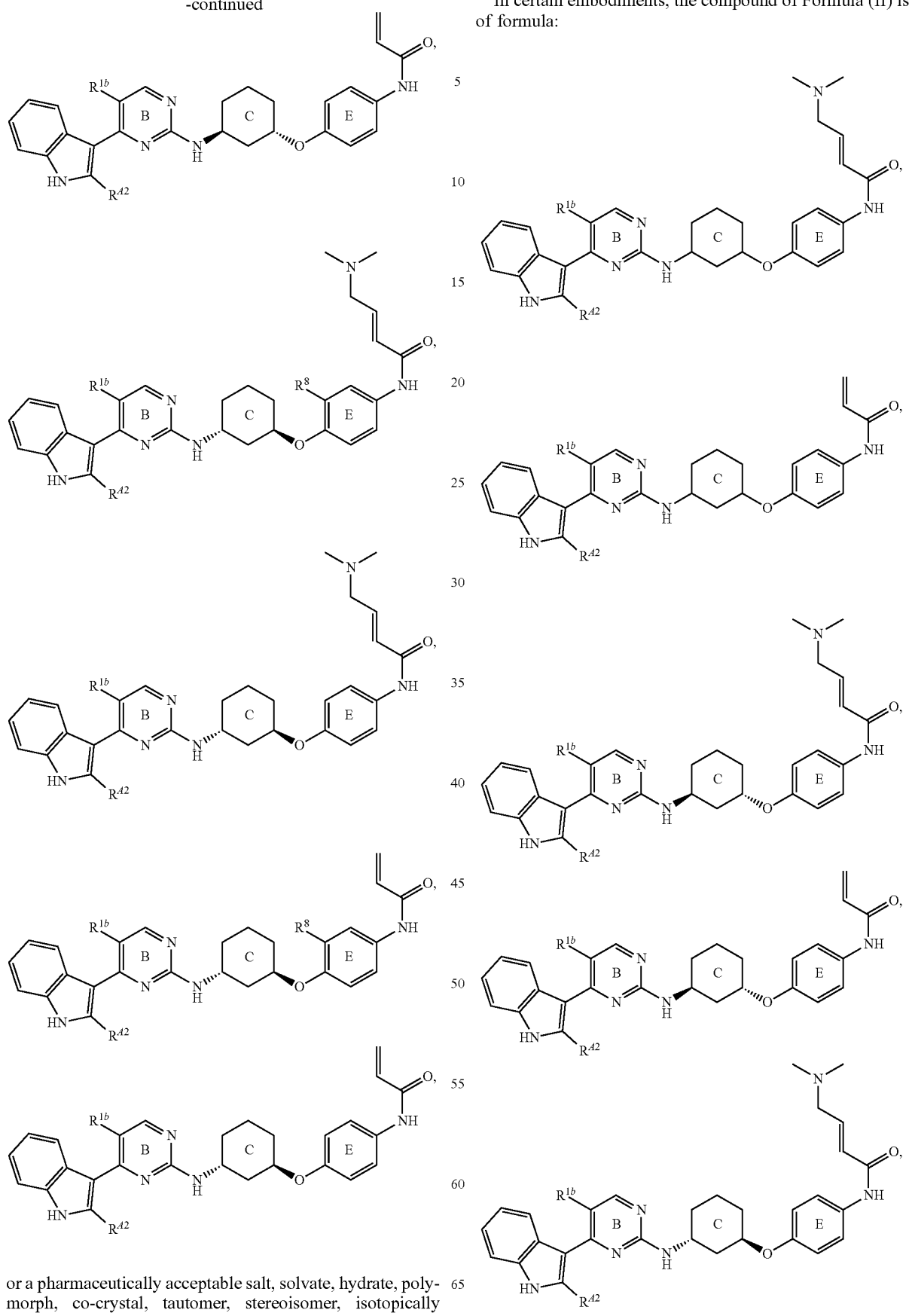
or a pharmaceutically acceptable salt, solvate, hydrate, polymorph, co-crystal, tautomer, stereoisomer, isotopically labeled derivative, or prodrug thereof.
126
In certain embodiments, the compound of Formula (II) is of formula:

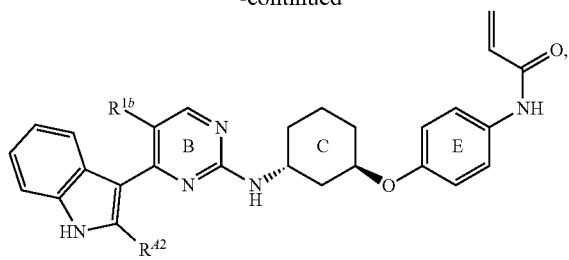

or a pharmaceutically acceptable salt, solvate, hydrate, polymorph, co-crystal, tautomer, stereoisomer, isotopically labeled derivative, or prodrug thereof.

Exemplary compounds of Formula (II) include, but are not limited to:

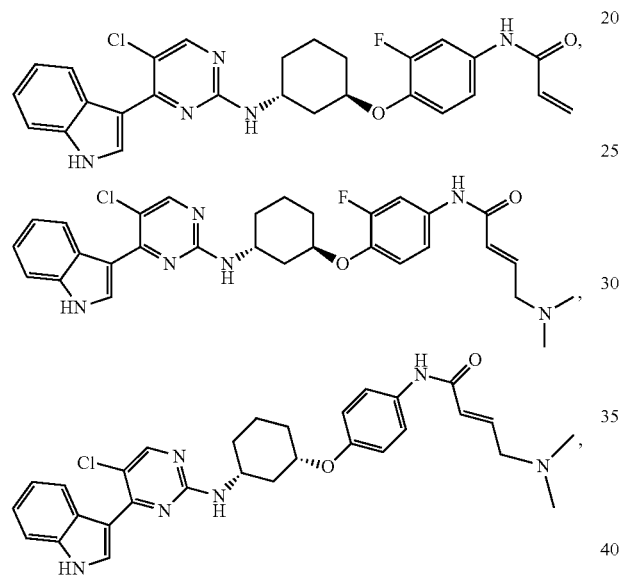

and pharmaceutically acceptable salts, solvates, hydrates, polymorphs, co-crystals, tautomers, stereoisomers, isotopically labeled derivatives, and prodrugs thereof.

Exemplary compounds of Formula (II) include, but are not limited to:

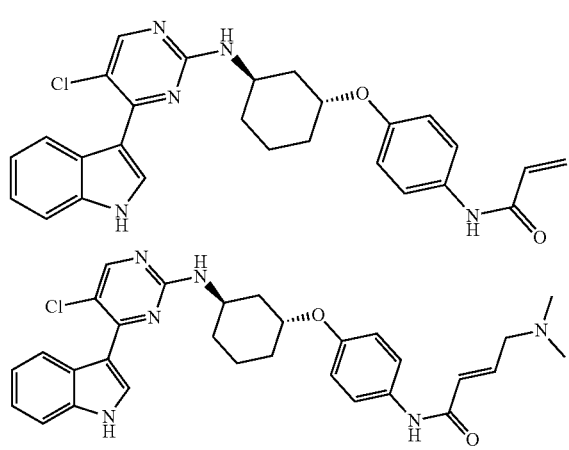

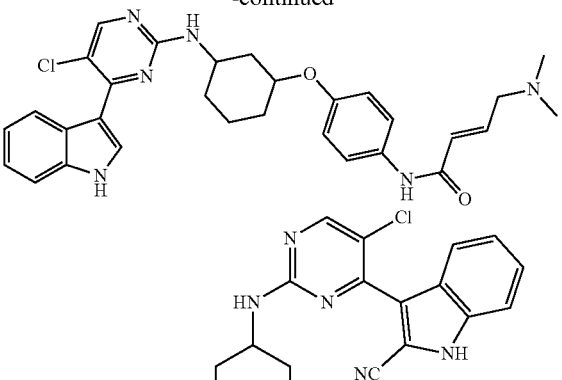

and pharmaceutically acceptable salts, solvates, hydrates, polymorphs, co-crystals, tautomers, stereoisomers, isotopically labeled derivatives, and prodrugs thereof.

Pharmaceutical Compositions, Kits, and Administration

The present disclosure also provides pharmaceutical compositions comprising a compound described herein and optionally a pharmaceutically acceptable excipient. In certain embodiments, a compound described herein is a compound of Formula (I') or (II), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the activity of a CDK (e.g., CDK12). In certain embodiments, a therapeutically effective amount is an amount effective for treating a disease (e.g., a disease associated with aberrant activity of a CDK (e.g., proliferative disease)). In certain embodiments, a therapeutically effective amount is an amount effective for inhibiting the activity of a CDK (e.g., CDK12) and treating a disease (e.g., a disease associated with aberrant activity of a CDK (e.g., proliferative disease)). In certain embodiments, a therapeutically effective amount is an amount effective for inducing apoptosis in a cell. In certain embodiments, a therapeutically effective amount is an amount effective for affecting cell cycle control. In certain embodiments, a therapeutically effective amount is an amount effective for affecting DNA repair or DNA damage response. In certain embodiments, a prophylactically effective amount is an amount effective for inhibiting the activity of a CDK (e.g., CDK12). In certain embodiments, a prophylactically effective amount is an amount effective for preventing or keeping a subject in need thereof in remission of a disease (e.g., a disease associated with aberrant activity of a CDK (e.g., proliferative disease)). In certain embodiments, a prophylactically effective amount is an amount effective for inhibiting the activity of a CDK (e.g., CDK12, or a mutant form of CDK12), and preventing or keeping a subject in need thereof in remission of a disease (e.g., a disease associated with the activity of a CDK (e.g., proliferative disease)). In certain embodiments, a prophylactically effective amount is an amount effective for inducing apoptosis in a cell.

In certain embodiments, the effective amount is an amount effective for inhibiting the activity of a CDK (e.g., CDK12) by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of a CDK (e.g., CDK12) by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell being contacted with a compound or composition described herein is in vitro. In certain embodiments, the cell being contacted with a compound or composition described herein is in vivo.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip©, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of a protein kinase (e.g., CDK) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, genetic disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a binder or inhibitor of a CDK (e.g., CDK12). In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of a protein kinase (e.g., CDK) in a subject, biological sample, tissue, or cell. In certain embodiments, the kits are useful for inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for modulating (e.g., inhibiting) the activity (e.g., aberrant activity, such as increased activity) of a CDK in a subject, biological sample, tissue, or cell. In certain embodiments, the kits and instructions provide for inducing apoptosis in a cell. A kit described herein may include one or more additional pharmaceutical agents described herein as a separate composition.

Methods of Treatment and Uses

The present disclosure provides methods of modulating (e.g., inhibiting or increasing) the activity (e.g., aberrant activity, such as increased or decreased activity) of a protein kinase (e.g., CDK). The present disclosure provides methods of modulating (e.g., inhibiting or increasing) the activity (e.g., aberrant activity, such as unwanted activity, increased activity, activity above normal levels, or decreased activity) of a CDK (e.g., CDK12) in a subject or cell. In certain embodiments, the CDK is a mutant form of CDK12. The present disclosure also provides methods for the treatment of a wide range of diseases, such as diseases associated with aberrant activity (e.g., increased activity) of a protein kinase, e.g., proliferative diseases, musculoskeletal diseases, genetic diseases, hematological diseases, neurological diseases, painful conditions, psychiatric disorders, metabolic disorders, benign neoplasms, diseases associated with angiogenesis, inflammatory diseases, autoinflammatory diseases, and autoimmune diseases in a subject in need thereof. The present invention provides methods for the treatment or prevention of a proliferative disease (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject.

In another aspect, the present disclosure provides methods of modulating the activity of a protein kinase (e.g., CDK, (e.g., CDK12)) in a subject or cell. In certain embodiments, provided are methods of inhibiting the activity of a protein kinase in a subject. In certain embodiments, the kinase is a mutant form of CDK12. In certain embodiments, provided are methods of inhibiting the activity of a protein kinase in a cell. In certain embodiments, provided are methods of increasing the activity of a protein kinase (e.g., CDK, (e.g., CDK12)) in a subject. The compounds described herein may exhibit kinase inhibitory activity; the ability to inhibit cyclin-dependent kinase (CDK); the ability to inhibit cyclin-dependent kinase 12 (CDK12); the ability to inhibit cyclin-dependent kinase 12 (CDK12), without inhibiting another cyclin-dependent kinase (CDK); a therapeutic effect and/or preventative effect in the treatment of cancers; a therapeutic effect and/or preventative effect in the treatment of Myc-dependent cancers; and/or a therapeutic profile (e.g., optimum safety and curative effect) that is superior to existing chemotherapeutic agents. In certain embodiments, provided are methods of inhibiting CDK12, without inhibiting another cyclin-dependent kinase (CDK7). In certain embodiments, provided are methods of inhibiting a mutant form of cyclin-dependent kinase 12 (CDK12), without inhibiting another cyclin-dependent kinase (CDK).

In certain embodiments, provided are methods of decreasing the activity of a protein kinase (e.g., CDK, (e.g., CDK12)) in a subject or cell described herein by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a protein kinase (e.g., CDK, (e.g., CDK12)) in a subject or cell is decreased by a method described herein by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of a protein kinase (e.g., CDK, (e.g., CDK12)) in a subject or cell is selectively inhibited by the method. In some embodiments, the activity of a protein kinase (e.g., CDK, (e.g., CDK12)) in a subject or cell is selectively decreased by the method.

Without wishing to be bound by any particular theory, in certain embodiments the compounds described herein are able to bind (e.g., covalently modify) the protein kinase being inhibited. In certain embodiments, a compound described herein is able to bind (e.g., covalently modify) to the protein kinase. In certain embodiments, the compound described herein is able to covalently bind a cysteine residue of the protein kinase. In certain embodiments, the compound described herein is able to covalently bind residue Cys1039 of CDK12, without covalently binding other kinases. In certain embodiments, the compound described herein is able to covalently bind residue Cys1039 of CDK12, without covalently binding Cys312 of CDK7. In certain embodiments, the compound described herein is able to covalently bind residue Cys1039 of CDK12, without covalently binding other residues of CDK12. In certain embodiments, the compound is capable of covalently modifying CDK12 (e.g., Cys1039 of CDK12). In certain embodiments, the compound described herein is able to covalently modify residue Cys1039 of CDK12. In certain embodiments, the compound described herein is able to covalently modify residue Cys1039 of CDK12, without covalently modifying other kinases. In certain embodiments, the compound described herein is able to covalently modify residue Cys1039 of CDK12, without covalently modifying Cys312 of CDK7. In certain embodiments, the compound described herein is able to covalently modify residue Cys1039 of CDK12, without covalently modifying other residues of CDK12.

In another aspect, the present disclosure provides methods of inhibiting the activity of a protein kinase in a subject, the methods comprising administering to the subject an effective amount (e.g., therapeutically effective amount) of a compound, or pharmaceutical composition thereof, as described herein. In another aspect, the present disclosure provides methods of inhibiting the activity of a protein kinase in a biological sample, the methods comprising contacting the biological sample with an effective amount of a compound, or pharmaceutical composition thereof, as described herein. In another aspect, the present disclosure provides methods of inhibiting the activity of a protein kinase in a tissue, the methods comprising contacting the tissue with an effective amount of a compound, or pharmaceutical composition thereof, as described herein.

In another aspect, the present disclosure provides methods of inhibiting the activity of a protein kinase in a cell, the methods comprising contacting the cell with an effective amount of a compound, or pharmaceutical composition thereof, as described herein.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the biological sample being contacted with the compound or composition is breast tissue, bone marrow, lymph node, lymph tissue, spleen, or blood.

In certain embodiments, the cell being contacted with the compound or composition is present in vitro. In certain embodiments, the cell being contacted with the compound or composition is present in vivo. In certain embodiments, the cell being contacted with the compound or composition is present ex vivo. In certain embodiments, the cell being contacted with the compound or composition is a malignant cell (e.g., malignant blood cell). In certain embodiments, the cell being contacted with the compound or composition is a malignant hematopoietic stem cell (e.g., malignant myeloid cell or malignant lymphoid cell). In certain embodiments, the cell being contacted with the compound or composition is a malignant lymphocyte (e.g., malignant T-cell or malignant B-cell). In certain embodiments, the cell being contacted with the compound or composition is a malignant red blood cell, malignant white blood cell, or malignant platelet. In certain embodiments, the cell being contacted with the compound or composition is a malignant neutrophil, malignant macrophage, or malignant plasma cell. In certain embodiments, the cell being contacted with the compound or composition is a carcinoma cell. In certain embodiments, the cell being contacted with the compound or composition is a carcinoma breast cell. In certain embodiments, the cell being contacted with the compound or composition is a sarcoma cell. In certain embodiments, the cell being contacted with the compound or composition is a sarcoma cell from breast tissue.

The proliferative disease to be treated or prevented using the compounds described herein may be associated with overexpression of a kinase, such as cyclin-dependent kinase (CDK). The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are CDC2 (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins.

Modulation of the expression levels, degradation rates, protein levels, and activity levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the prerequisite biochemical criteria at a given cell cycle checkpoint, e.g., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

In certain embodiments, the proliferative disease to be treated or prevented using the compounds described herein may be associated with overexpression of a CDK (e.g., CDK12).

CDK12 and CDK13 are Cdc2-related proteins that share 92% identity in their kinase domains (Chen et al., *Exp. Neurol.*, 2014, 261, 10-21). CDK12 plays a critical role in cell processes, for example, regulating transcription and splicing machinery by stabilizing the RNAPII and DNA interaction, and regulating DNA damage response (DDR) and maintenance of genomic stability by modulating the expression of DDR genes. Overexpression of CDK12 has been found to correlate, both at the transcriptional and protein level, with pathological parameters of breast cancer disease.

A proliferative disease may be associated with aberrant activity of a CDK (e.g., CDK12). Aberrant activity of a CDK (e.g., CDK12) may be an elevated and/or an inappropriate activity of the CDK. Deregulation of cell cycle progression is a characteristic of a proliferative disease, and a majority of proliferative diseases have abnormalities in some component of CDK (e.g., CDK12) activity, frequently through elevated and/or inappropriate CDK activation. Inhibition of the catalytic activity of CDK12 would be expected to inhibit cell cycle progression by blocking the phosphorylation of cell cycle CDKs, and would additionally inhibit transcription of effectors of cell division. In certain embodiments, CDK12 is not overexpressed, but the activity of CDK12 is elevated and/or inappropriate. In certain embodiments, CDK12 is overexpressed, and the activity of CDK12 is elevated and/or inappropriate. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of CDK7 and be useful in treating and/or preventing proliferative diseases. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of CDK12 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Apoptosis is the process of programmed cell death. Inhibition of apoptosis may result in uncontrolled cell proliferation and, therefore, may cause proliferative diseases. The CycK/Cdk12 complex regulates phosphorylation of Ser2 in the C-terminal domain of RNA polymerase II and expression of a small subset of human genes, as revealed in expression microarrays. Through regulation of expression of DNA damage response genes (i.e. oncogenes), CycK/Cdk12 protects cells from genomic instability. In certain embodiments, the DNA damage response genes regulated by CDK12 are BRCA1, BRCA2, HER1, HER2, ATR, FANCI, or FANCD2. In certain embodiments, the DNA damage response genes regulated by CDK12 are BRCA1, HER2, ATR, FANCI, and FANCD2. In certain embodiments, the DNA damage response gene regulated by CDK12 is BRCA1. In certain embodiments, the DNA damage response gene regulated by CDK12 is HER2. In certain embodiments, the DNA damage response genes are down-regulated by CDK12.

In certain embodiments, the proliferative disease to be treated or prevented using the compounds described herein is cancer. All types of cancers disclosed herein or known in the art are contemplated as being within the scope of the invention. In certain embodiments, the proliferative disease is a cancer associated with BCL-2 anti-apoptotic proteins (e.g., MCL-1 and/or XIAP) (e.g., cancer associated with dependence on BCL-2 anti-apoptotic proteins). In certain embodiments, the proliferative disease is a cancer associated with overexpression of MYC (a gene that codes for a transcription factor). In certain embodiments, the cancer is a MYC-dependent cancer. In certain embodiments, the proliferative disease is a cancer associated with the amplification of BRCA1. In certain embodiments, the proliferative disease is a cancer associated with the amplification of HER2. In certain embodiments, the proliferative disease is a hematological malignancy. In certain embodiments, the proliferative disease is a blood cancer. In certain embodiments, the proliferative disease is a hematological malignancy. In certain embodiments, the proliferative disease is a leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is colorectal cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2– breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis.

In certain embodiments, the proliferative disease is an acute inflammatory disease. In certain embodiments, the acute inflammatory disease is rheumatoid arthritis, Crohn's disease, or fibrosis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

Another aspect of the invention relates to methods of inhibiting the activity of a kinase in a biological sample, tissue, cell, or subject. In certain embodiments, the kinase is a CDK. In certain embodiments, the kinase is CDK12. In certain embodiments, the kinase is a mutant form of CDK12. In certain embodiments, the activity of the kinase is aberrant or undesired activity of the kinase. In certain embodiments, the activity of the kinase is increased activity of the kinase. In certain embodiments, the inhibition of the activity of the kinase is irreversible. In other embodiments, the inhibition of the activity of the kinase is reversible. In certain embodiments, the methods of inhibiting the activity of the kinase include covalently attaching a compound described herein to the kinase.

Also provided in the present invention are methods of inhibiting transcription of genes in a biological sample or subject. In certain embodiments, the transcription of genes regulated by the activity of CDK12 may be inhibited by a compound of the invention. In certain embodiments, the transcription of genes regulated by the activity of CDK12 may be inhibited by a compound of the invention. In certain embodiments, the genes which may have their transcription inhibited by the activity of CDK12 are one or more genes selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, and EWS-FLI. In certain embodiments, administering a compound described herein to a subject in need thereof will up-regulate one or more genes selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, and EWS-FLI. The present invention also provides methods of up-regulating one or more genes selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, and EWS-FLI, the method comprising administering to a subject in need thereof a compound described herein. The present invention also provides uses of the compounds described herein, for up-regulating one or more genes selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, and EWS-FLI, comprising administering to a subject in need thereof the compound described herein.

The present invention also provides methods of inhibiting cell growth in a biological sample, tissue, cell, or subject.

In still another aspect, the present invention provides methods of inducing apoptosis of a cell in a biological sample, tissue, cell, or subject.

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of a CDK. In certain embodiments, the additional pharmaceutical agent is an inhibitor of CDK12. In certain embodiments, the additional pharmaceutical agent is a selective inhibitor of CDK12. In certain embodiments, the additional pharmaceutical agent is a nonselective inhibitor of CDK12. In certain embodiments, the additional pharmaceutical agent is an inhibitor of another CDK. In certain embodiments, the additional pharmaceutical agent is a selective inhibitor of another CDK. In certain embodiments, the additional pharmaceutical agent is a nonselective inhibitor of another CDK. In certain embodiments, the additional pharmaceutical agent is flavopiridol, triptolide, SNS-032 (BMS-387032), PHA-767491, PHA-793887, BS-181, (S)-CR8, (R)-CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a calmodulin-dependent kinase (CaM Kinase). In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase.

In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In some embodiments, the additional pharmaceutical agent is etoposide, obatoclax, or navitoclax, and the disease to be treated is breast cancer, e.g., triple-negative breast cancer, HER2 positive breast cancer, HER2 negative breast cancer, ER-positive breast cancer, ER-negative breast cancer, or ER/PR-positive breast cancer. In some embodiments, the additional pharmaceutical agent is etoposide, JIB04, or cisplatin, and the disease to be treated is Ewing's sarcoma. In some embodiments, the additional pharmaceutical agent is JQ1 or NVP2, and the disease to be treated is leukemia, e.g., acute myelogenous leukemia, myeloblastic leukemia, promyelocytic leukemia, myelomonocytic leukemia, monocytic leukemia, monoblastic leukemia, or megakaryoblastic leukemia. In certain embodiments, a pharmaceutical composition described herein further comprises a combination of the additional pharmaceutical agents described herein.

The inventive compounds or compositions may synergistically augment inhibition of CDK12 induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In some embodiments, the activity of a protein kinase is non-selectively inhibited by the compounds or pharmaceutical compositions described herein. In some embodiments, the activity of the protein kinase being inhibited is selectively inhibited by the compounds or pharmaceutical compositions described herein, compared to the activity of a different protein (e.g., a different protein kinase). In certain embodiments, the activity of CDK (e.g., CDK12) is selectively inhibited by a compound or pharmaceutical composition described herein, compared to the activity of a different protein. In certain embodiments, the activity of CDK12 is selectively inhibited by a compound or pharmaceutical composition described herein, compared to the activity of another CDK (e.g., CDK7 or CDK13).

The selectivity of a compound or pharmaceutical composition described herein in inhibiting the activity of a protein kinase over a different protein (e.g., a different protein kinase) may be measured by the quotient of the $IC_{50}$ value of the compound or pharmaceutical composition in inhibiting the activity of the different protein over the $IC_{50}$ value of the compound or pharmaceutical composition in inhibiting the activity of the protein kinase. The selectivity of a compound or pharmaceutical composition described herein for a protein kinase over a different protein may also be measured by the quotient of the $K_d$ value of an adduct of the compound or pharmaceutical composition and the different protein over the $K_d$ value of an adduct of the compound or pharmaceutical composition and the protein kinase. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

In certain embodiments, a kit described herein includes a first container comprising a compound or pharmaceutical composition described herein. In certain embodiments, a kit described herein is useful in treating a proliferative disease (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject in need thereof, preventing a proliferative disease in a subject in need thereof, inhibiting the activity of a protein kinase (e.g., CDK (e.g., CDK12)) in a subject, biological sample, tissue, or cell, and/or inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, preventing a proliferative disease in a subject in need thereof, inhibiting the activity of a protein kinase (e.g., CDK (e.g., CDK12)) in a subject, biological sample, tissue, or cell, and/or inducing apoptosis in a cell. A kit described herein may include one or more additional pharmaceutical agents described herein as a separate composition.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Structure-Activity Analyses for Selected Compounds

Select compounds described herein were evaluated for structure-activity analyses. Exemplary results of the $IC_{50}$ values of exemplary compound BSJ-01-175-1 on other CDK kinases from an Invitrogen biochemical assay are shown in Table 1. In vitro kinase assays were performed by Life Technologies in duplicate at an ATP concentration=$K_m$ for each kinase. The $IC_{50}$ on Jurkat cell is from an anti-proliferaction assay; $IC_{50}$ on CDK2, CDK7 and CDK9 is from a biochemical kinase inhibition assay from Life technology. See Table 1A and Table 1.

TABLE 1A

IC$_{50}$ values of exemplary compounds described herein.

| ID | IC$_{50}$ (nM) Jurkat Cell | CDK2/ Cyclin A | IC$_{50}$ (nM) CDK7/ cyclin H/MNAT1 | CDK9/ Cyclin T1 |
|---|---|---|---|---|
| BSJ-01-033 | 139.8 | >10000 | 587 | 585 |
| BSJ-01-175 | 160.6 | 4510 | 121 | 367 |
| BSJ-01-193 | | | | |
| BSJ-01-202 | 54.32 | 3870 | 402 | 658 |
| BSJ-02-057 | | 2040 | 272 | 505 |
| BSJ-02-058 | | 3740 | 251 | 734 |
| BSJ-02-108 | | 492 | 74 | 87.7 |
| BSJ-02-109 | 11.22 | 1940 | 433 | 121 |
| BSJ-02-139 | | 3550 | 162 | 171 |
| BSJ-03-005 | 131.7 | 266 | 118 | 230 |
| BSJ-03-014 | 344 | 3360 | 403 | 522 |
| BSJ-03-055 | | 3390 | 919 | 530 |
| BSJ-03-161 | 62.16 | >10000 | 878 | 786 |
| BSJ-03-162 | 154.3 | 3570 | 269 | 286 |

TABLE 1

IC$_{50}$ values of exemplary compounds described herein.

| Invitrogen Technology: Kinase Tested | Invitrogen Technology: [ATP] Tested (uM) | Invitrogen Technology: IC50 (nM) |
|---|---|---|
| CDK2/cyclin A | Km app | 4510 |
| CDK7/cyclin H/MNAT1 | Km app | 121 |
| CDK9/cyclin T1 | Km app | 367 |

Assay of Anti-Proliferation Activity on Jurkat Cells

Jurkat cells were plated at 30,000 cells/well and treated with a titration of compounds indicated. Cells were allowed to grow for 72 hours. Cells were assayed using CELLTITER GLO (Promega) to determine cell viability by measuring the amount of ATP present, which is an indicator of cell metabolic activity. Results are graphedcalculated as relative as luminescence as compared to DMSOP=.cent values. Curves were generated using PRISM and an IC50 value was determined. See Table 1A.

Assay of Anti-Proliferative Activity for Selected Compounds

Select compounds described herein were evaluated for anti-proliferative activity. Exemplary results of the assay for anti-proliferative activity (in nM) are shown in Table 2. HAP1 WT and CDK12 C1039S/CDK13 C1017S double mutants cells were seeded at a density of 12,000 cells/well in 96-well plates. Twenty-four hours later cells were then treated with compound BSJ-01-175-1 in a 10-pt dose escalation format from 1 nM to 10 μM or DMSO control for 72 hrs. After 72 hrs, cells were assayed using CellTiter-Glo Luminescent Cell Viability Assay (Promega) to determine cell viability by measuring the amount of ATP present in each sample cell population, which is an indicator of cell metabolic activity. Results are graphed as fraction of the DMSO control at 72 hrs. All data points were performed in biological triplicate. HAP1 cells expressing putative inhibitor-refractory mutations in CDK12 (C1039S) and CDK13 (C1017S) are approximately half as sensitive to compound BSJ-01-175-1 as compared to control WT HAP1 cells. This result indicates that a portion of intracellular compound activity comes from covalent inhibition of CDK12 and/or CDK13 and mutation of the targeted cysteines (C1039 in CDK12 and C1017 in CDK13) to less nucleophilic serines is sufficient to rescue some of compound BSJ-01-175-1's anti-proliferative activity. Compound BSJ-1-0175-1 anti-proliferative effects were found to be partially rescued by mutation of critical cysteines in CDK12 and CDK13.

TABLE 2

Assay of Anti-Proliferative Activity for Selected Compounds

| ID | HAP1 (IC$_{50}$, nM) | HAP1 CDK12/13 mutant (IC$_{50}$, nM) |
|---|---|---|
| BSJ-01-175 | 313 | 670 |

Pull-Down Assay for Selected Compounds

Figure 1:
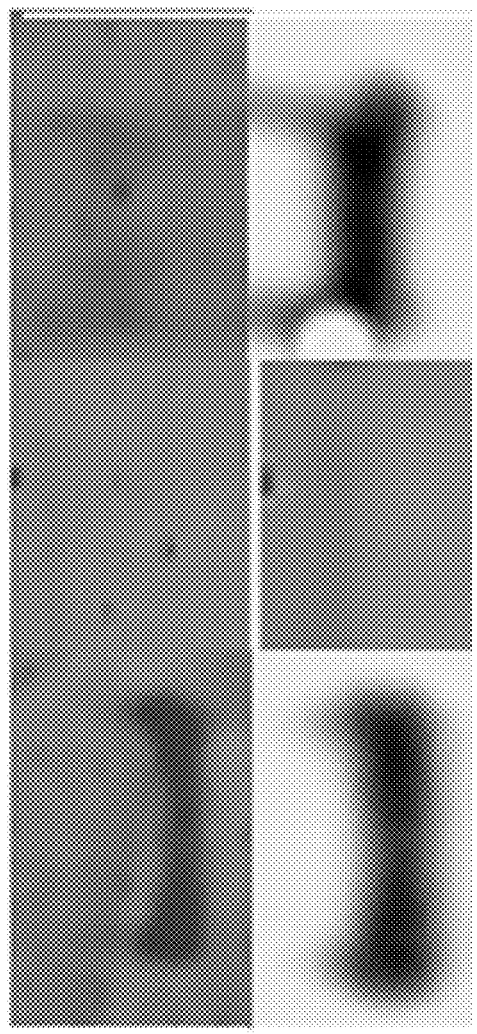
FIG. 1. Cyclin K pull down with THZ1-biotin probe. Exemplary compound BSJ-01-175-1 selectively binds intracellular CDK12/13-cyclin K complexes, and not CDK7-cyclin H complexes.

Jurkat cells were treated with THZ1 (1 μM), compound BSJ-01-175-1 (1 μM), or DMSO vehicle control for 6 hrs. Clarified cellular lysates from each treatment condition were then incubated with either 1 μM THZ1-biotin, a concentration that binds CDK7-cyclin H, CDK12-cyclin K, and CDK13-cyclin K complexes. Lysates were incubated with THZ1-biotin overnight at 4 degrees Celsius. Subsequent addition of streptavidin-coated beads permits the immunoprecipitation of the indicated protein complexes. Following washing of beads with lysis buffer, the immunoprecipitated proteins were eluted from the beads by boiling in SDS buffer. Western blotting for cyclin K was used to identify precipitated CDK12-cyclin K or CDK13-cyclin K complexes. Western blotting for cyclin H was used to identify precipitated CDK7-cyclin H complexes. As THZ1 and compound BSJ-01-175-1 bind to their intended targets covalently, pretreatment of cells with these compounds would be expected to block subsequent capture and immunoprecipitation of these protein complexes with THZ1-biotin. The western blot data indicates that THZ1 binds intracellular CDK12-cyclin K, CDK13-cyclin K and CDK7-cyclin H complexes, while compound BSJ-01-175-1 binds intracellular CDK12-cyclin K and CDK13-cyclin K complexes selectively (and not CDK7-cyclin H). FIG. 1 depicts the results of this pull-down assay of a Cyclin K pull down with THZ1-biotin probe. Indicating that exemplary compound BSJ-01-175-1 selectively binds intracellular CDK12/13-cyclin K complexes, and not CDK7-cyclin H complexes.

In another experiment, Jurkat cells were treated with DMSO or 1.0 μM of the exemplary compounds BSJ-01-033, BSJ-01-175, BSJ-01-202, BSJ-02-139, BSJ-02-109 and BSJ-02-108. 6 hours after treatment, cells were washed and harvested by resuspending in lysis buffer (50 mM Hepes pH 7.4, 150 mM NaCl, 1% NP-40, 5 mM EDTA, protease and phosphatase inhibitors) and lysing on ice for 30 minutes. Lysates were cleared by centrifugation at 15,000 rpm for 30 minutes. Biotin-labeled THZ1 was added to 1 μM to lysates and rotated at 4° C. overnight. Streptavidin-agarose beads were washed and 30 μL slurry was added to each lysate and rotated for 1 hour at 4° C. Beads were washed 5 times with lysis buffer and 50 μL 2xLDS buffer was added to each sample. Samples were boiled and equal volume of protein was loaded onto gel. Gel was transferred to nitrocellulose and blotted for Cyclin K and Cyclin H. FIG. 2 depicts the results of this pull-down assay.

Preparation of the Compounds Described Herein

The compounds provided herein can be prepared from readily available starting materials using the following general methods and procedures. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Example 1. Synthesis of N-(4-((1R,3R)-3-(5-chloro-4-(1H-indol-3-yl)pyrimidin-2-ylamino)cyclohexyloxy)phenyl)acrylamide (BSJ-01-033)

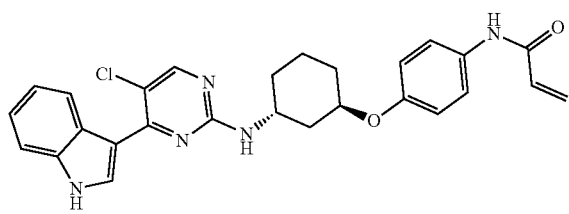 [SMILES: C=CC(=O)Nc1ccc(O[C@@H]2CCC[C@@H](Nc3ncc(Cl)c(-c4c[nH]c5ccccc45)n3)C2)cc1]

(1R,3R)-3-(4-nitrophenoxy)cyclohexanamine

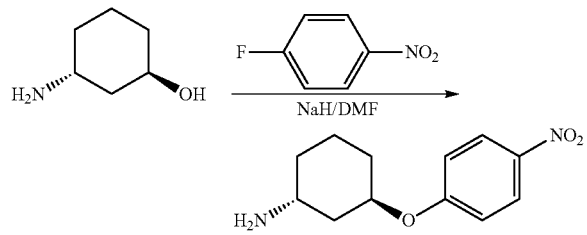

To a suspension of NaH (0.8 g, 8.25 mmol) in 3.0 mL of anhydrous DMF was added (1R,3R)-3-aminocyclohexanol HCl salt (0.5 g, 3.3 mmol) slowly at 0° C. and kept stirring for 0.5 h, then 1-fluoro-4-nitrobenzene (0.465 g, 3.3 mmol) was added. The reaction mixture was kept stirring at 0° C. for another 0.5 h, then warm to room temperature and kept stirring for 2 h. 1.0 mL of H₂O was added dropwise to quench the reaction. The mixture was extracted with DCM (100 mL), washed with brine (3×50 mL), dried (anhydrous Na₂SO₄), filtered and concentrated under reduced pressure. The residue was purified by chromatography on silica gel to give the title compound (623 mg, 80%) as a brown solid. LC-MS (m/z): 237 [M+H]⁺.

5-chloro-N-((1R,3R)-3-(4-nitrophenoxy)cyclohexyl)-4-(1-(phenylsulfonyl)-1H-indol-3-yl)pyrimidin-2-amine

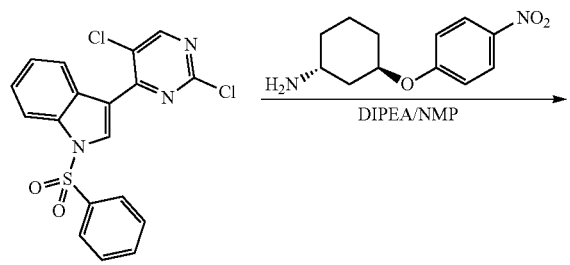

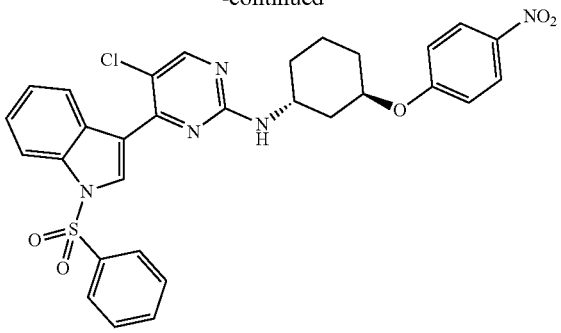

3-(2,5-dichloropyrimidin-4-yl)-1-(phenylsulfonyl)-1H-indole (50 mg, 0.12 mmol) and (1R,3R)-3-(4-nitrophenoxy)cyclohexanamine (58 mg, 0.25 mmol) were dissolved in 1.0 mL of NMP, 0.2 mL of DIPEA was added and the mixture was heated to 140° C. and kept stirring for 5 h. The reaction mixture was then cooled to room temperature and diluted with EtOAc (20 mL), washed with sat. NaHCO₃ (5 mL), brine (5 mL), dried (anhydrous Na₂SO₄), filtered and concentrated under reduced pressure. The residue was used directly for the next step without further purification. LC-MS (m/z): 604 [M+H]⁺.

N-((1R,3R)-3-(4-aminophenoxy)cyclohexyl)-5-chloro-4-(1-(phenylsulfonyl)-1H-indol-3-yl)pyrimidin-2-amine

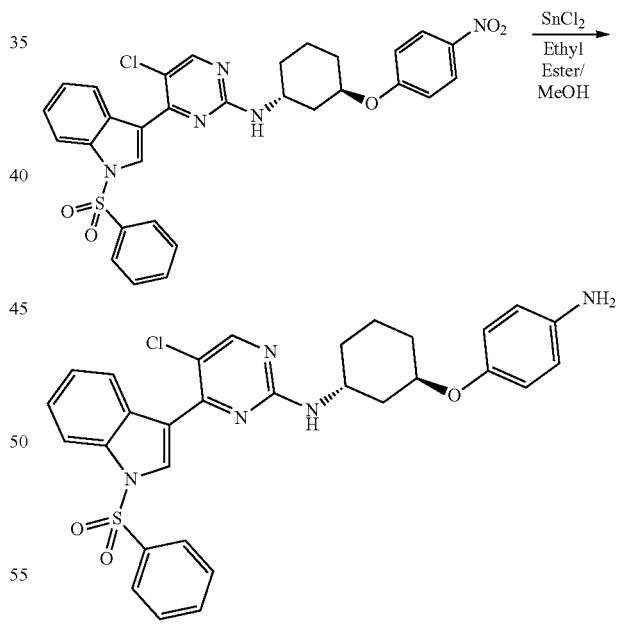

To a solution of 5-chloro-N-((1R,3R)-3-(4-nitrophenoxy)cyclohexyl)-4-(1-(phenylsulfonyl)-1H-indol-3-yl)pyrimidin-2-amine abtained from last step in 5.0 mL of ethyl ester (4.0 mL) and MeOH (1.0 mL) was added SnCl₂ (230 mg, 1.2 mmol). The mixture was heated to 80° C. and kept stirring for 2 h. Then the reaction mixture was cooled to room temperature and diluted with 100 mL of sat. NaHCO₃, extracted with 200 mL of CHCl₃/i-PrOH (v/v=4:1), washed with brine (3×100 mL), dried (anhydrous Na₂SO₄), filtered and concentrated under reduced pressure. The residue was used directly for the next step without further purification. LC-MS (m/z): 574 [M+H]+.

N-((1R,3R)-3-(4-aminophenoxy)cyclohexyl)-5-chloro-4-(1H-indol-3-yl)pyrimidin-2-amine

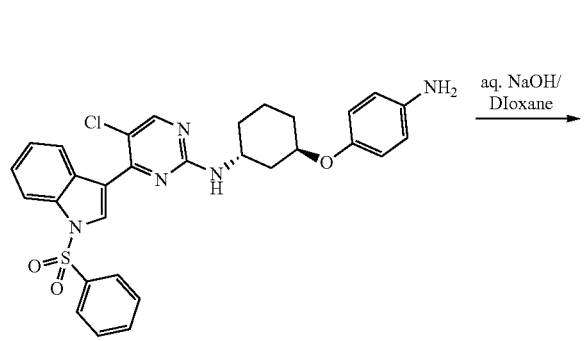

To a suspension of N-((1R,3R)-3-(4-aminophenoxy)cyclohexyl)-5-chloro-4-(1-(phenylsulfonyl)-1H-indol-3-yl)pyrimidin-2-amine obtained from last step in 2.0 mL of dioxane was added 2.0 mL of 1N of aqu. NaOH and stirred for 5 h at room temperature. Then 2.0 mL of 1N HCl was added to quench the reaction and the solvent was evaporated under reduced pressure. The residue was purified by prep-HPLC (MeOH/H2O, 0.05% TFA) to give the title compound (38.9 mg, 75% in 3 steps). LC-MS (m/z): 434 [M+H]+.

N-(4-((1R,3R)-3-(5-chloro-4-(1H-indol-3-yl)pyrimidin-2-ylamino)cyclohexyloxy)phenyl)acrylamide (BSJ-01-033)

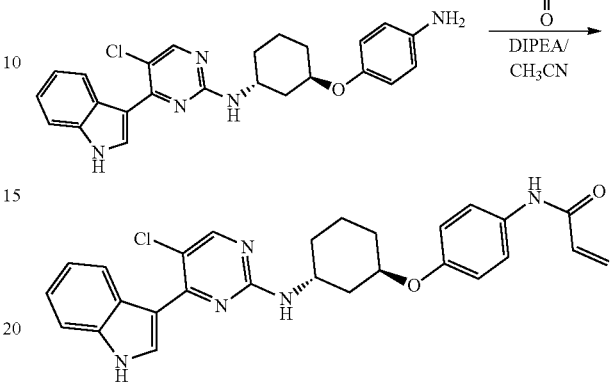

To a solution of N-((1R,3R)-3-(4-aminophenoxy)cyclohexyl)-5-chloro-4-(1H-indol-3-yl)pyrimidin-2-amine (15 mg, 0.035 mmol) and 0.1 mL of DIPEA in 2.0 mL of anhydrous CH3CN was added acryloyl chloride (3.46 mg, 0.038 mmol) in 1.0 mL of DCM dropwise, and stirred for 1 h at 0° C. The reaction mixture was then concentrated and the residue was purified by prep-HPLC (MeOH/H2O, 0.05% TFA) to give the title compound (14.8 mg, 87%) as a light yellow solid after lyophilisation. LC-MS (m/z): 488 [M+H]+. 1H NMR (500 MHz, DMSO-d6) δ 10.99 (dd, J=10.4, 5.6 Hz, 1H), 10.36 (s, 1H), 8.60 (d, J=8.4 Hz, 2H), 8.36 (s, 1H), 7.66 (d, J=8.7 Hz, 2H), 7.54 (d, J=8.1 Hz, 1H), 7.49-7.31 (m, 1H), 7.25 (t, J=7.6 Hz, 1H), 7.21-7.13 (m, 3H), 7.09-6.96 (m, 2H), 6.76 (dt, J=14.7, 7.2 Hz, 1H), 6.48 (d, J=15.3 Hz, 1H), 4.81 (s, 1H), 2.22-1.94 (m, 2H), 1.88-1.69 (m, 3H), 1.69-1.50 (m, 2H), 1.43 (d, J=11.9 Hz, 2H).

Example 2. Synthesis of (E)-N-(4-((1R,3R)-3-(5-chloro-4-(1H-indol-3-yl)pyrimidin-2-ylamino)cyclohexyloxy)phenyl)-4-(dimethylamino)but-2-enamide (BSJ-01-175)

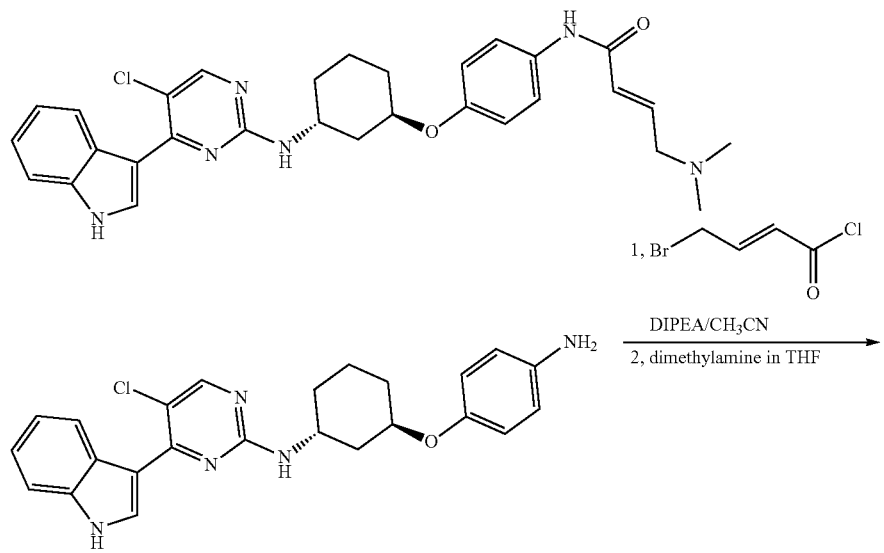

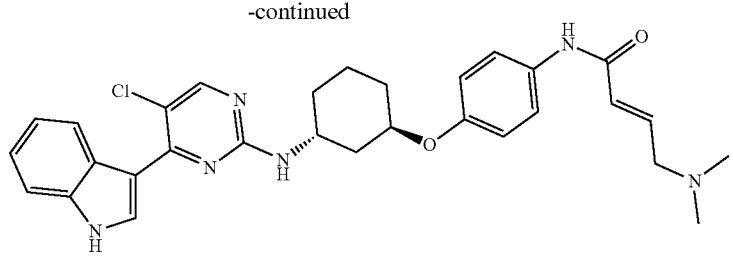

To a cold solution (0° C.) of N-((1R,3R)-3-(4-aminophenoxy)cyclohexyl)-5-chloro-4-(1H-indol-3-yl)pyrimidin-2-amine (15 mg, 0.035 mmol) and 0.1 mL of DIPEA in 2.0 mL of anhydrous CH₃CN was added a solution of (E)-4-bromobut-2-enoyl chloride (6.34 mg, 0.035 mmol) in 1.0 mL of DCM dropwise. After 0.5 h at 0° C., a 2M solution of dimethylamine in THF (1.0 mL) was added and the mixture was stirred for 1 h at 0° C. Then 1.5 mL of DMSO was added, followed by removal of the low boiling point solvents under reduced pressure. The residue was purified by prep-HPLC (MeOH/H₂O, 0.05% TFA) to give the title compound (11 mg, 58%) as a light yellow solid after lyophilisation. LC-MS (m/z): 545 [M+H]⁺. ¹H NMR (500 MHz, DMSO-d6) δ 10.92 (dd, J=10.4, 5.6 Hz, 1H), 10.38 (s, 1H), 8.65 (d, J=8.4 Hz, 2H), 8.36 (s, 1H), 7.59 (d, J=8.7 Hz, 2H), 7.54 (d, J=8.1 Hz, 1H), 7.34 (d, J=50.9 Hz, 1H), 7.25 (t, J=7.6 Hz, 1H), 7.21-7.13 (m, 2H), 6.95 (d, J=9.0 Hz, 2H), 6.76 (dt, J=14.7, 7.2 Hz, 1H), 6.48 (d, J=15.3 Hz, 1H), 4.81 (s, 1H), 3.89 (t, J=6.1 Hz, 2H), 2.74 (s, 3H), 2.73 (s, 3H), 2.22-1.94 (m, 2H), 1.88-1.69 (m, 3H), 1.69-1.50 (m, 2H), 1.43 (d, J=11.9 Hz, 2H).

Example 3. Synthesis of (E)-N-(4-(3-(5-chloro-4-(1H-indol-3-yl)pyrimidin-2-ylamino)cyclohexyloxy)phenyl)-4-(dimethylamino)but-2-enamide (BSJ-01-193)

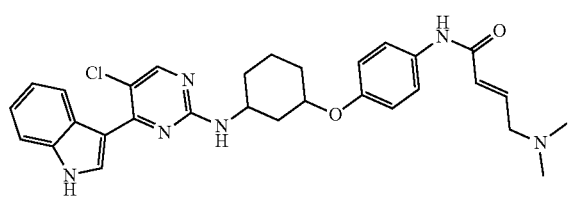 [SMILES: CN(C)C/C=C/C(=O)Nc1ccc(OC2CCCC(Nc3ncc(Cl)c(-c4c[nH]c5ccccc45)n3)C2)cc1]

3-(4-nitrophenoxy)cyclohexanamine

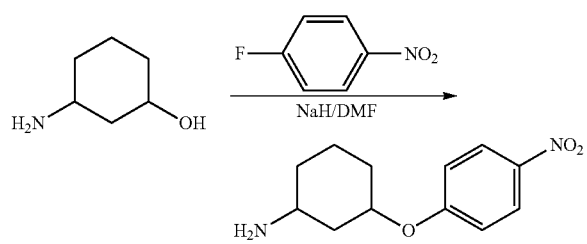

To a suspension of NaH (0.8 g, 8.25 mmol) in 3.0 mL of anhydrous DMF was added 3-aminocyclohexanol HCl salt (0.5 g, 3.3 mmol) slowly at 0° C. and kept stirring for 0.5 h, then 1-fluoro-4-nitrobenzene (0.465 g, 3.3 mmol) was added. The reaction mixture was kept stirring at 0° C. for another 0.5 h, then warm to room temperature and kept stirring for 2 h. 1.0 mL of H₂O was added dropwise to quench the reaction. The mixture was extracted with DCM (100 mL), washed with brine (3×50 mL), dried (anhydrous Na₂SO₄), filtered and concentrated under reduced pressure. The residue was purified by chromatography on silica gel to give the title compound (623 mg, 80%) as a brown solid. LC-MS (m/z): 237 [M+H]⁺.

5-chloro-N-(3-(4-nitrophenoxy)cyclohexyl)-4-(1-(phenylsulfonyl)-1H-indol-3-yl)pyrimidin-2-amine

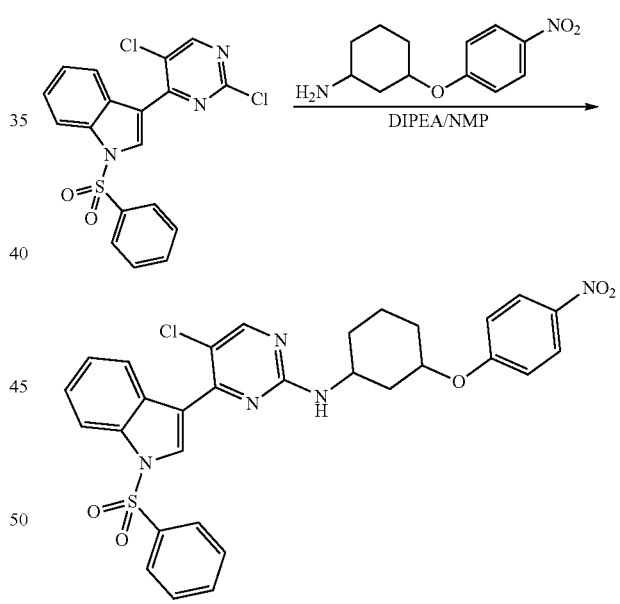

3-(2,5-dichloropyrimidin-4-yl)-1-(phenylsulfonyl)-1H-indole (50 mg, 0.12 mmol) and 3-(4-nitrophenoxy)cyclohexanamine (58 mg, 0.25 mmol) were dissolved in 1.0 mL of NMP, 0.2 mL of DIPEA was added and the mixture was heated to 140° C. and kept stirring for 5 h. The reaction mixture was then cooled to room temperature and diluted with EtOAc (20 mL), washed with sat. NaHCO₃ (5 mL), brine (5 mL), dried (anhydrous Na₂SO₄), filtered and concentrated under reduced pressure. The residue was used directly for the next step without further purification. LC-MS (m/z): 604 [M+H]⁺.

159
N-(3-(4-aminophenoxy)cyclohexyl)-5-chloro-4-(1-(phenylsulfonyl)-1H-indol-3-yl)pyrimidin-2-amine

160
N-(3-(4-aminophenoxy)cyclohexyl)-5-chloro-4-(1H-indol-3-yl)pyrimidin-2-amine

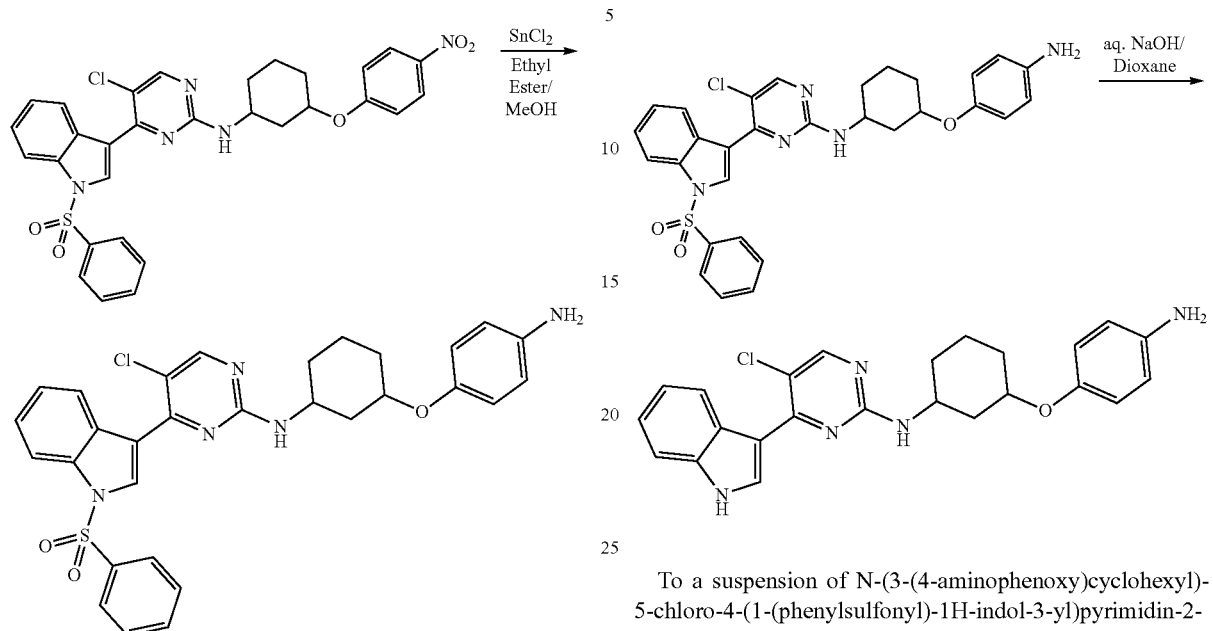

To a solution of 5-chloro-N-(3-(4-nitrophenoxy)cyclohexyl)-4-(1-(phenylsulfonyl)-1H-indol-3-yl)pyrimidin-2-amine abtained from last step in 5.0 mL of ethyl ester (4.0 mL) and MeOH (1.0 mL) was added SnCl₂ (230 mg, 1.2 mmol). The mixture was heated to 80° C. and kept stirring for 2 h. Then the reaction mixture was cooled to room temperature and diluted with 100 mL of sat. NaHCO₃, extracted with 200 mL of CHCl₃/i-PrOH (v/v=4:1), washed with brine (3×100 mL), dried (anhydrous Na₂SO₄), filtered and concentrated under reduced pressure. The residue was used directly for the next step without further purification. LC-MS (m/z): 574 [M+H]⁺.

To a suspension of N-(3-(4-aminophenoxy)cyclohexyl)-5-chloro-4-(1-(phenylsulfonyl)-1H-indol-3-yl)pyrimidin-2-amine obtained from last step in 2.0 mL of dioxane was added 2.0 mL of 1N of aq. NaOH and stirred for 5 h at room temperature. Then 2.0 mL of 1N HCl was added to quench the reaction and the solvent was evaporated under reduced pressure. The residue was purified by prep-HPLC (MeOH/H₂O, 0.05% TFA) to give the title compound (38.8 mg, 75% in 3 steps). LC-MS (m/z): 434 [M+H]⁺.

(E)-N-(4-(3-(5-chloro-4-(1H-indol-3-yl)pyrimidin-2-ylamino)cyclohexyloxy)phenyl)-4-(dimethylamino)but-2-enamide

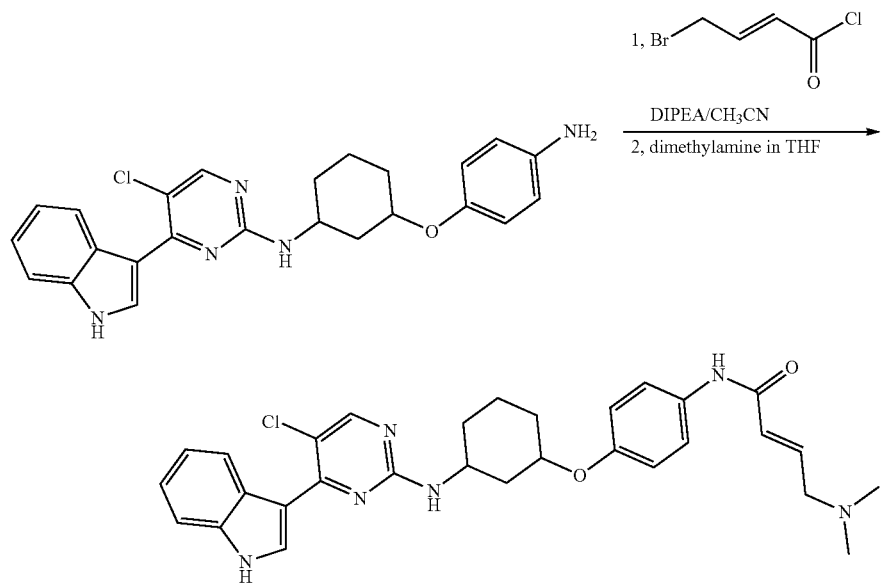

To a cold solution (0° C.) of N-(3-(4-aminophenoxy) cyclohexyl)-5-chloro-4-(1H-indol-3-yl)pyrimidin-2-amine (15 mg, 0.035 mmol) and 0.1 mL of DIPEA in 2.0 mL of anhydrous CH$_3$CN was added a solution of (E)-4-bromobut-2-enoyl chloride (6.34 mg, 0.035 mmol) in 1.0 mL of DCM dropwise. After 0.5 h at 0° C., a 2M solution of dimethylamine in THF (1.0 mL) was added and the mixture was stirred for 1 h at 0° C. Then 1.5 mL of DMSO was added, followed by removal of the low boiling point solvents under reduced pressure. The residue was purified by prep-HPLC (MeOH/H$_2$O, 0.05% TFA) to give the title compound (11 mg, 58%) as a light yellow solid after lyophilisation. LC-MS (m/z): 545[M+H]$^+$. $^1$H NMR (500 MHz, DMSO-d6) δ 10.92 (dd, J=10.4, 5.6 Hz, 1H), 10.38 (s, 1H), 8.65 (d, J=8.4 Hz, 2H), 8.36 (s, 1H), 7.59 (d, J=8.7 Hz, 2H), 7.54 (d, J=8.1 Hz, 1H), 7.34 (d, J=50.9 Hz, 1H), 7.25 (t, J=7.6 Hz, 1H), 7.21-7.13 (m, 2H), 6.95 (d, J=9.0 Hz, 2H), 6.76 (dt, J=14.7, 7.2 Hz, 1H), 6.48 (d, J=15.3 Hz, 1H), 4.81 (s, 1H), 3.89 (t, J=6.1 Hz, 2H), 2.74 (s, 3H), 2.73 (s, 3H), 2.22-1.94 (m, 2H), 1.88-1.69 (m, 3H), 1.69-1.50 (m, 2H), 1.43 (d, J=11.9 Hz, 2H).

Example 4. Synthesis of (E)-N-(6-(3-(5-chloro-4-(1H-indol-3-yl)pyrimidin-2-ylamino)piperidine-1-carbonyl)pyridin-3-yl)-4-(dimethylamino)but-2-enamide (BSJ-01-202)

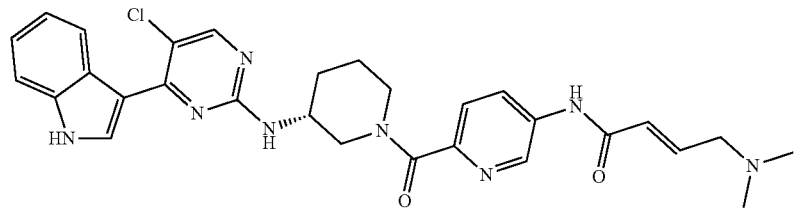 [SMILES: CN(C)C/C=C/C(=O)Nc1ccc(C(=O)N2CCC[C@@H](Nc3ncc(Cl)c(-c4c[nH]c5ccccc45)n3)C2)nc1]

(R)-tert-butyl 3-(5-chloro-4-(1-(phenylsulfonyl)-1H-indol-3-yl)pyrimidin-2-ylamino)piperidine-1-carboxylate

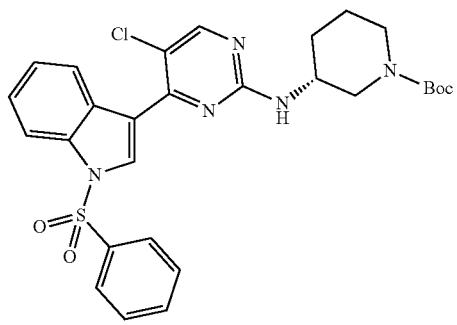

3-(2,5-dichloropyrimidin-4-yl)-1-(phenylsulfonyl)-1H-indole (500 mg, 1.2 mmol) and (R)-tert-butyl 3-aminopiperidine-1-carboxylate (480 mg, 2.4 mmol) were dissolved in 5.0 mL of NMP, 0.8 mL of DIPEA was added and the mixture was heated to 140° C. and kept stirring for 5 h. The reaction mixture was then cooled to room temperature and diluted with EtOAc (20 mL), washed with sat. NaHCO$_3$ (5 mL), brine (5 mL), dried (anhydrous Na$_2$SO$_4$), filtered and concentrated under reduced pressure. The residue was purified by chromatography on silica gel to give the title compound (620 mg, 91%). LC-MS (m/z): 568 [M+H]$^+$.

(R)-(3-(5-chloro-4-(1-(phenylsulfonyl)-1H-indol-3-yl)pyrimidin-2-ylamino)piperidin-1-yl)(5-nitropyridin-2-yl)methanone

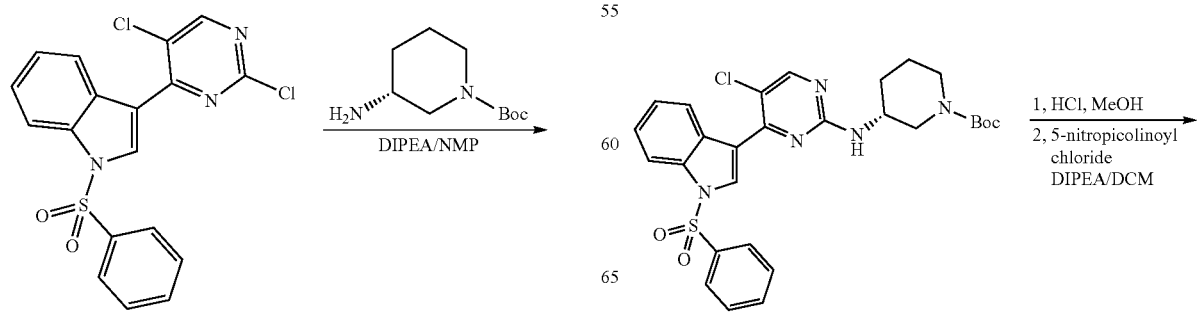

-continued

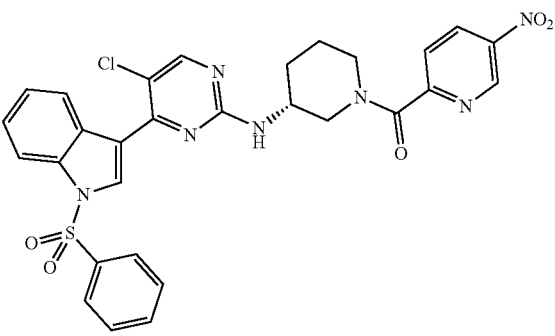

A solution of (R)-tert-butyl 3-(5-chloro-4-(1-(phenylsulfonyl)-1H-indol-3-yl)pyrimidin-2-ylamino)piperidine-1-carboxylate (100 mg, 0.18 mmol) in 5 mL of MeOH was treated with 2.0 mL of 4N HCl in dioxane. The resulting mixture was stirred for 4 h at room temperature before being evaporated to dryness. The residue was then dissolved in 5.0 mL of DCM, 0.5 mL of DIPEA was added and the mixture was cooled to 0° C. 5-nitropicolinoyl chloride (36.2 mg, 0.19 mmol) was added and the reaction mixture was kept stirring for 2 h at room temperature before being evaporated to dryness. The residue was used directly for the next step without further purification. LC-MS (m/z): 618 [M+H]+.

(R)-(5-aminopyridin-2-yl)(3-(5-chloro-4-(1-(phenylsulfonyl)-1H-indol-3-yl)pyrimidin-2-ylamino)piperidin-1-yl)methanone

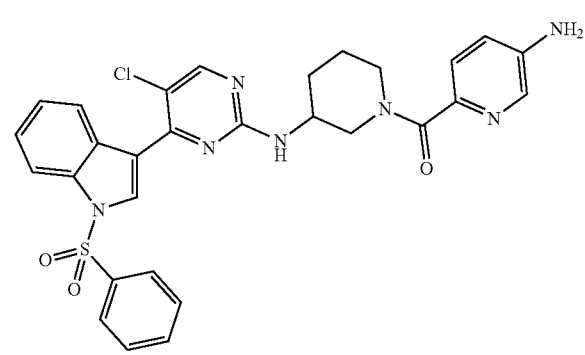

To a solution of (R)-(3-(5-chloro-4-(1-(phenylsulfonyl)-1H-indol-3-yl)pyrimidin-2-ylamino)piperidin-1-yl)(5-nitropyridin-2-yl)methanone abtained from last step in 5 mL of ethyl ester (4.0 mL) and MeOH (1.0 mL) was added SnCl₂ (340.0 mg, 1.8 mmol). The mixture was heated to 80° C. and kept stirring for 2 h. Then the reaction mixture was cooled to room temperature and diluted with 100 mL of sat. NaHCO₃, extracted with 200 mL of CHCl₃/i-PrOH (v/v=4:1), washed with brine (3×100 mL), dried (anhydrous Na₂SO₄), filtered and concentrated under reduced pressure. The residue was used directly for the next step without further purification. LC-MS (m/z): 588 [M+H]+.

(R)-(5-aminopyridin-2-yl)(3-(5-chloro-4-(1H-indol-3-yl)pyrimidin-2-ylamino)piperidin-1-yl)methanone

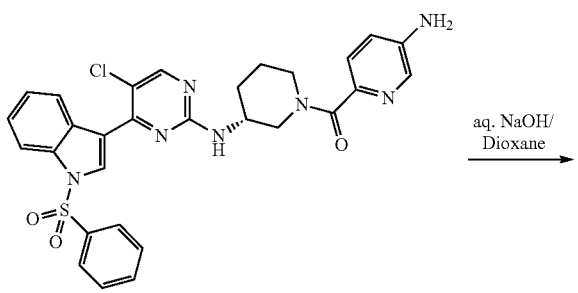

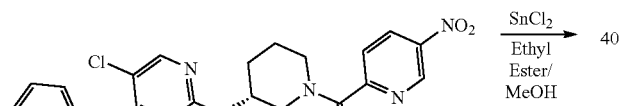

To a solution of (R)-(5-aminopyridin-2-yl)(3-(5-chloro-4-(1-(phenylsulfonyl)-1H-indol-3-yl)pyrimidin-2-ylamino)piperidin-1-yl)methanone obtained from last step in 2.0 mL of dioxane was added 2.0 mL of 1N of aq. NaOH and stirred for 5 h at room temperature. Then 2.0 mL of 1N HCl was added to quench the reaction and the solvent was evaporated under reduced pressure. The residue was purified by prep-HPLC (MeOH/H₂O, 0.05% TFA) to give the title compound (40 mg, 50% in 4 steps). LC-MS (m/z): 448 [M+H]+.

(E)-N-(6-(3-(5-chloro-4-(1H-indol-3-yl)pyrimidin-2-ylamino)piperidine-1-carbonyl)pyridin-3-yl)-4-(dimethylamino)but-2-enamide

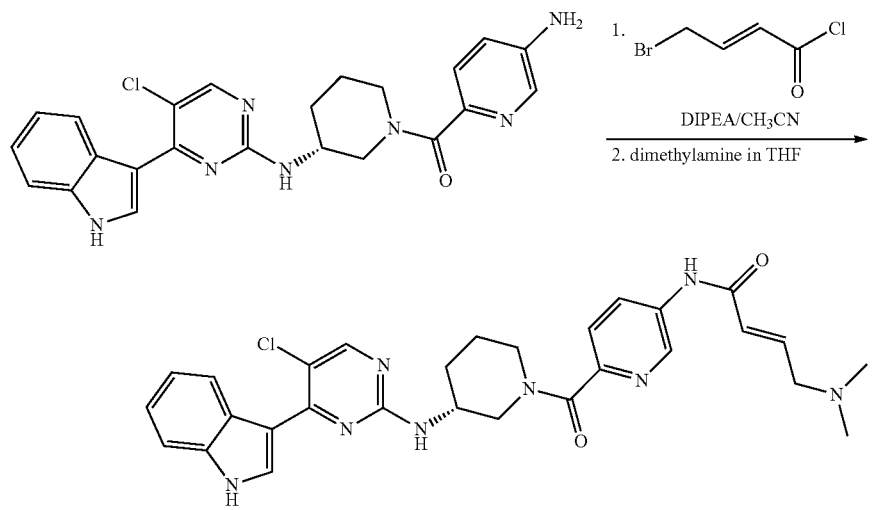

To a cold solution (0° C.) of (R)-(5-aminopyridin-2-yl) (3-(5-chloro-4-(1H-indol-3-yl)pyrimidin-2-ylamino)piperidin-1-yl)methanone (16 mg, 0.035 mmol) and 0.1 mL of DIPEA in 2.0 mL of anhydrous CH₃CN was added a solution of (E)-4-bromobut-2-enoyl chloride (6.34 mg, 0.035 mmol) in 1.0 mL of DCM dropwise. After 0.5 h at 0° C., a 2M solution of dimethylamine in THF (1.0 mL) was added and the mixture was stirred for 1 h at 0° C. Then 1.5 mL of DMSO was added, followed by removal of the low boiling point solvents under reduced pressure. The residue was purified by prep-HPLC (MeOH/H₂O, 0.05% TFA) to give the title compound (12 mg, 61%) as a light yellow solid after lyophilisation. LC-MS (m/z): 559 [M+H]⁺. ¹H NMR (500 MHz, DMSO-d6) δ 11.99-11.79 (m, 1H), 10.81-10.54 (M, 1H), 9.88 (s, 1H), 8.92-8.57 (m, 1H), 8.39-8.22 (m, 1H), 8.02 (d, J=8.6 Hz, 1H), 7.63 (d, J=8.5 Hz, 1H), 7.55-7.29 (m, 2H), 7.25-7.17 (m, 1H), 7.16-7.05 (m, 1H), 6.91-6.68 (m, 1H), 6.56-6.39 (m, 1H), 3.96 (d, J=9.2 Hz, 2H), 3.85-3.61 (m, 1H), 3.48 (s, 1H), 3.07 (s, 1H), 2.81 (s, 6H), 2.17-1.94 (m, 2H), 1.84-1.70 (m, 2H), 1.70-1.45 (m, 2H).

Example 5. Synthesis of N-(6-(3-(5-bromo-4-(1H-indol-3-yl)pyrimidin-2-ylamino)piperidine-1-carbonyl)pyridin-3-yl)acrylamide (BSJ-02-057)

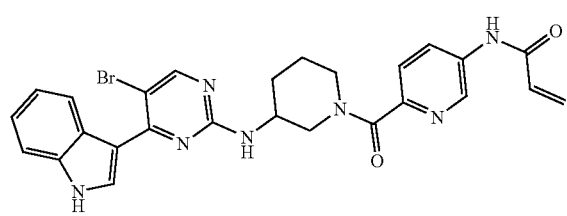 [SMILES: C=CC(=O)Nc1ccc(C(=O)N2CCCC(Nc3ncc(Br)c(-c4c[nH]c5ccccc45)n3)C2)nc1]

(R)-tert-butyl 3-(5-bromo-4-(1-(phenylsulfonyl)-1H-indol-3-yl)pyrimidin-2-ylamino)piperidine-1-carboxylate

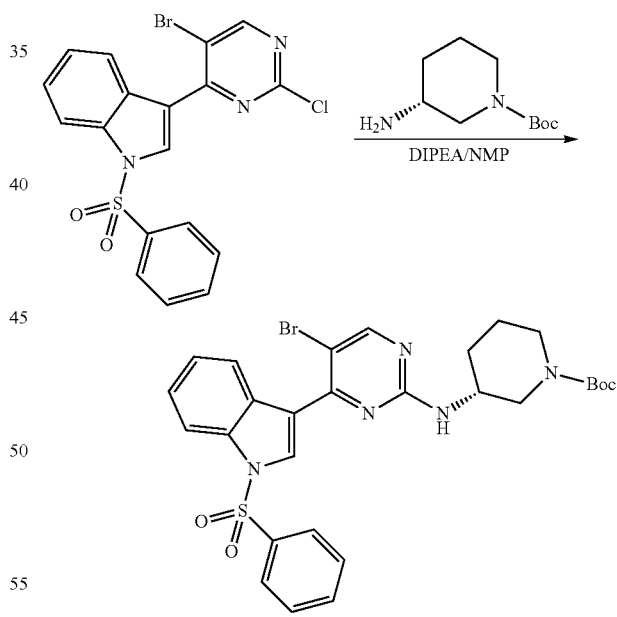

3-(5-bromo-2-chloropyrimidin-4-yl)-1-(phenylsulfonyl)-1H-indole (536 mg, 1.2 mmol) and (R)-tert-butyl 3-aminopiperidine-1-carboxylate (480 mg, 2.4 mmol) were dissolved in 5.0 mL of NMP, 0.8 mL of DIPEA was added and the mixture was heated to 140° C. and kept stirring for 5 h. The reaction mixture was then cooled to room temperature and diluted with EtOAc (20 mL), washed with sat. NaHCO₃ (5 mL), brine (5 mL), dried (anhydrous Na₂SO₄), filtered and concentrated under reduced pressure. The residue was purified by chromatography on silica gel to give the title compound (594 mg, 81%). LC-MS (m/z): 612 [M+H]⁺.

(R)-3-(5-bromo-4-(1-(phenylsulfonyl)-1H-indol-3-yl)pyrimidin-2-ylamino)piperidin-1-yl)(5-nitropyridin-2-yl)methanone

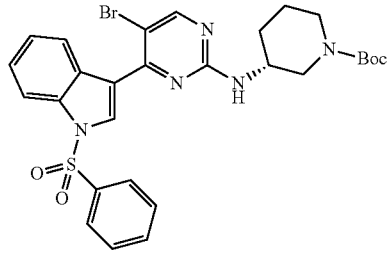

1. HCl, MeOH
2. 5-nitropicolinoyl chloride DIPEA/DCM

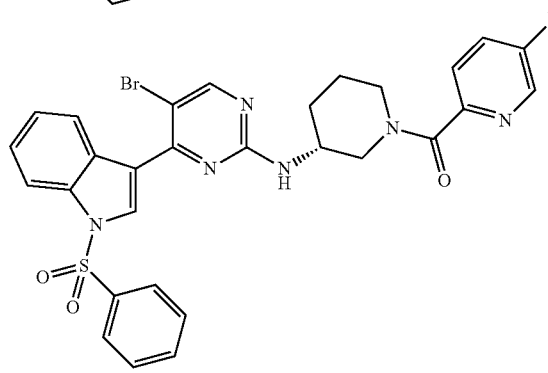

A solution of (R)-tert-butyl 3-(5-bromo-4-(1-(phenylsulfonyl)-1H-indol-3-yl)pyrimidin-2-ylamino)piperidine-1-carboxylate (110 mg, 0.18 mmol) in 5 mL of MeOH was treated with 2.0 mL of 4N HCl in dioxane. The resulting mixture was stirred for 4 h at room temperature before being evaporated to dryness. The residue was then dissolved in 5.0 mL of DCM, 0.5 mL of DIPEA was added and the mixture was cooled to 0° C. 5-nitropicolinoyl chloride (36.2 mg, 0.19 mmol) was added and the reaction mixture was kept stirring for 2 h at room temperature before being evaporated to dryness. The residue was used directly for the next step without further purification. LC-MS (m/z): 662 [M+H]⁺.

(R)-(5-aminopyridin-2-yl)(3-(5-bromo-4-(1-(phenylsulfonyl)-1H-indol-3-yl)pyrimidin-2-ylamino)piperidin-1-yl)methanone

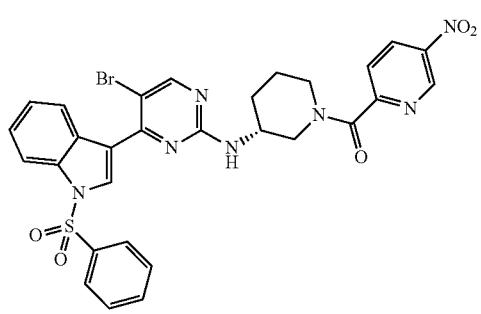

SnCl₂
Ethyl Ester/ MeOH

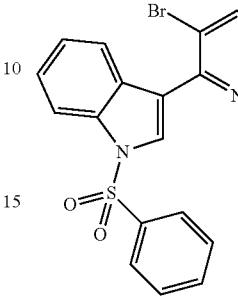

To a solution of (R)-(3-(5-bromo-4-(1-(phenylsulfonyl)-1H-indol-3-yl)pyrimidin-2-ylamino)piperidin-1-yl)(5-nitropyridin-2-yl)methanone abtained from last step in 5 mL of ethyl ester (4.0 mL) and MeOH (1.0 mL) was added SnCl₂ (340.0 mg, 1.8 mmol). The mixture was heated to 80° C. and kept stirring for 2 h. Then the reaction mixture was cooled to room temperature and diluted with 100 mL of sat. NaHCO₃, extracted with 200 mL of CHCl₃/i-PrOH (v/v=4:1), washed with brine (3×100 mL), dried (anhydrous Na₂SO₄), filtered and concentrated under reduced pressure. The residue was used directly for the next step without further purification. LC-MS (m/z): 632 [M+H]⁺.

(R)-(5-aminopyridin-2-yl)(3-(5-bromo-4-(1H-indol-3-yl)pyrimidin-2-ylamino)piperidin-1-yl)methanone

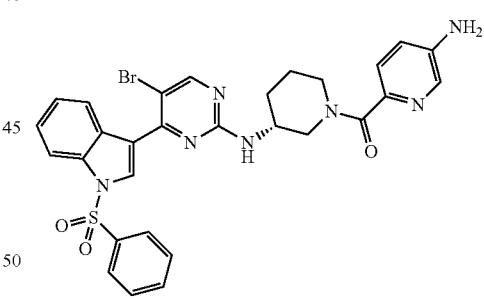

aq. NaOH/ Dioxane

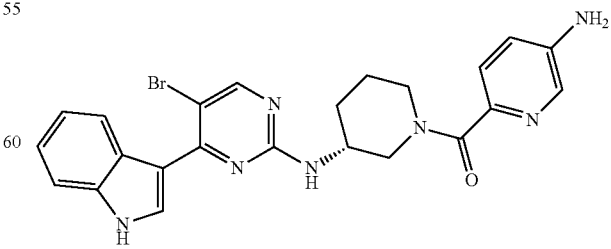

To a solution of (R)-(3-(5-bromo-4-(1-(phenylsulfonyl)-1H-indol-3-yl)pyrimidin-2-ylamino)piperidin-1-yl)(5-nitropyridin-2-yl)methanone obtained from last step in 2.0 mL of dioxane was added 2.0 mL of 1N of aq. NaOH and stirred for 5 h at room temperature. Then 2.0 mL of 1N HCl was added to quench the reaction and the solvent was evaporated under reduced pressure. The residue was purified by prep-HPLC (MeOH/H₂O, 0.05% TFA) to give the title compound (51 mg, 51% in 4 steps). LC-MS (m/z): 492 [M+H]⁺.

N-(6-(3-(5-bromo-4-(1H-indol-3-yl)pyrimidin-2-ylamino)piperidine-1-carbonyl)pyridin-3-yl)acrylamide

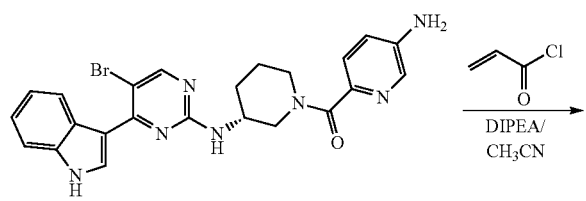

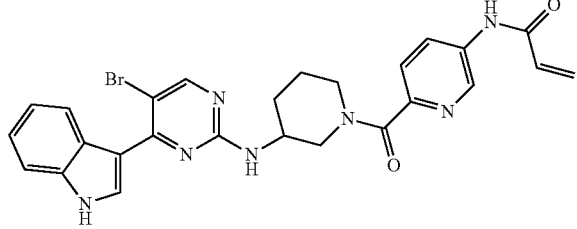

To a solution of (R)-(5-aminopyridin-2-yl)(3-(5-bromo-4-(1H-indol-3-yl)pyrimidin-2-ylamino)piperidin-1-yl)methanone (17 mg, 0.035 mmol) and 0.1 mL of DIPEA in 2.0 mL of anhydrous CH₃CN was added acryloyl chloride (3.46 mg, 0.038 mmol) in 1.0 mL of DCM dropwise, and stirred for 1 h at 0° C. The reaction mixture was then concentrated and the residue was purified by prep-HPLC (MeOH/H₂O, 0.05% TFA) to give the title compound (17.2 mg, 90%) as a light yellow solid after lyophilisation. LC-MS (m/z): 546 [M+H]⁺. ¹H NMR (500 MHz, DMSO-d6) δ 11.94-11.70 (m, 1H), 10.69-10.25 (m, 1H), 8.94-8.69 (m, 1H), 8.65-8.34 (m, 1H), 8.34-7.93 (m, 1H), 7.81-7.56 (m, 1H), 7.48 (d, J=8.0 Hz, 1H), 7.44-7.29 (m, 2H), 7.19 (t, J=7.4 Hz, 1H), 7.12 (t, J=7.4 Hz, 1H), 6.45 (ddd, J=21.8, 16.7, 10.0 Hz, 1H), 6.37-6.22 (m, 1H), 5.94-5.83 (m, 1H), 4.67-4.37 (m, 1H), 3.20-2.78 (m, 1H), 2.15-1.59 (m, 3H), 1.53 (qt, J=8.1, 4.5 Hz, 1H), 1.42 (d, J=6.5 Hz, 1H), 1.37-1.14 (m, 2H).

Example 6. Synthesis of (E)-N-(6-(3-(5-bromo-4-(1H-indol-3-yl)pyrimidin-2-ylamino)piperidine-1-carbonyl)pyridin-3-yl)-4-(dimethylamino)but-2-enamide (BSJ-02-058)

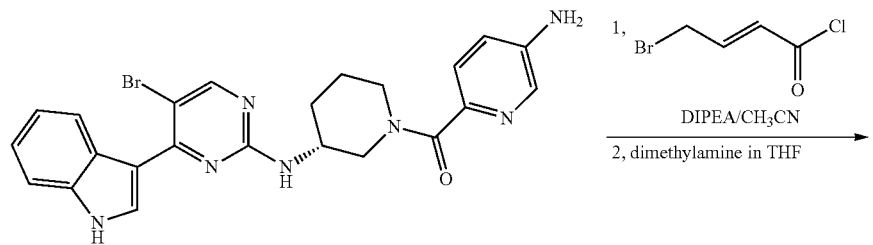

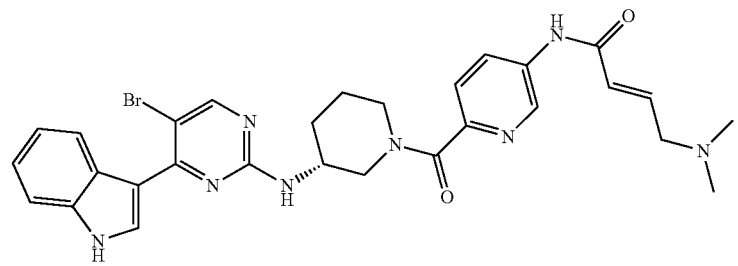

To a cold solution (0° C.) of (R)-(5-aminopyridin-2-yl) (3-(5-bromo-4-(1H-indol-3-yl)pyrimidin-2-ylamino)piperidin-1-yl)methanone (17 mg, 0.035 mmol) and 0.1 mL of DIPEA in 2.0 mL of anhydrous CH₃CN was added a solution of (E)-4-bromobut-2-enoyl chloride (6.34 mg, 0.035 mmol) in 1.0 mL of DCM dropwise. After 0.5 h at 0° C., a 2M solution of dimethylamine in THF (1.0 mL) was added and the mixture was stirred for 1 h at 0° C. Then 1.5 mL of DMSO was added, followed by removal of the low boiling point solvents under reduced pressure. The residue was purified by prep-HPLC (MeOH/H₂O, 0.05% TFA) to give the title compound (12 mg, 61%) as a light yellow solid after lyophilisation. LC-MS (m/z): 603 [M+H]⁺. ¹H NMR (500 MHz, DMSO-d6) δ 11.81 (dd, J=13.1, 3.1 Hz, 1H), 10.87-10.64 (m, 1H), 9.94 (s, 1H), 8.91-8.75 (m, 1H), 8.66-8.35 (m, 3H), 8.23 (dd, J=8.5, 2.5 Hz, 1H), 8.17-7.91 (m, 1H), 7.76-7.61 (m, 2H), 7.44-7.24 (m, 2H), 7.21-7.02 (m, 2H), 6.80 (ddd, J=15.2, 12.7, 7.2 Hz, 1H), 6.47 (dd, J=24.4, 15.3 Hz, 1H), 4.54 (d, J=12.3 Hz, 1H), 3.22-2.90 (m, 2H), 2.81 (s, 6H), 2.17-1.84 (m, 2H), 1.77 (d, J=14.0 Hz, 1H), 1.70-1.46 (m, 2H), 1.32-1.14 (m, 1H).

Example 7. Synthesis of (E)-N-(6-(3-(5-bromo-4-(1H-indol-3-yl)pyrimidin-2-ylamino)piperidine-1-carbonyl)pyridin-3-yl)-4-(dimethylamino)but-2-enamide (BSJ-03-055)

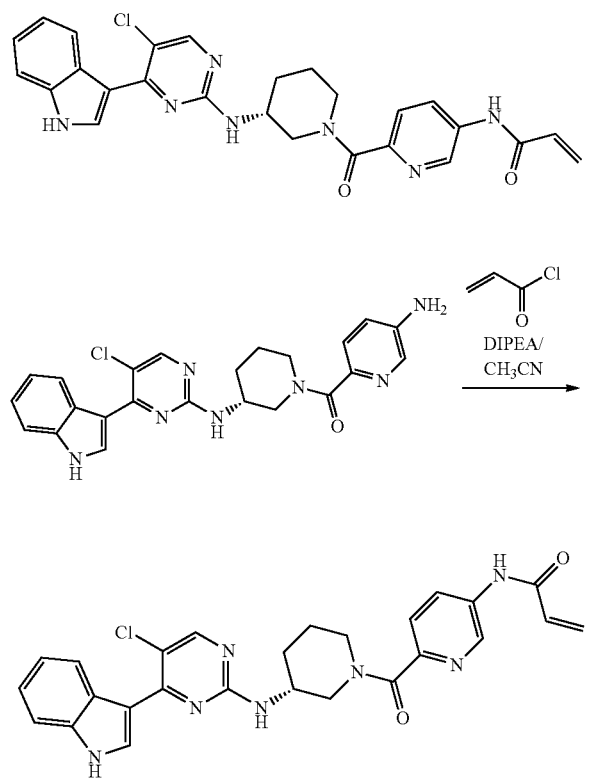

To a solution of (R)-(5-aminopyridin-2-yl)(3-((5-chloro-4-(1H-indol-3-yl)pyrimidin-2-yl)amino)piperidin-1-yl) methanone (16 mg, 0.035 mmol) and 0.1 mL of DIPEA in 2.0 mL of anhydrous CH₃CN was added acryloyl chloride (3.46 mg, 0.038 mmol) in 1.0 mL of DCM dropwise, and stirred for 1 h at 0° C. The reaction mixture was then concentrated and the residue was purified by prep-HPLC (MeOH/H₂O, 0.05% TFA) to give the title compound (17.2 mg, 90%) as a light yellow solid after lyophilisation. LC-MS (m/z): 502 [M+H]⁺. ¹H NMR (500 MHz, DMSO-d6) δ 11.80 (s, 1H), 10.66 (s, 1H), 9.78 (s, 1H), 8.98-8.67 (m, 1H), 8.39-8.22 (m, 1H), 8.10 (d, J=8.6 Hz, 1H), 7.68 (d, J=8.5 Hz, 1H), 7.55-7.29 (m, 2H), 7.25-7.17 (m, 1H), 7.16-7.05 (m, 1H), 6.85-6.61 (m, 1H), 6.56-6.39 (m, 1H), 3.86 (d, J=9.0 Hz, 2H), 3.85-3.61 (m, 1H), 3.48 (s, 1H), 3.07 (s, 1H), 2.27-1.99 (m, 2H), 1.88-1.73 (m, 2H), 1.71-1.45 (m, 2H).

Example 8. Synthesis of (R)—N-(4-(3-((5-chloro-4-(1H-indol-3-yl)pyrimidin-2-yl)amino)piperidin-1-yl) phenyl)acrylamide (BSJ-02-139)

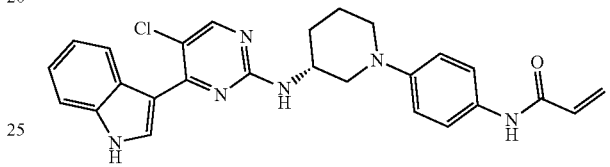

(R)-5-chloro-4-(1H-indol-3-yl)-N-(piperidin-3-yl) pyrimidin-2-amine

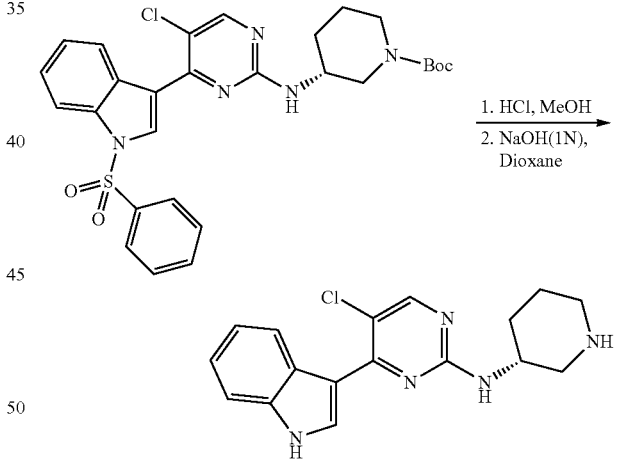

To a solution of (R)-tert-butyl 3-(5-chloro-4-(1-(phenylsulfonyl)-1H-indol-3-yl)pyrimidin-2-ylamino)piperidine-1-carboxylate (100 mg, 0.18 mmol) in 5 mL of MeOH was treated with 2.0 mL of 4N HCl in dioxane. The resulting mixture was stirred for 4 h at room temperature before being evaporated to dryness. The residue was then dissolved in 3 mL of dioxane, 3 mL of 1N aqueous NaOH was added and the mixture was stirred for 2 h. Then 1N aqueous HCl was added to adjust the pH to 7. The resulting mixture was evaporated and the residue was purified by prep-HPLC (MeOH/H₂O, 0.05% TFA) to give the title compound (54 mg, 92%) as a light yellow solid after lyophilisation. LC-MS (m/z): 328 [M+H]⁺.

(R)—N-(1-(4-aminophenyl)piperidin-3-yl)-5-chloro-4-(1H-indol-3-yl)pyrimidin-2-amine

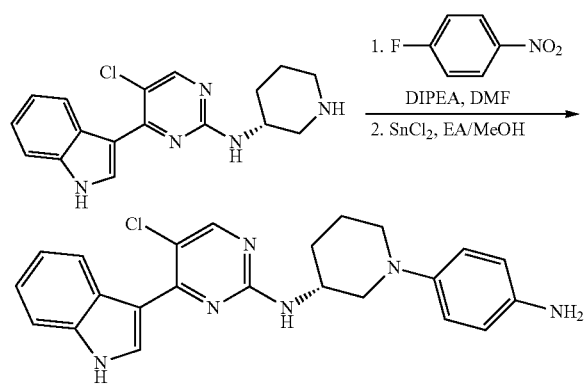

To a solution of (R)-5-chloro-4-(1H-indol-3-yl)-N-(piperidin-3-yl)pyrimidin-2-amine (54 mg, 0.17 mmol) in 3 mL of DMF was added 0.1 mL of DIPEA and 1-fluoro-4-nitrobenzene (24 mg, 0.17 mmol). The mixture was heated to 70° C. and kept stirring for 8 h. The reaction mixture was then cooled to room temperature and the solvent was evaporated. The residue was re-dissolved in 5 mL of ethyl ester (4.0 mL) and MeOH (1.0 mL), SnCl$_2$ (340.0 mg, 1.8 mmol) was added. The mixture was heated to 80° C. and kept stirring for 2 h. Then the reaction mixture was cooled to room temperature and diluted with 100 mL of sat. NaHCO$_3$, extracted with 200 mL of CHCl$_3$/i-PrOH (v/v=4:1), washed with brine (3×100 mL), dried (anhydrous Na$_2$SO$_4$), filtered and concentrated under reduced pressure. The residue was purified by prep-HPLC (MeOH/H$_2$O, 0.05% TFA) to give the title compound (59 mg, 85%) as a grey solid after lyophilisation. LC-MS (m/z): 419 [M+H]$^+$.

(R)—N-(4-(3-((5-chloro-4-(1H-indol-3-yl)pyrimidin-2-yl)amino)piperidin-1-yl)phenyl)acrylamide

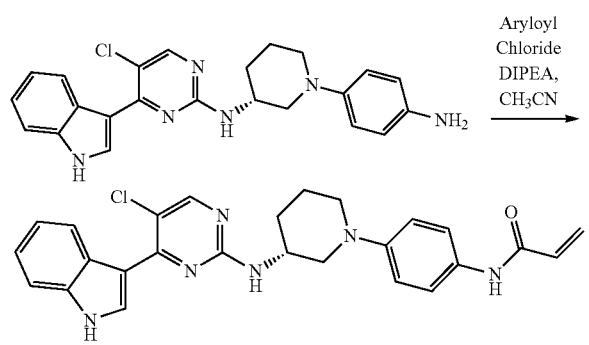

To a solution of (R)—N-(1-(4-aminophenyl)piperidin-3-yl)-5-chloro-4-(1H-indol-3-yl)pyrimidin-2-amine (15 mg, 0.035 mmol) and 0.1 mL of DIPEA in 2.0 mL of anhydrous CH$_3$CN was added acryloyl chloride (3.46 mg, 0.038 mmol) in 1.0 mL of DCM dropwise, and stirred for 1 h at 0° C. The reaction mixture was then concentrated and the residue was purified by prep-HPLC (MeOH/H$_2$O, 0.05% TFA) to give the title compound (15 mg, 91%) as a light yellow solid after lyophilisation. LC-MS (m/z): 473 [M+H]$^+$. $^1$H NMR (500 MHz, DMSO-d6) δ 11.83 (s, 1H), 10.58 (s, 1H), 8.61-8.38 (m, 1H), 8.33-7.91 (m, 1H), 7.84-7.51 (m, 1H), 7.45 (d, J=8.0 Hz, 1H), 7.49-7.25 (m, 2H), 7.13 (t, J=7.2 Hz, 1H), 7.08 (t, J=7.2 Hz, 1H), 6.59-6.42 (m, 1H), 6.34-6.20 (m, 1H), 5.90-5.85 (m, 1H), 4.67-4.36 (m, 1H), 3.22-2.80 (m, 1H), 2.05-1.62 (m, 3H), 1.60-1.49 (m, 1H), 1.48 (d, J=6.3 Hz, 1H), 1.38-1.16 (m, 2H).

Example 9. Synthesis of (R,E)-N-(4-(3-((5-chloro-4-(1H-indol-3-yl)pyrimidin-2-yl)amino)piperidin-1-yl)phenyl)-4-(dimethylamino)but-2-enamide (BSJ-02-109)

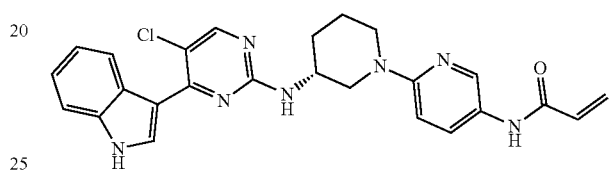

(R)—N-(1-(5-aminopyridin-2-yl)piperidin-3-yl)-5-chloro-4-(1H-indol-3-yl)pyrimidin-2-amine

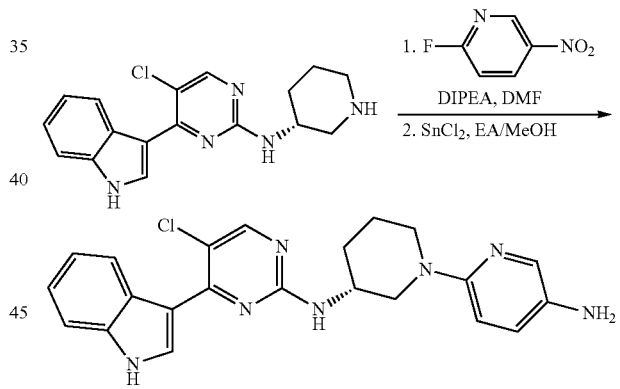

To a solution of (R)-5-chloro-4-(1H-indol-3-yl)-N-(piperidin-3-yl)pyrimidin-2-amine (54 mg, 0.17 mmol) in 3 mL of DMF was added 0.1 mL of DIPEA and 2-fluoro-5-nitropyridine (24 mg, 0.17 mmol). The mixture was heated to 70° C. and kept stirring for 8 h. The reaction mixture was then cooled to room temperature and the solvent was evaporated. The residue was re-dissolved in 5 mL of ethyl ester (4.0 mL) and MeOH (1.0 mL), SnCl$_2$ (340.0 mg, 1.8 mmol) was added. The mixture was heated to 80° C. and kept stirring for 2 h. Then the reaction mixture was cooled to room temperature and diluted with 100 mL of sat. NaHCO$_3$, extracted with 200 mL of CHCl$_3$/i-PrOH (v/v=4:1), washed with brine (3×100 mL), dried (anhydrous Na$_2$SO$_4$), filtered and concentrated under reduced pressure. The residue was purified by prep-HPLC (MeOH/H$_2$O, 0.05% TFA) to give the title compound (61 mg, 85%) as a grey solid after lyophilisation. LC-MS (m/z): 420 [M+H]$^+$.

(R)—N-(6-(3-((5-chloro-4-(1H-indol-3-yl)pyrimidin-2-yl)amino)piperidin-1-yl)pyridin-3-yl)acrylamide

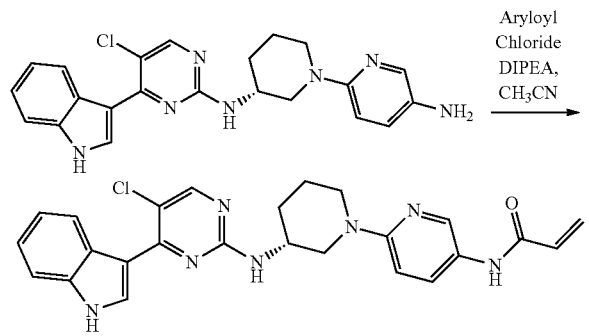

To a solution of (R)—N-(1-(5-aminopyridin-2-yl)piperidin-3-yl)-5-chloro-4-(1H-indol-3-yl)pyrimidin-2-amine (15 mg, 0.035 mmol) and 0.1 mL of DIPEA in 2.0 mL of anhydrous CH$_3$CN was added acryloyl chloride (3.46 mg, 0.038 mmol) in 1.0 mL of DCM dropwise, and stirred for 1 h at 0° C. The reaction mixture was then concentrated and the residue was purified by prep-HPLC (MeOH/H$_2$O, 0.05% TFA) to give the title compound (14 mg, 91%) as a light yellow solid after lyophilisation. LC-MS (m/z): 474 [M+H]$^+$. $^1$H NMR (500 MHz, DMSO-d$_6$) δ 11.87 (d, J=3.1 Hz, 1H), 10.25 (s, 1H), 8.48 (d, J=3.0 Hz, 1H), 8.39 (s, 2H), 8.32 (s, 1H), 7.85 (t, J=21.2 Hz, 1H), 7.46 (t, J=8.6 Hz, 2H), 7.19 (s, 2H), 6.38 (dd, J=17.0, 10.1 Hz, 1H), 6.25 (dd, J=17.0, 2.0 Hz, 1H), 5.78 (dd, J=10.0, 2.0 Hz, 1H), 4.27 (s, 1H), 4.06 (d, J=13.4 Hz, 1H), 3.06 (dd, J=24.8, 13.0 Hz, 2H), 2.09 (s, 1H), 1.91 (s, 1H), 1.74-1.56 (m, 2H).

Example 10. Synthesis of (R,E)-N-(6-(3-((5-chloro-4-(1H-indol-3-yl)pyrimidin-2-yl)amino)piperidin-1-yl)pyridin-3-yl)-4-(dimethylamino)but-2-enamide (BSJ-02-108)

To a cold solution (0° C.) of (R)—N-(1-(5-aminopyridin-2-yl)piperidin-3-yl)-5-chloro-4-(1H-indol-3-yl)pyrimidin-2-amine (15 mg, 0.035 mmol) and 0.1 mL of DIPEA in 2.0 mL of anhydrous CH$_3$CN was added a solution of (E)-4-bromobut-2-enoyl chloride (6.34 mg, 0.035 mmol) in 1.0 mL of DCM dropwise. After 0.5 h at 0° C., a 2M solution of dimethylamine in THF (1.0 mL) was added and the mixture was stirred for 1 h at 0° C. Then 1.5 mL of DMSO was added, followed by removal of the low boiling point solvents under reduced pressure. The residue was purified by prep-HPLC (MeOH/H$_2$O, 0.05% TFA) to give the title compound (16 mg, 86%) as a light yellow solid after lyophilisation. LC-MS (m/z): 531 [M+H]$^+$. $^1$H NMR (500 MHz, DMSO-d$_6$) δ 11.91 (s, 1H), 10.20 (s, 1H), 8.68 (d, J=3.0 Hz, 1H), 8.39 (s, 2H), 8.30 (s, 1H), 7.9-7.66 (m, 1H), 7.46 (t, J=8.6 Hz, 2H), 7.11 (s, 2H), 6.45 (dd, J=17.0, 10.1 Hz, 1H), 6.22-6.03 (m, 1H), 5.78 (dd, J=10.0, 2.0 Hz, 1H), 4.27 (s, 1H), 4.16-3.99 (m, 3H), 3.26-3.08 (m, 2H), 2.84 (s, 6H), 2.19 (s, 1H), 1.90 (s, 1H), 1.76-1.51 (m, 2H).

Example 11. Synthesis of (R)—N-(4-(3-((5-chloro-4-(1H-indol-3-yl)pyrimidin-2-yl)amino)piperidin-1-yl)-5-fluoro-2-methylphenyl)acrylamide (BSJ-03-005)

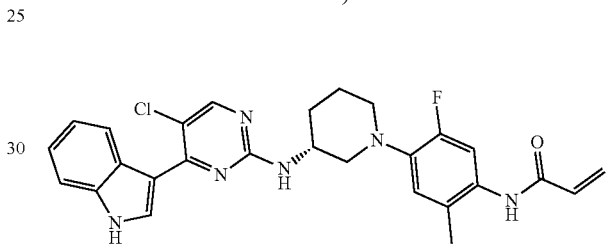

Example 11 was synthesized via a procedure similar to Example 8. LC-MS (m/z): 505 [M+H]$^+$. $^1$H NMR (500 MHz, DMSO-d$_6$) δ 11.87 (s, 1H), 9.38 (s, 1H), 8.49 (d, J=3.1 Hz, 1H), 8.28 (s, 1H), 7.47 (d, J=8.1 Hz, 1H), 7.35 (d, J=14.1 Hz, 2H), 7.19 (d, J=14.8 Hz, 1H), 6.92 (d, J=9.5 Hz, 1H), 6.52 (dd, J=17.0, 10.2 Hz, 1H), 6.22 (dd, J=17.0, 2.1 Hz, 1H), 5.73 (dd, J=10.2, 2.1 Hz, 1H), 3.31 (d, J=11.7 Hz, 1H),

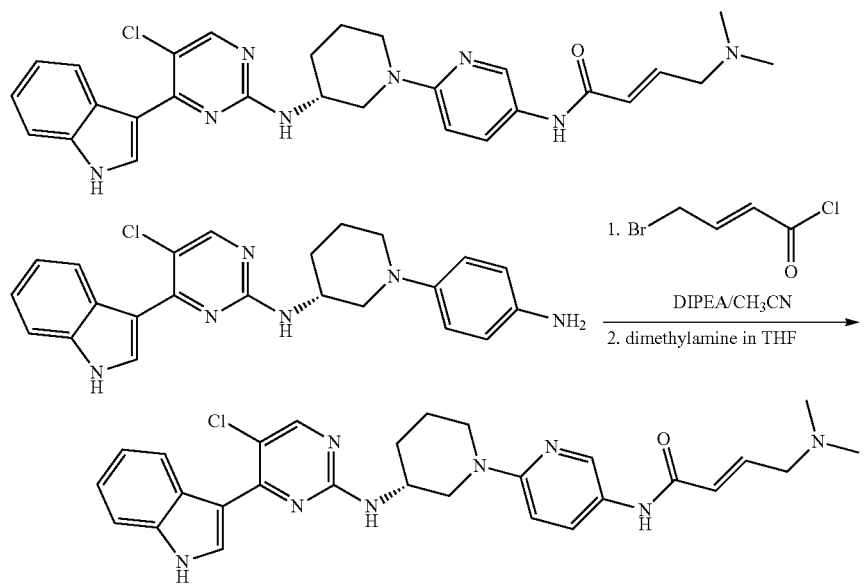

2.76-2.57 (m, 2H), 2.22-1.93 (m, 4H), 1.92-1.62 (m, 2H), 1.55 (qd, J=11.9, 4.0 Hz, 1H).

Example 12. (R)—N-(4-(3-((5-chloro-4-(1H-indol-3-yl)pyrimidin-2-yl)amino)piperidin-1-yl)-5-methoxy-2-methylphenyl)acrylamide (BSJ-03-014)

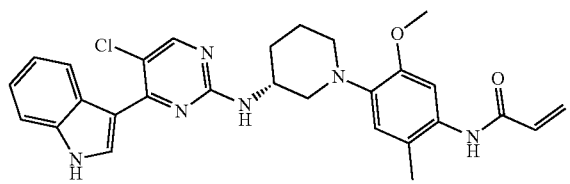 [SMILES: C=CC(=O)Nc1cc(OC)c(N2CCC[C@@H](Nc3ncc(Cl)c(-c4c[nH]c5ccccc45)n3)C2)cc1C]

Example 12 was synthesized via a procedure similar to Example 8. LC-MS (m/z): 517 [M+H]+. 1H NMR (500 MHz, DMSO-d6) δ 11.86 (s, 1H), 9.41 (s, 1H), 8.48 (d, J=3.1 Hz, 1H), 8.29 (s, 1H), 7.48 (d, J=8.2 Hz, 1H), 7.22 (d, J=36.4 Hz, 3H), 6.52 (dd, J=17.0, 10.2 Hz, 1H), 6.22 (dd, J=17.0, 2.1 Hz, 1H), 5.72 (dd, J=10.3, 2.1 Hz, 1H), 3.14 (qd, J=7.4, 4.2 Hz, 2H), 2.11 (s, 3H), 1.96-1.51 (m, 3H), 1.26 (s, 7H).

Example 13. N-(4-(((1R,3R)-3-((5-chloro-4-(1H-indol-3-yl)pyrimidin-2-yl)amino)cyclohexyl)oxy)-3-fluorophenyl)acrylamide (BSJ-03-161)

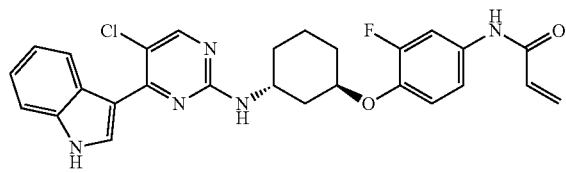 [SMILES: C=CC(=O)Nc1ccc(O[C@@H]2CCC[C@@H](Nc3ncc(Cl)c(-c4c[nH]c5ccccc45)n3)C2)c(F)c1]

Example 13 was synthesized via a procedure similar to Example 1. LC-MS (m/z): 506 [M+H]+. 1H NMR (500 MHz, DMSO-d6) δ 11.88 (s, 1H), 10.18 (s, 1H), 8.67 (d, J=8.1 Hz, 1H), 8.52 (s, 1H), 8.26 (s, 1H), 7.69 (dd, J=13.5, 2.5 Hz, 1H), 7.49 (d, J=8.1 Hz, 1H), 7.34-7.25 (m, 1H), 7.25-7.17 (m, 2H), 7.11 (s, 1H), 6.38 (dd, J=16.9, 10.1 Hz, 1H), 6.24 (dd, J=17.0, 2.0 Hz, 1H), 5.75 (dd, J=10.1, 2.0 Hz, 1H), 4.78 (s, 1H), 3.17 (s, 1H), 2.17 (d, J=13.2 Hz, 1H), 1.81 (d, J=13.8 Hz, 3H), 1.67-1.46 (m, 2H), 1.46-1.20 (m, 1H).

Example 14. (E)-N-(4-(((1R,3R)-3-((5-chloro-4-(1H-indol-3-yl)pyrimidin-2-yl)amino)cyclohexyl)oxy)-3-fluorophenyl)-4-(dimethylamino)but-2-enamide (BSJ-03-162)

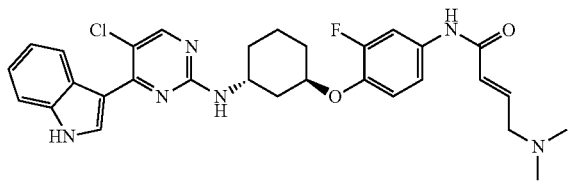 [SMILES: CN(C)C/C=C/C(=O)Nc1ccc(O[C@@H]2CCC[C@@H](Nc3ncc(Cl)c(-c4c[nH]c5ccccc45)n3)C2)c(F)c1]

Example 14 was synthesized via a procedure similar to Example 2. LC-MS (m/z): 563 [M+H]+. 1H NMR (500 MHz, DMSO-d6) δ 11.86 (s, 1H), 10.37 (s, 1H), 9.80 (s, 1H), 8.66 (d, J=8.0 Hz, 1H), 8.50 (s, 1H), 8.25 (d, J=3.6 Hz, 1H), 7.69 (dd, J=13.3, 2.5 Hz, 1H), 7.48 (d, J=8.1 Hz, 1H), 7.33-7.09 (m, 4H), 6.73 (dt, J=14.8, 7.2 Hz, 1H), 6.49-6.33 (m, 1H), 4.79 (s, 1H), 3.97-3.91 (m, 2H), 2.80 (s, 6H), 2.17 (d, J=13.1 Hz, 1H), 1.81 (d, J=14.2 Hz, 3H), 1.68-1.48 (m, 2H), 1.48-1.18 (m, 1H).

Example 15. (R)—N-(4-(3-(5-chloro-4-(1H-indol-3-yl)pyrimidin-2-ylamino)piperidin-1-yl)-2-methylphenyl)acrylamide (BSJ-03-012)

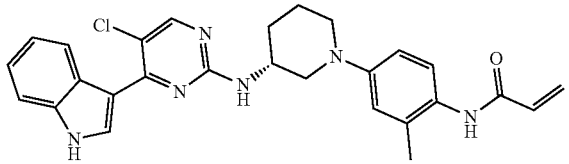 [SMILES: C=CC(=O)Nc1ccc(N2CCC[C@@H](Nc3ncc(Cl)c(-c4c[nH]c5ccccc45)n3)C2)cc1C]

Example 15 was synthesized via a procedure similar to Example 8. LC-MS (m/z): 487 [M+H]+.

Example 16. (R)—N-(4-(3-(5-chloro-4-(1H-indol-3-yl)pyrimidin-2-ylamino)piperidin-1-yl)-3-fluorophenyl)acrylamide (BSJ-03-018)

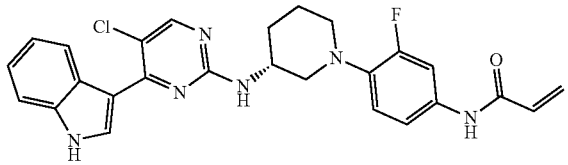 [SMILES: C=CC(=O)Nc1ccc(N2CCC[C@@H](Nc3ncc(Cl)c(-c4c[nH]c5ccccc45)n3)C2)c(F)c1]

Example 16 was synthesized via a procedure similar to Example 8. LC-MS (m/z): 491 [M+H]+.

Example 17 (E)-N-(4-(((1S,3R)-3-((5-chloro-4-(1H-indol-3-yl)pyrimidin-2-yl)amino)cyclohexyl)oxy)phenyl)-4-(dimethylamino)but-2-enamide (BSJ-03-149)

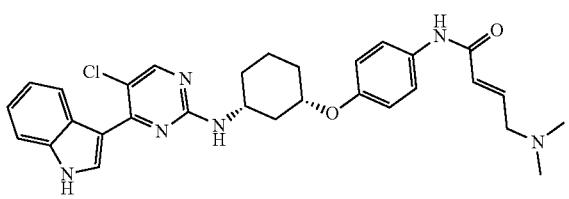 [SMILES: CN(C)C/C=C/C(=O)Nc1ccc(O[C@H]2CCC[C@@H](Nc3ncc(Cl)c(-c4c[nH]c5ccccc45)n3)C2)cc1]

Example 17 was synthesized via a procedure similar to Example 2, LC-Mz (m/z) 546 [M+H]+.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I'):

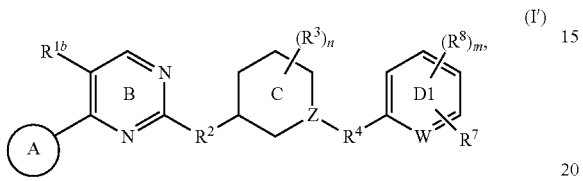

or a pharmaceutically acceptable salt, solvate, hydrate, tautomer, or stereoisomer thereof, wherein:

Ring A is an optionally substituted indole ring;

Z is —CH— and $R^4$ is —O—; or Z is —N— and $R^4$ is —C(=O)— or a bond;

$R^{1b}$ is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{B1a}$, —$N(R^{B1b})_2$, and $SR^{B1a}$, $R^{B1a}$ is selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom, wherein each occurrence of $R^{B1b}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of $R^{B1b}$ are taken together with their intervening atoms to form a substituted or unsubstituted heterocyclic or substituted or unsubstituted heteroaryl ring;

R2 is —$N(R^6)$;

each instance of $R^3$, if present, is independently selected from halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{Cl}$, —$N(R^{C1a})_2$, and —$SR^{Cl}$, wherein each occurrence of $R^{Cl}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of $R^{C1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of $R^{C1a}$ are taken together with their intervening atoms to form a substituted or unsubstituted heterocyclic or substituted or unsubstituted heteroaryl ring; or two $R^3$ groups bound to the same ring carbon atom are taken together to form =O, or two $R^3$ groups bound to the same or different ring carbon atoms are joined to form an optionally substituted carbocyclyl, optionally substituted heterocyclyl, optionally substituted aryl, or optionally substituted heteroaryl ring;

each $R^6$ is independently selected from hydrogen and —$C_1$-$C_6$ alkyl;

$R^7$ is a warhead of formula:

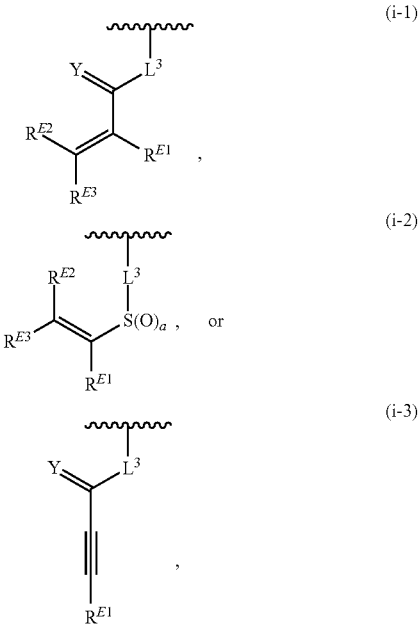

wherein:

$L^3$ is a bond or an optionally substituted $C_{1-4}$ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$—, —OS(=O)$_2$—, —S(=O)$_2$NR$^{L3a}$—, or NR$^{L3a}$S(=O)$_2$, wherein each instance of R$^{L3a}$ is independently hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

each instance of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

each instance of Y is independently O, S, or NR$^{E7}$, wherein each instance of R$^{E7}$ is independently hydrogen, substituted or unsubstituted C$_{1-6}$ alkyl, or a nitrogen protecting group;

a is 1 or 2; and

W is —N=;

each instance of R$^8$, if present, is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$, wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom, wherein each occurrence of R$^{D1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of R$^{D1a}$ are taken together with their intervening atoms to form a substituted or unsubstituted heterocyclic or substituted or unsubstituted heteroaryl ring; or two R$^8$ groups are joined to form an optionally substituted carbocyclyl, optionally substituted heterocyclyl, optionally substituted aryl, or optionally substituted heteroaryl ring;

m is 0, 1, 2, or 3; and n is 0, 1, 2, 3, 4, 5 or 6.

2. The compound of claim 1, or a pharmaceutically acceptable salt, solvate, hydrate, tautomer, or stereoisomer thereof, wherein Ring A is of formula:

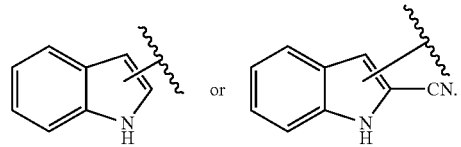

3. The compound of claim 1, or a pharmaceutically acceptable salt, solvate, hydrate, tautomer, or stereoisomer thereof, wherein Ring A is of formula:

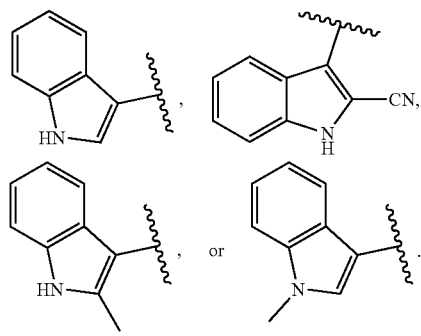

4. The compound of claim 1, or a pharmaceutically acceptable salt, solvate, hydrate, tautomer, or stereoisomer thereof, wherein R$^{1b}$ is halogen.

5. The compound of claim 1, or a pharmaceutically acceptable salt, solvate, hydrate, tautomer, or stereoisomer thereof, wherein R$^6$ is H.

6. The compound of claim 1, or a pharmaceutically acceptable salt, solvate, hydrate, tautomer, or stereoisomer thereof, wherein at least one instance of R$^8$ is halogen, —O(alkyl), or optionally substituted alkyl.

7. The compound of claim 1, or a pharmaceutically acceptable salt, solvate, hydrate, tautomer, or stereoisomer thereof, wherein Z is —CH— and R$^4$ is —O—.

8. The compound of claim 1, or a pharmaceutically acceptable salt, solvate, hydrate, tautomer, or stereoisomer thereof, wherein Z is —N— and R$^4$ is —C(=O)—.

9. The compound of claim 1, or a pharmaceutically acceptable salt, solvate, hydrate, tautomer, or stereoisomer thereof, wherein n is 0.

10. The compound of claim 1, or a pharmaceutically acceptable salt, solvate, hydrate, tautomer, or stereoisomer thereof, wherein Z is —N— and R$^4$ is a bond.

11. The compound of claim 1, or a pharmaceutically acceptable salt, solvate, hydrate, tautomer, or stereoisomer thereof, wherein m is 0.

12. The compound of claim 1, or a pharmaceutically acceptable salt, solvate, hydrate, tautomer, or stereoisomer thereof, wherein $R^7$ is of formula:

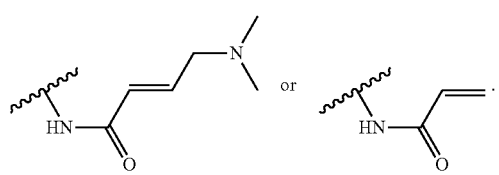

13. The compound of claim 1, wherein the compound is of formula:

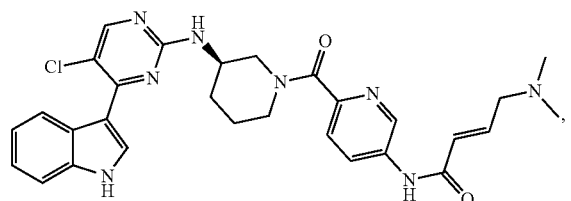

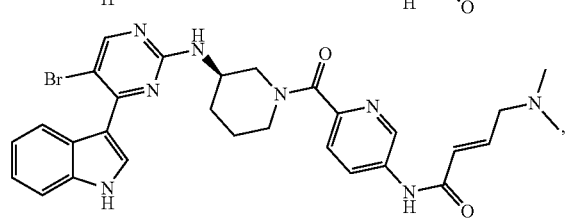

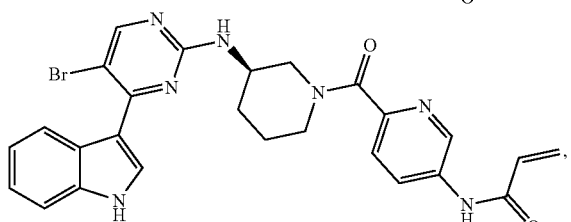

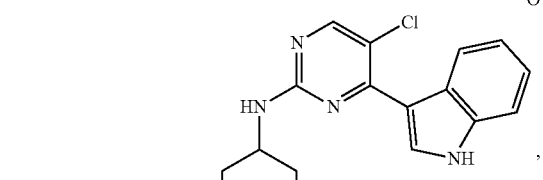

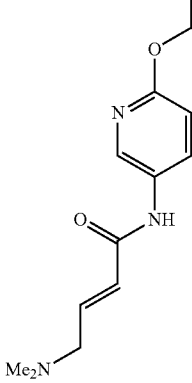

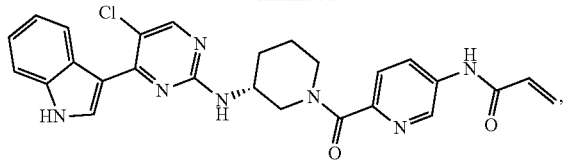

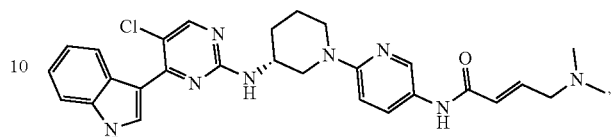

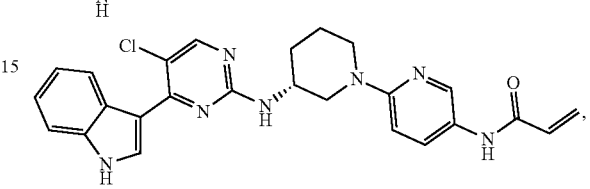

or a pharmaceutically acceptable salt, solvate, hydrate, tautomer, or stereoisomer thereof.

14. The compound of claim 1, wherein the compound is a compound of Formula (I'):

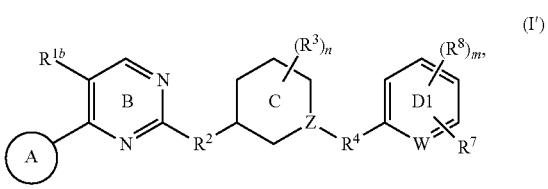

or a pharmaceutically acceptable salt thereof.

15. A compound of the formula:

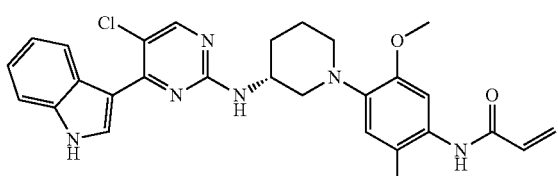

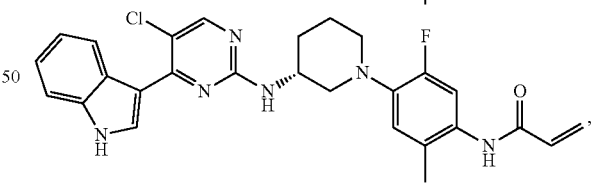

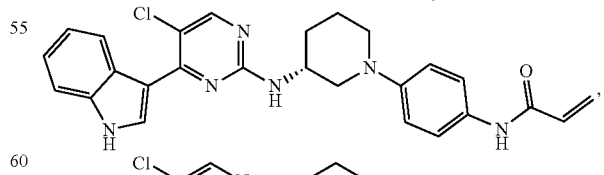

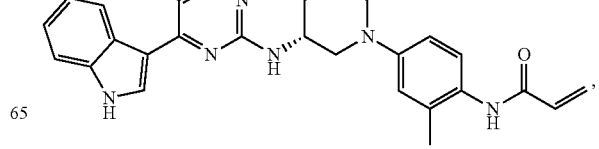

-continued

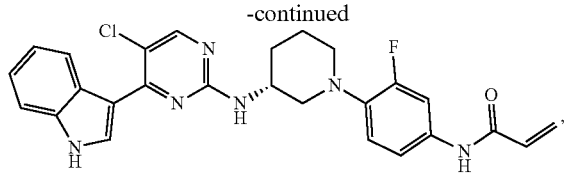

or a pharmaceutically acceptable salt, solvate, hydrate, tautomer, or stereoisomer thereof.

16. A pharmaceutical composition comprising a compound of claim 1, or a pharmaceutically acceptable salt, solvate, hydrate, tautomer, or stereoisomer thereof, and a pharmaceutically acceptable excipient.

17. A method of treating a proliferative disease in a subject in need thereof, the method comprising administering to the subject a therapeutically effective amount of a compound of claim 1, or a pharmaceutically acceptable salt, solvate, hydrate, tautomer, or stereoisomer thereof.

18. A method of inhibiting the activity of a cyclin-dependent kinase (CDK) in a biological sample or subject, the method comprising administering to the subject or contacting the biological sample with a therapeutically effective amount of a compound of claim 1, or a pharmaceutically acceptable salt, solvate, hydrate, tautomer, or stereoisomer thereof.

19. A method of inhibiting transcription in a biological sample or subject, the method comprising:
administering to the subject or contacting the biological sample with a therapeutically effective amount of a compound of claim 1, or a pharmaceutically acceptable salt, solvate, hydrate, tautomer, or stereoisomer thereof.

20. A method of inhibiting cell growth in a biological sample or subject, the method comprising:
administering to the subject or contacting the biological sample with a therapeutically effective amount of a compound of claim 1, or a pharmaceutically acceptable salt, solvate, hydrate, tautomer, or stereoisomer thereof.

21. A method of inducing apoptosis of a cell in a biological sample or subject, the method comprising:
administering to the subject or contacting the biological sample with a therapeutically effective amount of a compound of claim 1, or a pharmaceutically acceptable salt, solvate, hydrate, tautomer, or stereoisomer thereof.

22. The compound of claim 4, or a pharmaceutically acceptable salt, solvate, hydrate, tautomer, or stereoisomer thereof, wherein $R^{1b}$ is Cl.

23. The compound of claim 4, or a pharmaceutically acceptable salt, solvate, hydrate, tautomer, or stereoisomer thereof, wherein $R^{1b}$ is Br.

24. A pharmaceutical composition comprising a compound of claim 15, or a pharmaceutically acceptable salt, solvate, hydrate, tautomer, or stereoisomer thereof, and a pharmaceutically acceptable excipient.

25. A method of treating a proliferative disease in a subject in need thereof, the method comprising administering to the subject a therapeutically effective amount of a compound of claim 15, or a pharmaceutically acceptable salt, solvate, hydrate, tautomer, or stereoisomer thereof.

26. A method of inhibiting the activity of a cyclin-dependent kinase (CDK) in a biological sample or subject, the method comprising administering to the subject or contacting the biological sample with a therapeutically effective amount of a compound of claim 15, or a pharmaceutically acceptable salt, solvate, hydrate, tautomer, or stereoisomer thereof.

27. A method of inhibiting transcription in a biological sample or subject, the method comprising:
administering to the subject or contacting the biological sample with a therapeutically effective amount of a compound of claim 15, or a pharmaceutically acceptable salt, solvate, hydrate, tautomer, or stereoisomer thereof.

28. A method of inhibiting cell growth in a biological sample or subject, the method comprising:
administering to the subject or contacting the biological sample with a therapeutically effective amount of a compound of claim 15, or a pharmaceutically acceptable salt, solvate, hydrate, tautomer, or stereoisomer thereof.

29. A method of inducing apoptosis of a cell in a biological sample or subject, the method comprising:
administering to the subject or contacting the biological sample with a therapeutically effective amount of a compound of claim 15, or a pharmaceutically acceptable salt, solvate, hydrate, tautomer, or stereoisomer thereof.

30. The compound of claim 15, wherein the compound is of the formula:

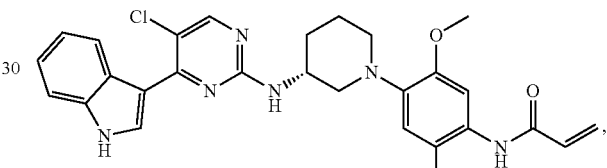

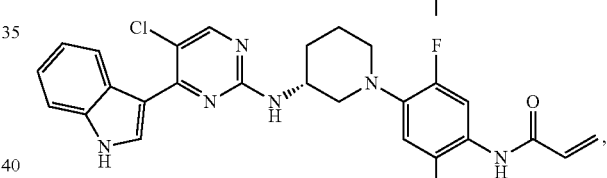

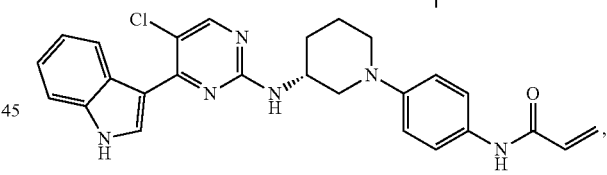

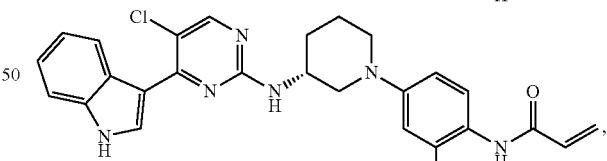

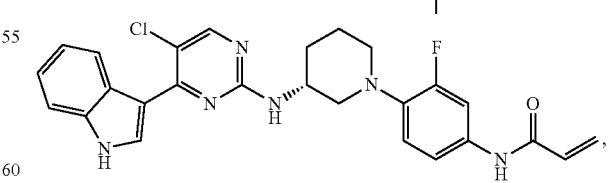

or a pharmaceutically acceptable salt thereof.

* * * * *

UNITED STATES PATENT AND TRADEMARK OFFICE
CERTIFICATE OF CORRECTION

PATENT NO. : 11,932,625 B2
APPLICATION NO. : 17/688822
DATED : March 19, 2024
INVENTOR(S) : Nathanael S. Gray et al.

Page 1 of 1

It is certified that error appears in the above-identified patent and that said Letters Patent is hereby corrected as shown below:

In the Claims

At Column 197, Line 34, please replace: "and $SR^{B1a}$," with --and $-SR^{B1a}$;--

At Column 197, Line 54, please replace: "R2 is $-N(R^6)$;" with --$R^2$ is $-N(R^6)$-;--

At Column 197, Lines 61-62, please replace: "heteroaryl, $-OR^{C1}$,) $-N(R^{C1a})_2$, and $-SR^{C1}$," with --heteroaryl, $-OR^{C1}$, $-N(R^{C1a})_2$, and $-SR^{C1}$,--

At Column 199, Lines 4-5, please replace: "trans–$CR^{L3b}=CR^{L3b}$, cis–$CR^{L3b}=CR^{L3b}$–," with --*trans*–$CR^{L3b}=CR^{L3b}$–, *cis*–$CR^{L3b}=CR^{L3b}$–,--

At Column 199, Lines 8-9, please replace: "–$S(=O)_2$–, –$OS(=O)_2$–, –$S(=O)_2NR^{L3a}$–, or $NR^{L3a}S(=O)_2$," with -- –$S(=O)_2O$–, –$OS(=O)_2$–, –$S(=O)_2NR^{L3a}$–, or –$NR^{L3a}S(=O)_2$–,--

Signed and Sealed this
Sixth Day of August, 2024

Katherine Kelly Vidal
*Director of the United States Patent and Trademark Office*